US008624086B2

(12) United States Patent
Parish et al.

(10) Patent No.: US 8,624,086 B2
(45) Date of Patent: Jan. 7, 2014

(54) NUCLEIC ACID MOLECULES AND THEIR USE IN PLANT STERILITY

(75) Inventors: Roger Parish, Warrandyte (AU); Song Li, Bulleen (AU); Sylvana Iacuone, Mill Park (AU); Roger Kalla, Ivanhoe East (AU); Trudi Higginson, Kensington (AU)

(73) Assignee: La Trobe University, Attwood, Victoria (AU)

( * ) Notice: Subject to any disclaimer, the term of this patent is extended or adjusted under 35 U.S.C. 154(b) by 0 days.

(21) Appl. No.: 13/430,579

(22) Filed: Mar. 26, 2012

(65) Prior Publication Data
US 2012/0185963 A1 Jul. 19, 2012

Related U.S. Application Data

(60) Division of application No. 11/494,919, filed on Jul. 28, 2006, now Pat. No. 8,163,975, which is a continuation-in-part of application No. PCT/AU2005/000851, filed on Jun. 15, 2005.

(30) Foreign Application Priority Data

Jun. 15, 2004 (AU) ................................. 2004903246

(51) Int. Cl.
*C12N 15/82* (2006.01)
*C12N 15/29* (2006.01)
*C12N 15/62* (2006.01)
*C12N 5/10* (2006.01)
*A01H 5/00* (2006.01)

(52) U.S. Cl.
USPC ........... 800/303; 800/278; 800/287; 800/306; 800/320; 536/23.6; 435/419

(58) Field of Classification Search
None
See application file for complete search history.

(56) References Cited

U.S. PATENT DOCUMENTS

| 8,163,975 B2 | 4/2012 | Parish |
| 2003/0131386 A1 | 7/2003 | Adam et al. |
| 2004/0045049 A1 | 3/2004 | Adam et al. |

FOREIGN PATENT DOCUMENTS

| WO | WO 01/36598 A | 5/2001 |
| WO | WO 02/27001 A | 4/2002 |
| WO | WO 03007699 A2 * | 1/2003 |
| WO | WO 2004/031349 | 4/2004 |

OTHER PUBLICATIONS

Jiang et al. (2004) Gene 326: 13-22.*
Arabidopsis eFP Browser (bar.utoronto.ca): At1g63910.*
Higginson et al (2003) The Plant Journal 35: 177-192.*
Li et al (1999) Plant Cell Physiology 40: 343-347.*
Hiratsu et al (2003) The Plant Journal 34: 733-739.*
Li et al (1999) Locus AF048839.*
Arabidopsis eFP Browser (bar.utoronto.ca): At1g63910, 2013.*
Albani, et al. (1991) A gene showing sequence similarity to pectin esterase is specifically expressed in developing pollen of *Brassica napus*. Sequences in its 5' flanking region are conserved in other pollen-specific promoters. Molecular Biology, 16: 501-513.
Alexander MP, et al. (1969) Differential Staining of Aborted and Nonaborted Pollen. Stain Technol., 44: 117-122.
Altschul, et al. (1996) Local Alignment Statistics. Methods in Enzymology, 266: 460-480.
Altschul, et al. (1997) Gapped BLAST and PSI-BLAST: a new generation of protein database search programs. Nucleic Acids Res., 25: 3389-3402.
Aoyama T, et al. (1997) A glucocorticoid-mediated transcriptional induction system in transgenic plants. The Plant Journal, 11(3): 605-612.
"*Arabidopsis thaliana* Atmyb103 (MYB103) gene, complete cds." (Jun. 29, 1999) XP002598422 retrieved from EBI accession No. EMBL:AF048839.
Bechtold, et al. In-Planta Agrobacterium-Mediated Bene-Transfer by Infiltration of Adult *Arabidopsis-Thaliana* Plants. C.R. Acad. Sci. Paris, Life Sciences, 36: 1194-1199 (Abstract), Oct. 1993.
Birnboim, et al. (1983) A Rapid Alkaline Extraction Method for the Isolation of Plasmid DNA. Enzymology, 100: 243-255.
Caissard, et al. (1992) Electron microscopy and X-ray microanalysis as tools for fine localization of the β-glucaronidase activity in transgenic plants harbouring the GUS reporter gene. Protoplasma, 170: 68-76.
Carpenter, et al. (1992) Preferential Expression of an α-Tubulin Gene of *Arabidopsis* in Pollen. Plant Cell, 4:557-571.
Database EMBL [Online] Jul. 11, 2003, BN15. 020H07F020211 BN15 *Brassica napus* cDNA clone BN15020H07, mRNA sequence. XP002477301 retrieved from EBI accession No. EMBL: CD813645 Database accession No. CD813645.
Database EMBL [Online] Nov. 26, 1999, "*Arabidopsis thaliana* DNA-binding protein (MYB32) gene, complete cds." XP002477302 retrieved from EBI accession No. EMBL: U26933 Database accession No. U26933.

(Continued)

*Primary Examiner* — David T Fox
*Assistant Examiner* — Steven Bernacki
(74) *Attorney, Agent, or Firm* — Ballard Spahr LLP

(57) ABSTRACT

The present invention provides a method for disrupting pollen development in a plant, the method comprising inhibiting the expression of an endogenous nucleic acid molecule which is, under normal conditions, detectably expressed in anther tissue of a plant during pollen formation, and which codes for a protein belonging to the MYB class of DNA binding transcription factors. Particularly, the nucleic acid molecule whose expression is blocked encodes MYB 32 or MYB 103. The invention also provides nucleic acid molecules for use in the method, use of the method in producing male sterile plants and transgenic plants produced in accordance with the method.

11 Claims, 52 Drawing Sheets

(56) References Cited

OTHER PUBLICATIONS

Database EMBL [Online] Dec. 26, 2006, "*Brassica rapa* clone 739 MYB-like protein mRNA, complete cds." XP002477303 retrieved from EBI accession No. EMBL: EF110972 Database accession No. EF110972.

Ditta, et al. (1980) Broad host range DNA cloning system for Gram-negative bacteria: construction of a gene bank of *Rhizobium meliloti*. PNAS, 77: 7347-7351.

Eyal, et al. (1995) Pollen Specificity Elements Reside in 30 bp of the Proximal Promoters of Two Pollen-Expressed Genes. Plant Cell, 7: 373-384.

Hiratsu, et al. (2003) Dominant repression of target genes by chimeric repressors that include the EAR motif, a repression domain, in *Arabidopsis*. Plant J., 35: 177-192.

Goldberg, et al. (1993) Anther Development: Basic Principles and Practical Applications. Plant Cell, 5: 1217-1229.

Jefferson (1987) GUS fusions: β-glucuronidase as a sensitive and versatile gene fusion marker in higher plants. EMBO J., 6: 3901-3907.

Jin H, et al. (2000) Transcriptional repression by AtMYB4 controls production of UV-protecting sunscreens in *Arabidopsis*. EMBO J, 15: 6150.

Klimyuk, et al. (1993) Alkali treatment for rapid preparation of plant material for reliable PCR analysis. Plant J., 3: 493-494.

Lazo. (1991) A DNA transformation-competent Arabidopsis genomic library in Agrobacterium. Biotechnology, 9: 963-967.

Li SF, et al. (1995) Isolation of two novel myb-like genes from *Arabidopsis* and studies on the DNA-binding properties of their products. Plant J., 8: 963.

Li, et al. (1999) A Novel MYB-Related Gene from *Arabidopsis thaliana* Expressed in Developing Anthers. Plant and Cell Physiology, Japanese Society of Plant Physiologists, JP, 40(3): 343-347.

Lin, et al. (2003) Organ-specific, developmentally-regulated and abiotic stress-induced activities of four *Arabidopsis thaliana* promoters in transgenic white clover (*Trifoliumrepens L.*). Plant Science, 165: 1437-1444.

Murray, et al. (2003) A role for HvGAMYB in anther development. The Plant Journal, 33: 481-491.

Paul, et al. (1992) The isolation and characterization of the tapetum-specific *Arabidopsis thaliana* A9 gene. Plant Molecular Biology, 19: 611-622.

Preston J, et al. (2004) AtMYB32 is required for normal pollen development in *Arabidopsis thaliana*. Plant Journal, 40(6): 979-995.

Romero, et al. (1998) More than 80R2R3-MYB regulatory genes in the genome of *Arabidopsis thaliana*. The Plant J., 14: 273-284.

Sanders, et al. (1999) Anther development defects in *Arabidopsis thaliana* male-sterile mutants. Sex. Plant Reprod., 11: 297-322.

Snustad, et al. (1992) The Small Genome of *Arabidopsis* contains at Least Nine Expressed β-Tubulin Genes. The Plant Cell, 4: 549-556.

Sorensen AM, et al. (2003) The *Arabidopsis* Aborted Microspores (AMS) gene encodes a MYC class transcription factor. The Plant Journal, 33: 413-423.

Steiner-Lange, et al. (2003) Disruption of *Arabidopsis thaliana* MYB26 results in male sterility due to non-dehiscent anthers. The Plant Journal, 34: 519-528.

"SubName: Full=Atmyb103; SubName: Full=MYB transcription factor; SubName: Full=Putative uncharacterized protein At5g56110." (Nov. 1, 1999) XP002598423 retrieved from EBI accession No. UNIPROT: Q9XHVO.

Twell, et al. (1991) Promoter analysis of genes that are coordinately expressed during pollen development reveals pollen-specific enhancer sequences and shared regulatory elements. Genes & Development, 5: 496-507.

Valvekens, et al. (1988) *Agrobacterium tumefaciens*-mediated transformation of *Arabidopsis thaliana* root explants by using kanamycin selection. PNAS, 85: 5536-5540.

van Tunen, et al. (1990) Pollen—and Anther-Specific chi Promoters from *petunia*: Tandem Promoter Regulation of the chiA Gene. Plant Cell, 2: 393-401.

Waterhouse, et al. (1998) Virus resistance and gene silencing in plants can be induced by simultaneous expression of sense and antisense in RNA. Proc. Natl. Acad. Sci. USA, 95: 13959-13964.

Wu, et al. (1998) A comparison of the promoter regions of three pollen-specific genes in alfalfa. Sexual Plant Reproduction, 11: 181-182.

Yang S, et al. (2001) Novel Anther-Specific *myb* Genes from Tobacco as Putative Regulators of Phenylalanine Ammonia-Lyase Expression. Plant Physiology, 126: 1738-1753.

Zhang ZB, et al. (2007) Transcription factor AtMYB103 is required for another development by regulating tapetum development, callose dissolution and exine formation in *Arabidopsis*. Plant J., 52(3): 528-238.

Partial European Search Report for EP Application No. 10172161.1 issued by the European Patent Office on Sep. 9, 2010.

International Preliminary Report on Patentability issued by the International Bureau on Dec. 20, 2006 for PCT/AU2005/000851 filed on Jun. 15, 2005 and published as WO 2005/122751 on Dec. 29, 2005 (Applicant-La Trobe University // Inventors-Parish et al.) (7 pages).

International Search Report issued by the International Bureau on Sep. 8, 2005 for PCT/AU2005/000851 filed on Jun. 15, 2005 and published as WO 2005/122751 on Dec. 29, 2005 (Applicant-La Trobe University // Inventors-Parish et al.) (5 pages).

Written Opinion issued by the International Bureau on Sep. 8, 2005 for PCT/AU2005/000851 filed on Jun. 15, 2005 and published as WO (Applicant -La Trobe University // Inventors-Parish et al.) (6 pages).

\* cited by examiner

MGRSPCCEKDHTNKGAWTKEEDDKLVSYIKSHGEGCWRSLPRSAGLLRCGKSCRLRWINYLRPDLKR
GNFTLEEDDLIIKLHSLLGNKWSLIATRLPGRTDNEIKNYWNTHVKRKLLRGGIDPTTHRPINEAKA
PRDSSETRETEDSLVKPLSPSRQLEKKESFGEERNDQKGLICKKERVEYSIVEEKCLDLNLELRISP
PWQDQQHHDETKLWFGKEKYMCTACRFGLGNGKKCSCDNVKCQVEYSSSSSSHSSSDISSSVIGYDF
LG

TGATAAGCTTATGGGAAGGTCTCCTTGCTGTGAGAAGGACCACACGAACAAAGGAGCTTGGACTAAA
GAAGAAGACGATAAGCTCGTCTCTTACATCAAATCTCACGGCGAAGGCTGTTGGCGCTCTCTTCCAA
GATCCGCCGGTCTTCTCCGCTGCGGCAAAAGCTGCCGTCTTCGGTGGATTAACTATCTCCGACCTGA
TCTCAAGAGAGGTAACTTCACCCTCGAAGAAGACGATCTCATCATCAAACTCCATAGCCTCCTTGGA
AACAAATGGTCTCTTATCGCGACGAGATTACCGGGGAGAACAGATAACGAGATCAAGAACTACTGGA
ATACACACGTAAAGAGGAAGCTTTTGAGAGGAGGGATTGATCCCACGACTCATCGGCCGATCAACGA
AGCCAAAGCTCCTCGTGATTCGTCTGAGACTAGAGAGACAGAGGACTCGCTTGTGAAGTTTCTATCT
TTCAGTCGTCAACTGGAGAAAAAGGAAAGTTTTGGGGAAGAGAGAAATGATCAGAAAGGACTGATTT
GCAAAAAAGAGAGAGTTGAGTATTCGATTGTTGAAGAAAAGTGCTTAGATTTGAATCTTGAGCTTAG
AATCAGCCCGCCATGGCAAGACCAACAGCACCATGATGAGACCAAACTTTGGTTTGGGAAAGAGAAG
TACATGTGCACTGCATGCCGTTTTGGGTTGGGAAACGGCAAGAAGTGTAGCTGCGATAATGTTAAAT
GTCAAGTCGAGTACAGTAGTAGCAGCAGCAGCCATTCTTCAAGCGATATTAGTAGTAGCGTTATTGG
TTATGACTTCTTGGGTA

FIGURE 1

MGRIPCCEKE NVKRGQWTPE EDNKLASYIA QHGTRNWRLI PKNAGLQRCG
KSCRLRWTNY LRPDLKHGQF SEAEEHIIVK FHSVLGNRWS LIAAQLPGRT
DNDVKNYWNT KLKKKLSGMG IDPVTHKPFS HLMAEITTTL NPPQVSHLAE
AALGCFKDEM LHLLTKKRVD LNQINFSSPN PNNFTRTVDS EAGKMKMDGL
ENGNGIMKLW DMGNGFSYGS SSSSFGNEDK NDGAASPAVA AWRGHGGIRT
AVAETAAAEE EERRKLKGEV VDQEENGSQG GRGDGMLMMR SQHDQHQHHV
FNVDNVLWDL QADDLINHVV

ATGGGTAGGATTCCATGCTGTGAAAAGGAGAATGTGAAGAGAGGGCAATGGACTCCTGAAGAAGA
CAACAAACTGGCTTCTTACATTGCTCAACATGGTACTCGTAATTGGCGTCTCATCCCTAAAAACG
CTGGATTGCAGAGATGTGGAAAGAGTTGTAGACTACGGTGGACAAACTATTTGCGTCCTGACCTG
AAACATGGTCAATTTTCTGAGGCTGAAGAACATATCATCGTCAAGTTTCACTCTGTTCTTGGTAA
CCGGTGGTCGTTGATTGCGGCCCAGCTTCCTGGTCGAACAGACAACGATGTGAAAAATTATTGGA
ACACAAAGCTGAAGAAGAAGTTGTCGGGAATGGGAATAGATCCCGTAACCCACAAGCCTTTCTCG
CATCTAATGGCAGAGATAACCACTACACTCAATCCTCCTCAAGTCTCACACCTCGCTGAAGCTGC
CCTCGGATGTTTCAAGGACGAGATGCTTCACTTGCTCACCAAGAAACGTGTTGATCTAAACCAAA
TCAACTTCTCCAGCCCTAACCCTAACAACTTTACCCGAACCGTTGATAGCGAAGCTGGT
AAAATGAAAATGGATGGTTTGGAGAATGGTAATGGATAATGAAGCTATGGGACATGGGGAATGG
ATTCTCCTATGGATCTTCTTCGTCATCGTTTGGGAATGAAGACAAAAATGATGGAGCTGCGTCTC
CTGCGGTTGCGGCGTGGAGGGGTCACGGTGGAATACGTACAGCGGTGGCTGAAACTGCGGCAGCG
GAGGAGGAAGAGAGGAGGAAATTGAAGGGAGAAGTGGTGGACCAAGAGGAGAATGGATCTCAAGG
AGGAAGAGGAGATGGAATGTTGATGATGAGGAGCCAGCATGATCAACATCAACATCATGTGTTTA
ATGTGGACAATGTCTTGTGGGATTTACAAGCTGATGATCTCATTAATCAT
GTGGTTTGA

FIGURE 2

GRIPCCEKENVKRGQWTPEEDNKLASYIAQHGTRNWRLIPKNAGLQRCGKSCRLRWTNYLRPDLKHG
QFSDAEEHIIVKFHSVLGNRWSLIAAQLPGRTDNDVKNYWNTKLKKKLSGMGIDPVTHKPFSHLMAE
ITTTLNPPQVSHLAEAALGCFKDEMLHLLTKKRVDLNQINFSSPNHNHNPNNFNQTVDNEAGKMKLD
YGNGIMKLWDMGNGFSYGSSSSSFGNDERNEGSASPAVAAWRGHGGIRTSVAETAHEEEESFP

GGTCGGATTCCATGTTGTGAAAAGGAGAATGTGAAAAGAGGACAATGGACTCCTGAAGAAGACAACA
AATTGGCTTCTTACATTGCTCAACACGGTACTCGTAATTGGCGTCTCATCCCTAAAAACGCTGGATT
GCAGAGATGTGGGAAGAGTTGTAGACTAAGATGGACGAACTATTTGCGTCCTGACCTGAAACACGGA
CAGTTTTCTGACGCTGAAGAACATATCATTGTCAAGTTTCACTCTGTTCTTGGTAACAGGTGGTCGT
TGATTGCGGCGCAGCTTCCAGGTCGAACAGACAACGATGTGAAAAACTATTGGAACACGAAGCTGAA
GAAGAAGTTGTCGGGAATGGGGATAGATCCAGTTACTCACAAGCCTTTCTCGCACCTAATGGCAGAG
ATCACCACTACACTCAACCCTCCCCAGGTCTCTCACCTCGCTGAAGCTGCACTCGGTTGTTTCAAGG
ACGAGATGCTTCACTTGCTCACCAAGAAACGTGTTGACCTAAACCAAATCAACTTCTCAAGCCCTAA
CCATAACCATAACCCTAACAACTTTAACCAAACTGTTGATAACGAAGCTGGTAAGATGAAACTGGAT
TATGGTAATGGGATAATGAAGCTATGGGACATGGGTAATGGATTCTCGTATGGATCATCTTCCTCGT
CCTTTGGGAATGATGAAAGGAACGAGGGATCCGCGTCTCCTGCGGTTGCGGCGTGGAGGGGTCACGG
TGGAATACGTACATCAGTGGCTGAAACCGCGCACGAGGAGGAGGAAAGCTTCCCC

FIGURE 3

MGRSPCCEKDHTNKGAWTKEEDDKLISYIKAHGEGCWRSLPRSAGLQRCGKSCRLRWINY
LRPDLKRGNFTLEEDDLIIKLHSLLGNKWSLIATRLPGRTDNEIKNYWNTHVKRKLLRKG
IDPATHRPINETKTSQDSSDSSKTEDPLVKILSFGPQLEKIANFGDERIQKRVYSVVEER
CLDLNLELRISPPWQDKFHDERNLRFGRVKHRCSACRFGFGNGKECSCNNVKCQTEDSSS
SSYSSTDISSSIGYDFLGLNNTRVLDFSTLEMK

```
   1 gtttgtgtct tctagattaa tcctccaaac ttttgattaa ccaaaaaaat tatcaaacta
  61 acatgttctc cttttttctt tagaaattct aacgaattta tctttatact gatttgaata
 121 tacttaattt ggtcatttgg atgccctta caacctcctt accaaactca ctatggcaaa
 181 tatatactat tttccattgt aacataaatg tccataattt gaattaaatt cgttgcagta
 241 cgaaaccatc caactttgtc caaaaacaaa atccttataa ctatttactt taatgtaaat
 301 atatcctcta cttttgtttt tacaaccca gctcaaacaa atttattatt tgcgataaaa
 361 aatcatatcg aacaaactcg atgatttttt ttttcttacg ttattaatga aactaaaata
 421 tagaaaaaaa caagatgaac caaatttca cctatctaac tacttaaata taatatgatt
 481 aaatttggta aagtttgaaa agtttcttta gaaatgtgaa atattgatca cagtttctat
 541 tgctaaaatc accaacaaaa cgcatgtcgc cattcataat tatggtttca cacctacaac
 601 taggctaata agtaaataag tagacaacta gactcaggtt tgaaaaaacc ataaagcca
 661 tatagcgttt tctcattgaa actgcgaaca cgatcgtgtg aatgttgcag tttctagttt
 721 tgatacaaac aaacaaaaac acaatttaat cttagattaa aaagaaaaaa gagaacggag
 781 cccactagcc actccttcaa acgtgtctta ccaactctct tctagaaaca aattaggctt
 841 caccttcctc ttccaacctc tctctctctc tctctctctt tttctcaaac catctctcca
 901 taaagcccta atttcttcat cacaagaatc agaagaagaa agatgggaag gtctccttgc
 961 tgtgagaaag accacacaaa caaggagct tggactaagg aagaagacga taagctcatc
1021 tcttacatca aagctcacgg tgaaggttgt tggcgttctc ttcctagatc cgccggtctt
1081 caacgttgcg gaaaagctg tcgtctccga tggattaact atctccgacc tgatctcaag
1141 agggtaacct tcaccctcga agaagatgat ctcatcatca aactacatag ccttctcggt
1201 aacaagtgag tcacaaaaca actcctctgt tttttttac tatcctctgt tatgttaaaa
1261 agctctgttt tttaaacttt gttttttttt tcttctatca ggtggtctct tattgcgacg
1321 agattaccag gaagaacaga taacgagatt aagaattact ggaacacaca tgttaagagg
1381 aagctattaa gaaaagggat tgatccggcg actcatcgac ctatcaacga gaccaaaact
1441 tctcaagatt cgtctgattc tagtaaaaca gaggaccctc ttgtcaagat tctctctttt
1501 ggtcctcagc tggagaaaat agcaaatttc ggggacgaga gaattcaaaa gagagttgag
1561 tactcagttg ttgaagaaag atgtctggac ttgaatcttg agcttaggat cagtccacca
1621 tggcaagaca agttccatga tgagaggaac ctaaggtttg ggagagtgaa gcataggtgc
1681 agtgcgtgcc gttttggatt cgggaacggc aaggagtgta gctgtaataa tgtgaaatgt
1741 caaacagagg acagtagtag cagcagttat tcttcaaccg acattagtag tagcattggt
1801 tatgacttct tgggtctaaa caacactagg gttttggatt ttagcacttt ggaaatgaaa
1861 tgaaatgaaa tactatatta atcaatttat agctgtgaat tgtgatataa aagctattaa
1921 cagactcgtt catggttctc aactttcta
```

mgrspcceka htnkgawtke ederlisyir ahgegcwrsl pkaagllrcg kscrlrwiny
lrpdlkrgnf teeedeliik lhsllgnkws liagrlpgrt dneiknywnt hirrkllsrg
idptthrsin dpttipkvtt itfaaaheni kdidqqdemi nikaefvets kesdnneiiq
eksssclpdl nlelrispph hqqldhhrhh qrssslcftc slgiqnskdc scgsesngng
wsnnmvsmni magydflglk tnglldyrtl etk (b)

MGRSPCCEKAHTNKGAWTKEEDDRLIAYIRAHGEGCWRSLPKAAGLLRCGKSCRLRWINY
LRPDLKRGNFTEEEDELIIKLHSLLGNKWSLIAGRLPGRTDNEIKNYWNTHIRRKLLSRG
IDPATHRPLNEASQDVTTISFSGAKEEKEKINTNSNNNPIGFITKDEKKIPVQERCPDLN
LDLRISPPYYQQTQPESFKTGGRTLCPICSLGVKNSKDCTCSTITTAAGSSSSSSSHSNS
NNSSGYDFLGLKSGILEYRSLEMK

FIGURE 5

```
RWSVIAAQLP GRTDNDVKNH WNTKLKKKLS GMGIDPVTHK SFSHLMAEIA
TTLAPPQVAH LAEAALGCFK DEMLHLLTKK RPSDFPSPAV HDGAGAGASA
SALAAPCFPA APPHHPQADD TIERIKLGLS RAIMSDPSTA SAAAAAAAPS
APAEDKPWPP GDMSEGLAGM YATYNPAAHA HAQAQAEFRY DGASAAQGYV
LGGDGDQGTS MWSHQSLYSG SSGTEEARRE LPEKGNDSVG SSGGDDDAAD
DGKDSGKGAA SDMSGLFASD CVLWDLPDEL TNHMV
```

MGRSPCCEKAHTNKGAWTKEEDERLVAHIRAHGEGCWRSLPKAAGLLRCGKSCRLRWINYLR
PDLKRGNFTEEEDELIVKLHSVLGNKWSLIAGRLPGRTDNEIKNYWNTHIRRKLLSRGIDPV
THRPVTEHHASNITISPETEVAAAARDDKKGAVFRLEEEEERNKATMVVGRDRQSQSQSHSH
PAGEWGQGKRPLKCPDLNLDLCISPPCQEEEEMEEAAMRVRPAVKREAGLCFGCSLGLPRTA
DCKCSSSSFLGLRTAMLDFRSLEMK (b)

MGRSPCCEKAHTNRGAWTKEEDERLVAYIRAHGEGCWRSLPKAAGLLRCGKSCRLRWINY
LRPDLKRGNFTADEDDLIVKLHSLLGNKWSLIAARLPGRTDNEIKNYWNTHVRRKLLGRGID
PVTHRPIAADAVTVTTVSFQPSPSAAAAAAAEAEATAAKAPRCPDLNLDLCISPPCQQQEEE
EVDLKPSAAVVKREVLLGGRGHGHGHGGALCFGCSLGVQKGAPGCSCSSSNGHRCLGLRGGM
LDFRGLKMK (c)

MGRSPCCEKA HTNKGAWTKE EDDRLTAYIK AHGEGCWRSL PKAAGLLRCG KSCRLRWINY
LRPDLKRGNF SHEEDELIIK LHSLLGNKWS LIAGRLPGRT DNEIKNYWNT HIRRKLTSRG
IDPVTHRAIN SDHAASNITI SFESAQRDDK GAVFRRDAEP AKAAAAAAAI SHHVDHHHRS
NPQLDWGQGK PLKCPDLNLD LCISPPIHED PMVDTKPVVK REAGVGVGVV GLCFSCSMGL
PRSSDCKCSS FMGLRTAMLD FRSIEMK (d)

MGRSPCCEKAHTNKGAWTREEDERLVAHVRAHGEGCWRSLPSAAGLLRCGKSCRLRWINY
LRPDLKRGNFSRDEDELIVKLHSLLGNKWSLIAARLPGRTDNEIKNYWNTHIRRKLLGRG
IDPVTHRPLTDAATVSFVHPAEATKQQATEERKPPRCPDLNLDLCISLPFQQEEERPPAR
ACAKPVKMEQLQQGGICFRCSILRVRGAATECSCGSKFLGLRAGMLDFRGLEMK

FIGURE 7

```
Atmyb103    MGRIPCCEKENVKRGQWTPEEDNKLASYIAQHGTRNWRLIPKNAGLQRCGKSCRLRWTNY
p8.1.1      MGRPPCCDKSNVKKGLWTABEDAKILAYVAIHGVGNWSLIPKKAGLNRCGKSCRLRWTNY
            *** *** * *** * ** *** *  * * **  ** **** *** ****************

Atmyb103    LRPDLKHGQPSEAEEHIIVKFHSVLGNRWSLIAAQLPGRTDNDVKNYWNTKLKKKLSGMG
p8.1.1      LRPDLKHDSFSPQBEBLIIQCHRIIGSRWSSIARKLPGRTDNDVKNHWNTKLKKRLVKMG
            ******* ** ** * *  * *** **  **************  ******* * ***

Atmyb103    IDPVTHKPFSHLMAEITTTLNPPQVSHLAEAALGCPKDEMLH—LLTKKRVDLNQIN-FS
p8.1.1      IDPVTHKPVSQVLTEFR---NISGHGNSSEPFVRNFKTEPSNNSILTQSNSAWEMMRNTT
            ******** *  *  *    *       *       **  *       **

Atmyb103    NHNPNPNNPHEIADNEAGKIKMDGLDHGNGIMKLWDMGNGFSYGSSSSSFGNEERNDGSA
p8.1.1      SHESYHNSPMIFTHPTSSEFHFS--NHSN----FPLNGATSSCSSSSSSASITQPNQGAQ
             *   *          *  *  *   * *       *  * *****      * *

Atmyb103    SPAVAAWRGHGGIRTAVAETAAABEEERRKLKG--EVVDQEEIGSEG-GRGDGMTMMRNH
p8.1.1      APVTTFCWSDYLLSDPVLPLSSQTQVVGSSATSNLTFAQNENFNSQGECSSQKIASKASG
             *          *                      *           * * *

Atmyb103    HHHQHVFNVDNVLWD-----LQADDLINHMV-
p8.1.1      TCHSASSFVDEILDKDQEMLSQFPQLLNDFDY
              *    ** *           *   * *
```

FIGURE 11

```
Atmyb103  ATGGGTCGGATTCCATGTTGTGAAAAGGAGAATGTGAAGAGAGGACAATGGACTCCTGAAGAAGA
Bnmyb1    ATGGGTAGGATTCCATGCTGTGAAAAGGAGAATGTGAAGAGAGGGCAATGGACTCCTGAAGAAGA
          ***** ************ ********************** ******************

Atmyb103  CAACAAATTGGCTTCTTATATTGCTCAACATGGTACTCGTAATTGGCGTCTCATCCCTAAGAATG
Bnmyb1    CAACAAACTGGCTTCTTACATTGCTCAACATGGTACTCGTAATTGGCGTCTCATCCCTAAAAACG
          ******* ********** ********************************** ** *

Atmyb103  CTGGGTTGCAAAGATGTGGGAAGAGTTGTAGGCTGCGATGGACAAACTATCTGCGTCCGGATTTG
Bnmyb1    CTGGATTGCAGAGATGTGGAAAGAGTTGTAGACTACGGTGGACAAACTATTTGCGTCCTGACCTG
          **** ***** ******** *********** ** ** ********** ****** ** **

Atmyb103  AAACATGGCCAGTTCTCGGAGGCTGAAGAACATATCATTGTCAAGTTTCACTCTGTTCTTGGTAA
Bnmyb1    AAACATGGTCAATTTTCTGAGGCTGAAGAACATATCATCGTCAAGTTTCACTCTGTTCTTGGTAA
          ******** ** ** ** ******************** *************************

Atmyb103  CCGGTGGTCGTTGATTGCGGCGCAACTTCCTGGTCGGACAGACAACGATGTGAAAAATTATTGGA
Bnmyb1    CCGGTGGTCGTTGATTGCGGCCCAGCTTCCTGGTCGAACAGACAACGATGTGAAAAATTATTGGA
          ********************* ** *********** ***************************

Atmyb103  ACACGAAGCTGAAGAAGAAGTTGTCAGGAATGGGAATAGATCCGGTGACCCACAAGCCTTTCTCG
Bnmyb1    ACACAAAGCTGAAGAAGAAGTTGTCGGGAATGGGAATAGATCCCGTAACCCACAAGCCTTTCTCG
          **** ******************** ***************** ** *****************

Atmyb103  CATCTAATGGCAGAGATCACCACTACACTTAATCCTCCTCAGGTTTCTCACCTAGCCGAAGCTGC
Bnmyb1    CATCTAATGGCAGAGATAACCACTACACTCAATCCTCCTCAAGTCTCACACCTCGCTGAAGCTGC
          ***************** *********** *********** ** ** ** ** ** *******

Atmyb103  CCTCGGCTGTTTCAAGGACGAGATGCTTCACTTGCTCACCAAGAAACGTGTTGACCTAAACCAAA
Bnmyb1    CCTCGGATGTTTCAAGGACGAGATGCTTCACTTGCTCACCAAGAAACGTGTTGATCTAAACCAAA
          ****** *********************************************** *********

Atmyb103  TCAACTTTTCAAACCATAACCCTAACCCAAACAACTTTCACGAGATTGCTGATAATGAAGCTGGT
Bnmyb1    TCAACTTCTC-----CAGCCCTAACCCTAACAACTTTACCCGAACCGTTGATAGCGAAGCTGGT
          ******* **      * *********** ********* *  * ***** ** ********

Atmyb103  AAGATAAAGATGGATGGTTTGGACCATGGGAATGGGATAATGAAGTTATGGGACATGGGTAATGG
Bnmyb1    AAAATGAAAATGGATGGTTTGGAGAATGGTAATGGGATAATGAAGCTATGGGACATGGGGAATGG
          ** ** ** ************** *** *************** ************ ****

Atmyb103  ATTCTCATATGGATCCTCTTCGTCTTCGTTTGGGAATGAAGAAAGAAATGATGGATCAGCGTCTC
Bnmyb1    ATTCTCCTATGGATCTTCTTCGTCATCGTTTGGGAATGAAGACAAAAAATGATGGAGCTGCGTCTC
          ****** ******** ******** ***************** * ********* * ******

Atmyb103  CTGCCGTTGCAGCTTGGAGGGGTCACGGAGGAATACGTACCGCGGTAGCTGAAACCGCGGCAGCG
Bnmyb1    CTGCGGTTGCGGCGTGGAGGGGTCACGGTGGAATACGTACAGCGGTGGCTGAAACTGCGGCAGCG
          **** ***** ** ************* ************ **** ******** *********

Atmyb103  GAGGAGGAGGAGAGAAGGAAGCTGAAGGGAGAAGTGGTTGATCAAGAGGAGATTGGATCTGAAGG
Bnmyb1    GAGGAGGAAGAGAGGAGGAAATTGAAGGGAGAAGTGGTGGACCAAGAGGAGAATGGATCTCAAGG
          ******** ***** ****   ************** ** ** ********** ****** ****

Atmyb103  AGGAAGAGGAGATGGAATGACGATGATGAGGAACCATCAT------CATCATCAACATGTGTTTA
Bnmyb1    AGGAAGAGGAGATGGAATGTTGATGATGAGGAGCCAGCATGATCAACATCAACATCATGTGTTTA
          ******************* ************ *** ***       **** ** *********

Atmyb103  ATGTGGATAATGTCTTGTGGGATTTACAAGCTGATGATCTCATCAATCAT
Bnmyb1    ATGTGGACAATGTCTTGTGGGATTTACAAGCTGATGATCTCATTAATCAT
          ******* *********************************** *****

Atmyb103  ATGGTTTGA
Bnmyb1    GTGGTTTGA
          *******
```

FIGURE 12

```
MGRIPCCEKE NVKRGQWTPE EDNKLASYIA QHGTRNWRLI PKNAGLQRCG
KSCRLRWTNY LRPDLKHGQF SEAEEHIIVK FHSVLGNRWS LIAAQLPGRT
DNDVKNYWNT KLKKKLSGMG IDPVTHKPFS HLMAEITTTL NPPQVSHLAE
AALGCFKDEM LHLLTKKRVD LNQINFSSPN PNNFTRTVDS EAGKMKMDGL
ENGNGIMKLW DMGNGFSYGS SSSSFGNEDK NDGAASPAVA AWRGHGGIRT
AVAETAAAEE EERRKLKGEV VDQEENGSQG GRGDGMLMMR SQHDQHQHHV
FNVDNVLWDL QADDLINHVV
```

FIGURE 13

```
Atmyb103  MGRIPCCEKENVKRGQWTPBEDNKLASYIAQHGTRNWRLIPKNAGLQRCGKSCRLRWTNY
Bnmyb1    MGRIPCCEKENVKRGQWTPBEDNKLASYIAQHGTRNWRLIPKNAGLQRCGKSCRLRWTNY
          ************************************************************

Atmyb103  LRPDLKHGQFSEAEEHIIVKFHSVLGNRWSLIAAQLPGRTDNDVKNYWNTKLKKKLSGMG
Bnmyb1    LRPDLKHGQFSEAEEHIIVKFHSVLGNRWSLIAAQLPGRTDNDVKNYWNTKLKKKLSGMG
          ************************************************************

Atmyb103  IDPVTHKPFSHLMABITTTLNPPQVSHLAEAALGCFKDEMLHLLTKKRVDLNQINFSNHN
Bnmyb1    IDPVTHKPFSHLMABITTTLNPPQVSHLAEAALGCFKDEMLHLLTKKRVDLNQINFS--S
          ********************************************************  .

Atmyb103  PNPNNFHEIADNEAGKIKMDGLDHGNGIMKLWDMGNGFSYGSSSSSFGNEERNDGSASPA
Bnmyb1    PNPNNFTRTVDSEAGKMKMDGLENGNGIMKLWDMGNGFSYGSSSSSFGNEDKNDGAASPA
          ******  *  *** ***** * *****************:***:***:****

Atmyb103  VAAWRGHGGIRTAVAETAAAEEEERRKLKGEVVDQEEIGSEGGRGDGMTMMRNHH--HHQ
Bnmyb1    VAAWRGHGGIRTAVAETAAAEEEERRKLKGEVVDQEENGSQGGRGDGMLMMRSQHDQHQH
          *************************************:******* ***.:*  *::

Atmyb103  HVPNVDNVLWDLQADDLINHMV
Bnmyb1    HVPNVDNVLWDLQADDLINHVV
          ********************:*
```

FIGURE 14

```
Atmyb103    MGRIPCCEKENVKRGQWTPEEDNKLASYIAQHGTRNWRLIPKNAGLQRCGKSCRLRWTNY
p700-1      MGRIPCCEKENVKRGQWTPEEDNKLASYIAQHGTRNWRLIPKNAGLQRCGKSCRLRWTNY
            ************************************************************

Atmyb103    LRPDLKHGQFSEAEEHIIVKFHSVLGNRWSLIAAQLPGRTDNDVKNYWNTKLKKKLSGMG
p700-1      LRPDLKHGQFSDAEEHIIVKFHSVLGNRWSLIAAQLPGRTDNDVKNYWNTKLKKKLSGMG
            ***********:************************************************

Atmyb103    IDPVTHKPFSHLMAEITTTLNPPQVSHLAEAALGCFKDEMLHLLTKKRVDLNQINFS--N
p700-1      IDPVTHKPFSHLMAEITTTLNPPQVSHLAEAALGCFKDEMLHLLTKKRVDLNQINFSSPN
            ********************************************************  *

Atmyb103    HNPNPNNFHEIADNEAGKIKMDGLDHGNGIMKLWDMGNGPSYGSSSSSFGNEERNDGSAS
p700-1      HNHNPNNFNQTVDNEAGKMKLD---YGNGIMKLWDMGNGFSYGSSSSSFGNDERNEGSAS
            ** *****::  ******:*:*    :************************: ***:****

Atmyb103    PAVAAWRGHGGIRTAVAETAAAEEEERRKLKGEVVDQEEIGSEGGRGDGMTMMRNHHHHQ
p700-1      PAVAAWRGHGGIRTSVAETAHEEEESFP--------------------------------
            **************:***** ****  ***.

Atmyb103    HVFNVDNVLWDLQADDLINHMV
p700-1      ----------------------
```

FIGURE 16

```
Atmyb103   MGRIPCCEKENVKRGQWTPEEDNKLASYIAQHGTRNWRLIPKNAGLQRCGKSCRLRWTNY
p800-19    ------------------------------------------------------------Y
                                                                      *

Atmyb103   LRPDLKHGQFSEAEEHIIVKFHSVLGNRWSLIAAQLPGRTDNDVKNYWNTKLKKKLSGMG
p800-19    LRPDLKHGQFSEAEEHIIVKFHSVLGNRWSLIAAQLPGRTDNDVKNYWNTKLKKKLSGMG
           ************************************************************

Atmyb103   IDPVTHKPFSHLMAEITTTLNPPQVSHLAEAALGCFKDEMLHLLTKKRVDLNQINFSNHN
p800-19    IDPVTHKPFSHLMAEITTTLNPPQVSHLAEAALGCFKDEMLHLLTKKRVDLNQINFS--S
           ********************************************************  .

Atmyb103   PNPNNPHEIADNEAGKIKMDGLDHGNGIMKLWDMGNGFSYGSSSSSFGNEERNDGSASPA
p800-19    PNPNNPTRTVDSEAGKMKMDGLENGNGIMKLWDMGNGFSYGSSSSSFGNEDKNDGAASPA
           ******  * **** ***** *******************:***:****

Atmyb103   VAAWRGHGGIRTAVAETAAAEEEERRKLKGEVVDQEEIGSEGGRGDGMTMMRNHH--HHQ
p800-19    VAAWRGHGGIRTAVAETAAAEEEERRKLKGEVVDQEENGSQGGRGDGMLMMRSQHDQHQH
           ************************************* ***:******* ***.:*   *::

Atmyb103   HVFNVDNVLWDLQADDLINHMV
p800-19    HVFNADNVLWDLQADDLINHVV
           ****.***************:*
```

Figure 18

```
Atmyb103   MGRIPCCEKENVKRGQWTPEEDNKLASYIAQHGTRNWRLIPKNAGLQRCGKSCRLRWTNY
p900-10    MGRIPCCEKENVKRGQWTPEEDNKLASYIAQHGTRNWRLIPKNAGLQRCGKSCRLRWTNY
           ************************************************************

Atmyb103   LRPDLKHGQFSEAEEHIIVKFHSVLGNRWSLIAAQLPGRTDNDVKNYWNTKLKKKLSGMG
p900-10    LRPDLKHGQFSDAEEHIIVKFHSVLGNRWSLIAAQLLGRTDNDVKNYWNTKLKKKLSGMG
           ***********:*********************** ***********************

Atmyb103   IDPVTHKPFSHLMAEITTTLNPPQVSHLAEAALGCPKDEMLHLLTKKRVDLNQINFS--N
p900-10    KDPVTHKPFSHLMAEITTTLNPPQVSHLAEAALGCPKDEMLHLLTKKRVDLNQINFSSPN
            *********************************************************  *

Atmyb103   HNPNPNNPHEIADNEAGKIKMDGLDHGNGIMKLWDMGNGFSYGSSSSSFGNEERNDGSAS
p900-10    HNHNPNNPNQTVDNEAGKMKLD---YGNGIMKLWDMGNGFSYGSSSSSFGNDERNEGSAS
           ** *****:: .******:*:*   :*********************************:***:****

Atmyb103   PAVAAWRGHGGIRTAVAETAAAEEEERRKLKGEVVDQEEIGSEGGRGDGMTMMRNH-HHH
p900-10    PAVAAWRGHGGIRTSVAETAAVEEEERRKLKGEVMEQEEIGSEGGRGDGMTMRRQHDQHQ
           **************.******.************;;*************** *;* ;*;

Atmyb103   QHVFNVDNVLWDLQADDLINHMV
p900-10    QHAFNVDNDLWDLQADDLINHMV
           **.***** **************
```

FIGURE 20

```
p900-10    MGRIPCCEKENVKRGQWTPEEDNKLASYIAQHGTRNWRLIPKNAGLQRCGKSCRLRWTNY
p700-1     MGRIPCCEKENVKRGQWTPEEDNKLASYIAQHGTRNWRLIPKNAGLQRCGKSCRLRWTNY
Atmyb103   MGRIPCCEKENVKRGQWTPEEDNKLASYIAQHGTRNWRLIPKNAGLQRCGKSCRLRWTNY
p800-19                                                               Y
Bnmyb1     MGRIPCCEKENVKRGQWTPEEDNKLASYIAQHGTRNWRLIPKNAGLQRCGKSCRLRWTNY
           ************************************************************ p900-10    LRPDLKHGQFSDAEEHIIVKFHSVLGNRWSLIAAQLEGRTDNDVKNYWNTKLKKKLSGMG
p700-1     LRPDLKHGQFSDAEEHIIVKFHSVLGNRWSLIAAQLEGRTDNDVKNYWNTKLKKKLSGMG
Atmyb103   LRPDLKHGQFSEAEEHIIVKFHSVLGNRWSLIAAQLEGRTDNDVKNYWNTKLKKKLSGMG
p800-19    LRPDLKHGQFSEAEEHIIVKFHSVLGNRWSLIAAQLEGRTDNDVKNYWNTKLKKKLSGMG
Bnmyb1     LRPDLKHGQFSEAEEHIIVKFHSVLGNRWSLIAAQLEGRTDNDVKNYWNTKLKKKLSGMG
           *********:*************************** ************** p900-10    KDPVTHKPFSHLMAEITTTLNPPQVSHLAEAALGCFKDEMLHLLTKKRVDLNQINFSSPN
p700-1     IDPVTHKPFSHLMAEITTTLNPPQVSHLAEAALGCFKDEMLHLLTKKRVDLNQINFSSPN
Atmyb103   IDPVTHKPFSHLMAEITTTLNPPQVSHLAEAALGCFKDEMLHLLTKKRVDLNQINFSS N
p800-19    IDPVTHKPFSHLMAEITTTLNPPQVSHLAEAALGCFKDEMLHLLTKKRVDLNQINFSSPN
Bnmyb1     IDPVTHKPFSHLMAEITTTLNPPQVSHLAEAALGCFKDEMLHLLTKKRVDLNQINFSSPN
            *********************************************************** * p900-10    HNHNPNNFNQTVDNEAGKMKLD---VGNGIMKLWDMGNGPSYGSSSSSFGNDERNEGSAS
p700-1     HNHNPNNFNQTVDNEAGKMKLD---YGNGIMKLWDMGNGPSYGSSSSSFGNDERNEGSAS
Atmyb103   HNPNPNNFHELADNEAGKEKMDGLDHGNGIMKLWDMGNGPSYGSSSSSFGNEERNDGAAS
p800-19    ------PNNFTRTVDSEAGKMKMDGLENGNGIMKLWDMGNGPSYGSSSSSFGNEDKNDGAAS
Bnmyb1     ------PNNFTRTVDSEAGKMKMDGLENGNGIMKLWDMGNGPSYGSSSSSFGNEDKNDGAAS
                .****  .*.****.*:.*  ********************::: *:*;**

p900-10    PAVAAWRGHGGIRTSVAETAEVEEEERRKLKGEVMEQEEIGSEGGRGDGMTMRRQHDQH
p700-1     PAVAAWRGHGGIRTSVAETAHEEEE
Atmyb103   PAVAAWRGHGGIRTAVAETAAAEEEERRKLKGEVVDQEEIGSEGGRGDGMTMRNHH H
p800-19    PAVAAWRGHGGIRTAVAETAAAEEEERRKLKGEVVEQEENGSQGGRGDGMLMMRSQHDQH
Bnmyb1     PAVAAWRGHGGIRTAVAETAAAEEEERRKLKGEVVDQEENGSQGGRGDGMLMMRSQHDQH
           ************:*** * ***********  *  ************ p900-10    QQHAFNVDNDLWDLQADDLINHMV
p700-1
Atmyb103   HQHMFNVDNVLWDLQADDLINHMV
p800-19    QHHVFNADNVLWDLQADDLINHMV
Bnmyb1     QHHVFNVDNVLWDLQADDLINHMV
            * ** *************** *
```

FIGURE 21

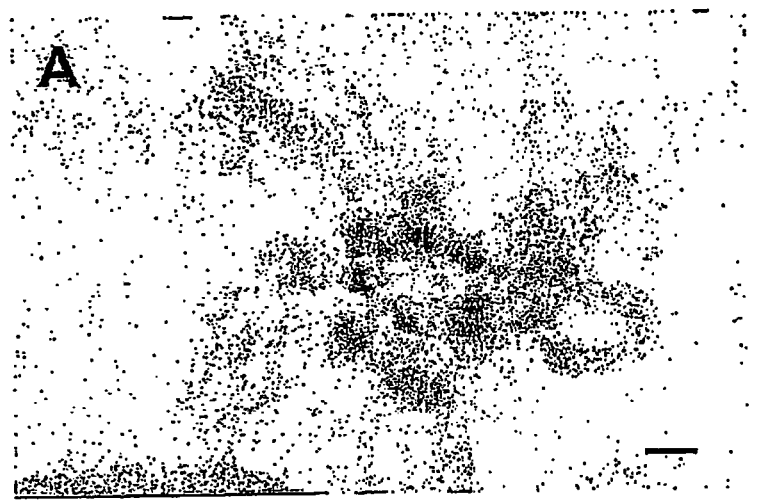
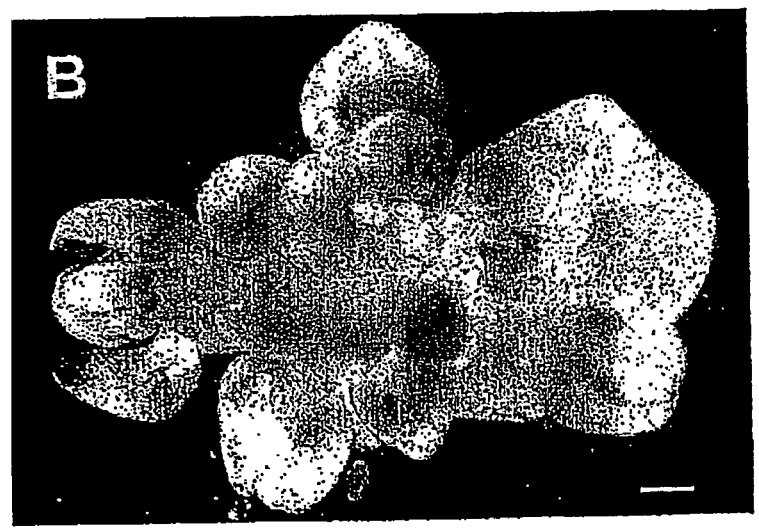
FIGURE 22

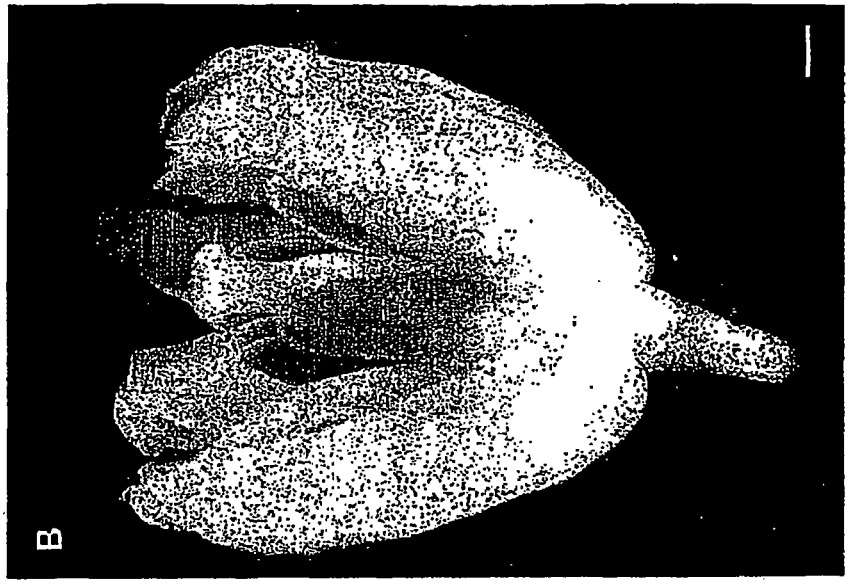
FIGURE 28

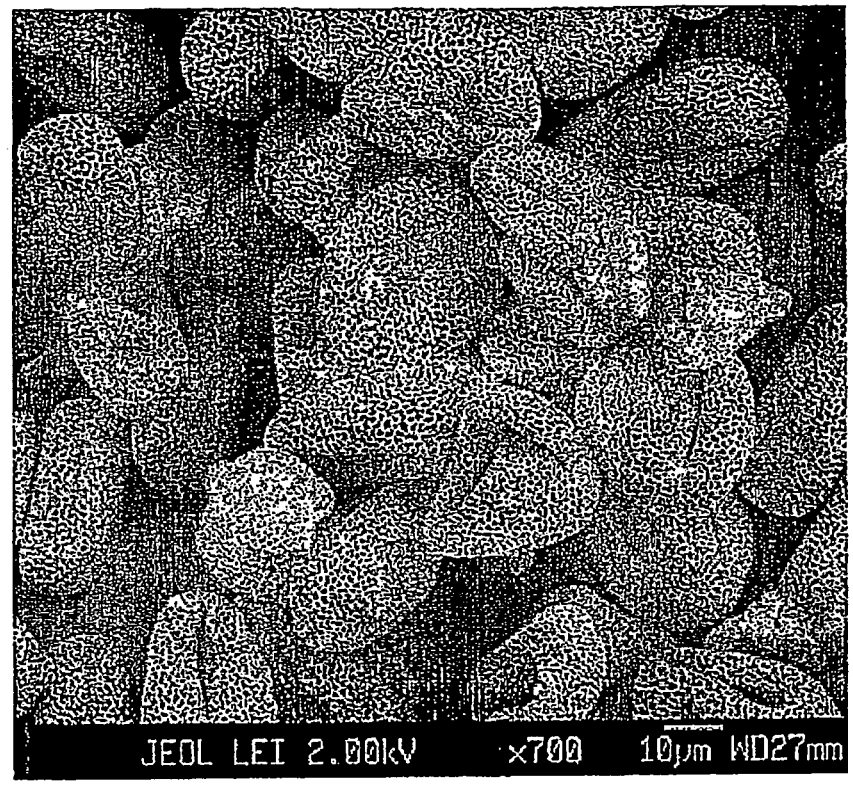
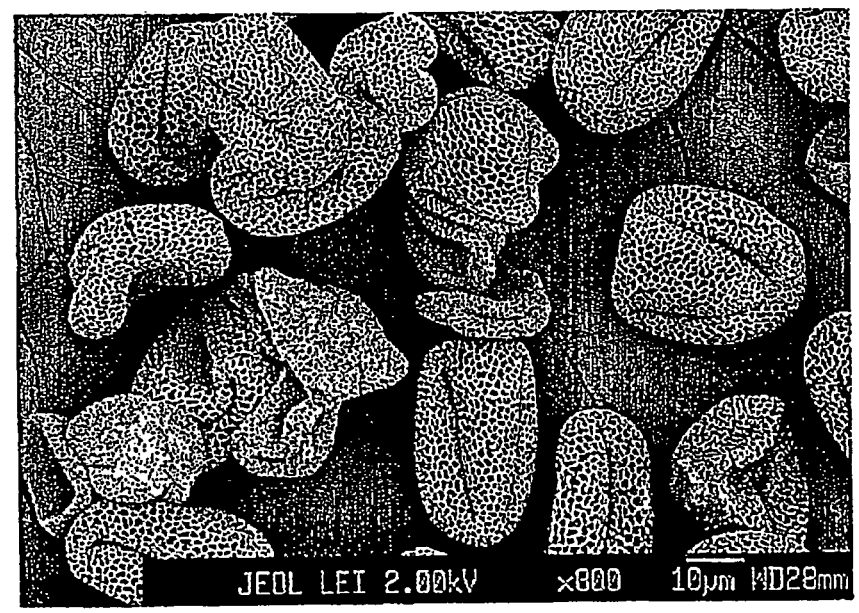
FIGURE 32b

```
AGTCATCGGCGGCGGCAGACCATCTACAGAGATAGTGAGATGGGGAGGTCGCCGTGCTGC
GAGAAGGCGCACACCAACAAGGGCGCCTGGACCAAGGAGGAGGACGACCGGCTCACCGCC
TACATCAAGGCGCACGGCGAGGGCTGCTGGCGCTCCCTGCCCAAGGCCGCGGGGTTGCTC
CGCTGCGGCAAGAGCTGCCGCCTCCGCTGGATCAACTACCTCCGCCCCGACCTCAAGCGC
GGCAACTTCAGCGATGAGGAGGACGAGCTCATCATCAAGCTCCACAGCCTCCTGGGCAAC
AAATGGTCTCTGATAGCCGGGAGACTCCCAGGGAGGACGGACAACGAGATCAAGAACTAC
TGGAACACGCACATCAGGAGGAAGCTCACGAGCCGGGGGATCGACCCGGTGACCCACCGC
GCGATCAACAGCGACCACGCCGCGTCCAACATCACCATATCCTTCGAGACGGCGCAGAGG
GACGACAAGGGCGCCGTGTTCCGGCGAGACGCCGAGCCCACCAAGGTAGCGGCAGCGGCA
GCGGCGATCACCCACGTGGACCACCATCACCATCACCGTAGCAACCCCCTCCACCAGATG
GAGTGGGGCCAGGGGAAGCCGCTCAAGTGCCCGGACCTGAACCTGGACCTCTGCATCAGC
CCCCCGTCCCACGAGGACCCCATGGTGGACACCAAGCCCGTGGTGAAGAGGGAGGCCGTC
GTGGGCCTCTGCTTCAGCTGCAGCATGGGGCTCCCCAGGAGCGCGGACTGCAAGTGCAGC
AGCTTCATGGGGCTCCGGACCGCCATGCTCGACTTCAGAAGCATCGAGATGAAATGAGCA
GAGCAGAGC
```

AtMYB32   MGRSPCCEKDHTNKGAWTKEEDDKLISYIKAHGEGCWRSLPRSA
TaMYB32   MGRSPCCEKAHTNKGAWTKEEDDRLTAYIKAHGEGCWRSLPKAA

AtMYB32   GLQRCGKSCRLRWINYLRPDLKRGNFTLEEDDLIIKLHSLLGNK
TaMYB32   GLLRCGKSCRLRWINYLRPDLKRGNFSDEEDELIIKLHSLLGNK

AtMYB32   WSLIATRLPGRTDNEIKNYWNTHVKRKLLRKGIDPATHRPINET
TaMYB32   WSLIAGRLPGRTDNEIKNYWNTHIRRKLTSRGIDPVTHRAINSD

AtMYB32   KTSQDSSDSSKTEDPLVKILSFGPQLEKIANFGDERIQKRVE--
TaMYB32   HAASNITISFETAQRDDKGAVFRRDAEPTKVAAAAAITHVDHH

AtMYB32   -------------YSVVEERCLDLNLELRISPP-WQDKFHDER-
TaMYB32   HHHRSNPLHQMEWGQGKPLKCPDLNLDLCISPPSHEDPMVDTKP

AtMYB32   NLRFGRVKHRCSACRFGFGNGKECSCNNVKCQTEDSSSSSYSST
TaMYB32   VVKREAVVGLCFSCSMGLPRSADCKC------------------

AtMYB32   DISSSIGYDFLGLNNTRVLDFSTLEMK
TaMYB32   ---SS----FMGLR-TAMLDFRSIEMK

FIGURE 36

```
AtMYB103    61
LRPDLKHGQFSEAEEHIIVKFHSVLGNRWSLIAAQLPGRTDNDVKNYWNTKLKKKLSGMG 120
LRPDLKHG+F++AEE  I+K HSV+GNRWS+IAAQLPGRTDNDVKN+WNTKLKKKLSGMG ..

OsMYB103    61
LRPDLKHGEFTDAEEQTIIKLESVVGNRWSVIAAQLPGRTDNDVKNHWNTKLKKKLSGMG 120
                     R2                        Tr-R2
AtMYB103   121  IDPVTHKPFSHLMAEITTTLNPPQVSHLAEAALGCFKDEMLHLLTKKR 168
                IDPVTHK FSHLMAEI TTL PPQV+HLAEAALGCFKDEMLHLLTKKR

OsMYB103   121  IDPVTHKSFSHLMAEIATTLAPPQVAHLAEAALGCFKDEMLHLLTKKR 168

AtMYB103   306  VLWDLQADDLINHMV 320
                VLWDL  D+L NHMV

OsMYB103   359  VLWDLP-DELTNHMV 372
```

FIGURE 37

```
ATGGGGCGGG TGCCGTGCTG CGAGAAGGAC AACGTGAAGC GCGGGCAGTG GACGCCCGAG
 M  G  R    V  P  C  C   E  K  D    N  V  K    R  G  Q  W   T  P  E
GAGGACAACA AGCTGCTCTC CTACATCACC CAGTACGGCA CCCGCAACTG GCGCCTCATC
 E  D  N    K  L  L  S   Y  I  T   Q  Y  G    T  R  N  W    R  L  I
CCCAAGAACG CCGgtacgtt ggcgcgcgcg ccgccaccgg cgaacgcgtg gttgcagcag
 P  K  N  A
cggcggcgct ctgaccgggg tgtttgttgc tggaacgttg gcagGGTTGC AGCGGTGCGG
                                                 G  L   Q  R  C  G
GAAGAGCTGC CGGCTGCGGT GGACCAACTA CCTCCGGCCC GACCTCAAGC ACGGCGAGTT
 K  S  C    R  L  R   W  T  N  Y   L  R  P   D  L  K    H  G  E  F
CACCGACGCC GAGGAGCAGA CCATCATCAA GCTCCACTCC GTCGTCGGCA ACAGgtaggc
 T  D  A    E  E  Q    T  I  I  K   L  H  S   V  V  G   N  R
atcaacgagt ggtctcgcta caccgtcttg tgatcttggg tcatttttgg aggaatgtat
tgagcaatgc gggatggggc tgtgtgtggc aagGTGGTCG GTGATCGCGG CGCAGCTTCC
                                     W  S    V  I  A    A  Q  L  P
GGGGCGGACG GACAACGACG TGAAGAACCA CTGGAACACG AAGCTGAAGA AGAAGCTGTC
 G  R  T    D  N  D   V  K  N  H   W  N  T    K  L  K   K  K  L  S
CGGGATGGGC ATCGACCCCG TCACGCACAA GTCCTTCTCG CACCTCATGG CCGAGATCGC
 G  M  G    I  D  P   V  T  H  K   S  F  S    H  L  M   A  E  I  A
CACCACGCTG GCGCCGCCGC AGGTGGCGCA CCTCGCCGAG GCCGCGCTGG GGTGCTTCAA
 T  T  L    A  P  P   Q  V  A  H   L  A  E    A  A  L   G  C  F  K
GGACGAGATG CTCCACCTCC TCACCAAGAA GCGCCCCTCC GACTTCCCCT CGCCCGCCGT
 D  E  M    L  H  L   L  T  K  K   R  P  S    D  F  P   S  P  A  V
GCACGACGGC GCCGGCGCCG GCGCCAGCGC GTCCGCGCTC GCCGCGCCCT GTTTCCCCGC
 H  D  G    A  G  A   G  A  S  A   S  A  L    A  A  P   C  F  P  A
CGCGCCGCCG CACCACCCGC AGGCCGACGA CACCATCGAG CGCATCAAGC TCGGCCTGTC
 A  P  P    H  H  P   Q  A  D  D   T  I  E    R  I  K   L  G  L  S
CCGCGCCATC ATGAGCGATC CCTCCACCGC CTCCGCCGCC GCCGCCGCCG CCGCGCCCTC
 R  A  I    M  S  D   P  S  T  A   S  A  A    A  A  A   A  A  P  S
CGCCCCCGCG GAGGACAAGC CGTGGCCGCC CGGCGACATG TCCGAGGGGC TCGCCGGGAT
 A  P  A    E  D  K   P  W  P  P   G  D  M    S  E  G   L  A  G  M
GTACGCCACG TACAACCCGG CGGCGCACGC GCACGCGCAG GCCCAGGCCG AGTTCCGGTA
 Y  A  T    Y  N  P   A  A  H  A   H  A  Q    A  Q  A   E  F  R  Y
CGACGGGGCC TCCGCGGCGC AGGGCTACGT CCTCGGCGGC GACGGCGACC AGGGCACGTC
 D  G  A    S  A  A   Q  G  Y  V   L  G  G    D  G  D   Q  G  T  S
GATGTGGAGC CACCAGAGCC TGTACAGCGG GAGCTCCGGC ACCGAGGAGG CCAGGCGGGA
 M  W  S    H  Q  S   L  Y  S  G   S  S  G    T  E  E   A  R  R  E
GTTGCCGGAG AAGGGCAACG ACAGCGTCGG CAGCAGCGGC GGCGACGACG ACGCCGCGGA
 L  P  E    K  G  N   D  S  V  G   S  S  G    G  D  D   D  A  A  D
CGACGGCAAG GACAGCGGGA AGGGGGCAGC CTCCGACATG TCGGGCCTGT TCGCCTCCGA
 D  G  K    D  S  G   K  G  A  A   S  D  M    S  G  L   F  A  S  D
CTGCGTGCTC TGGGACTTGC CCGACGAGCT CACGAATCAC ATGGTGTAG
 C  V  L    W  D  L   P  D  E  L   T  N  H    M  V
```

AtMYB103      1
MGRIPCCEKENVKRGQWTPEEDNKLASYIAQHGTRNWRLIPKNAGLQRCGKSCRLRWTNY 60
MGR+PCCEK+NVKRGQWTPEEDNKL SYI Q+GTRNWRLIPKNAGLQRCGKSCRLRWTNY

OsMYB103      1
MGRVPCCEKDNVKRGQWTPEEDNKLLSYITQYGTRNWRLIPKNAGLQRCGKSCRLRWTNY 60
                            R1                Tr-F1

FIGURE 37 (Cont)

ACCGACAACGATGTCAAG
AACCACTGGAACACCAAG
CTCAAGAAGAAGCTGTCC
GGGATGGGCATCGACCCC
GTCACGCACAAGTCCTTC
TCGCACCTCATGGCCGAG
ATCGCCACCACGCTCGCC
CCGCCGCAGGTGGCGCAC
CTCGCCGAGGCCGCCCTG
GGGTGCTTCAAAGACGAG
ATGCT

AtMYB103
TDNDVKNYWNTKLKKKLSGMGIDPVTHKPFSHLMAEITTTLNPPQVSHLAEAALGCFK
TaMYB103
TDNDVKNHWNTKLKKKLSGMGIDPVTHKSFSHLMAEIATTLAPPQVAHLAEAALGCFK

AtMYB103   DEMLHLLTKKR
TaMYB103   DEMLHLLTKKR

FIGURE 38

Figure 42 (part 1)
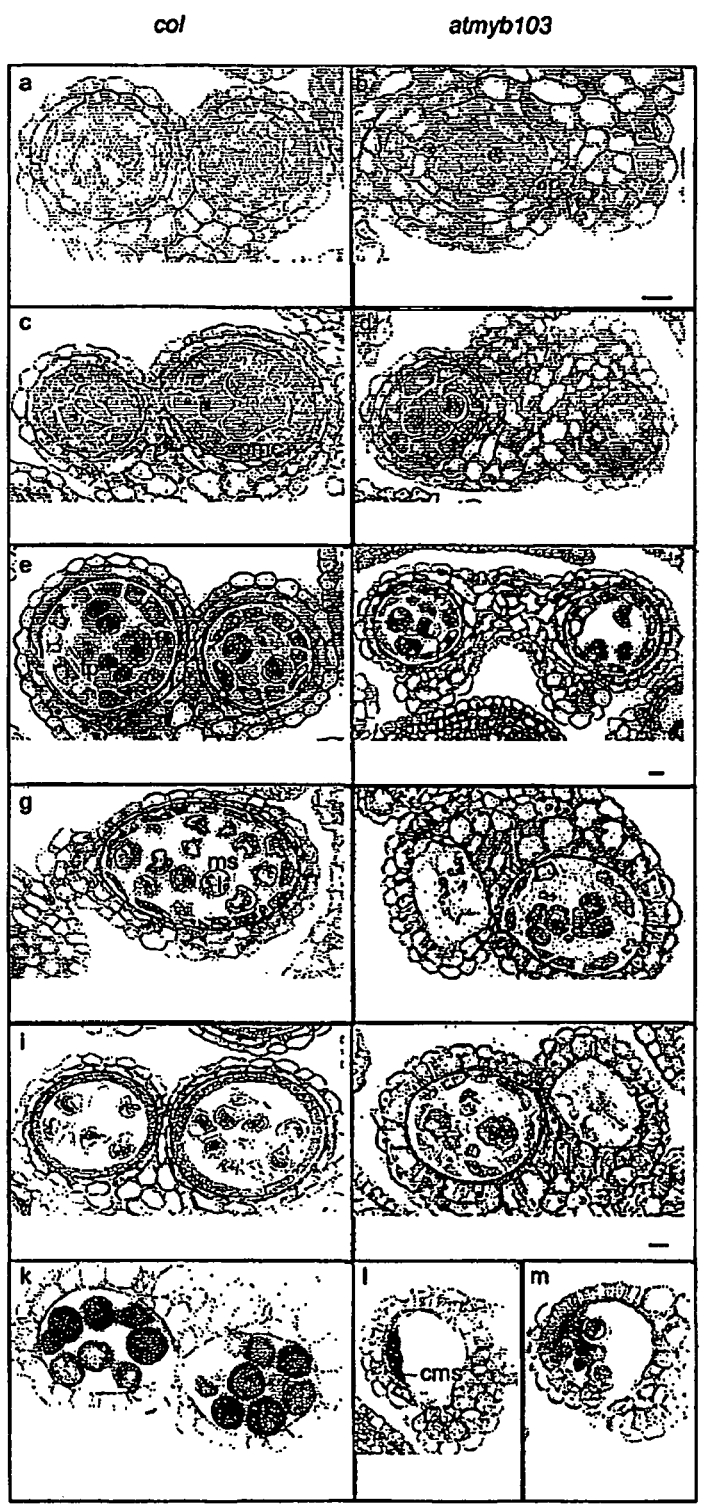

Figure 42 (part2)
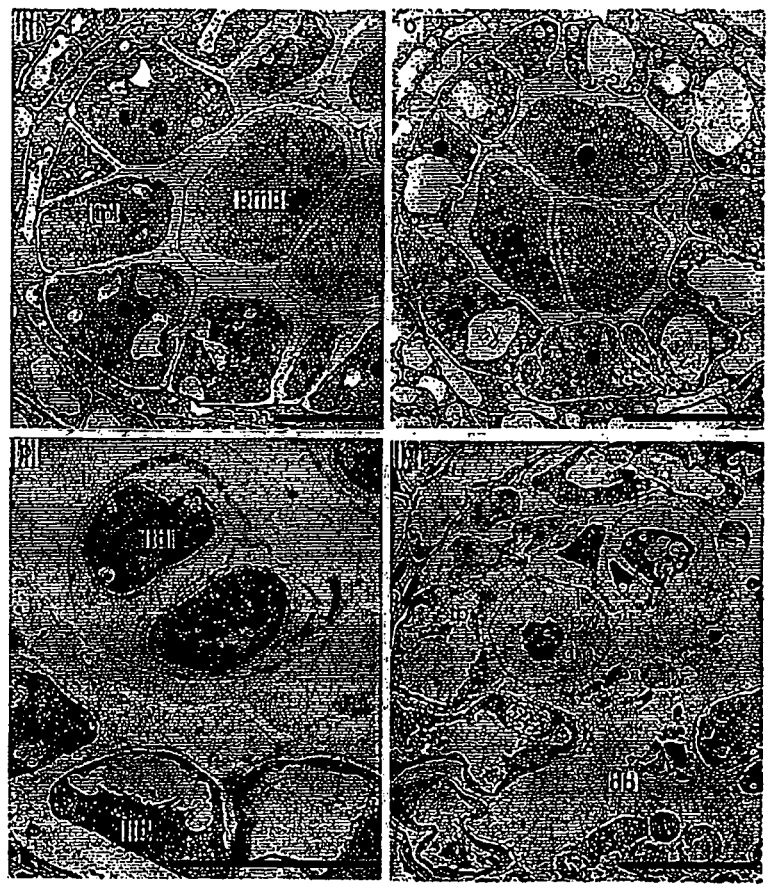

Figure 43
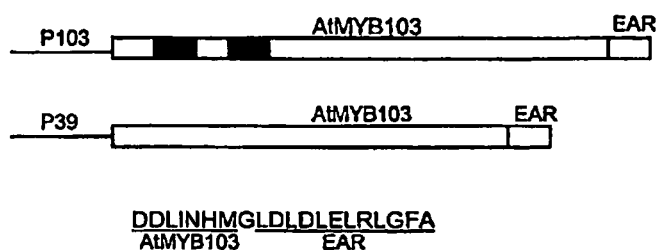
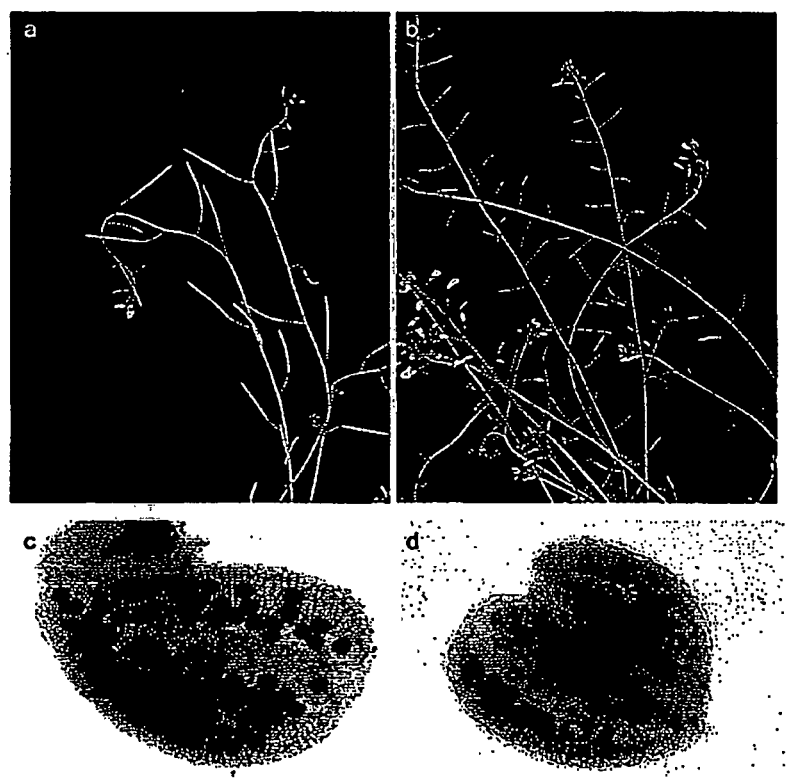

Figure 48
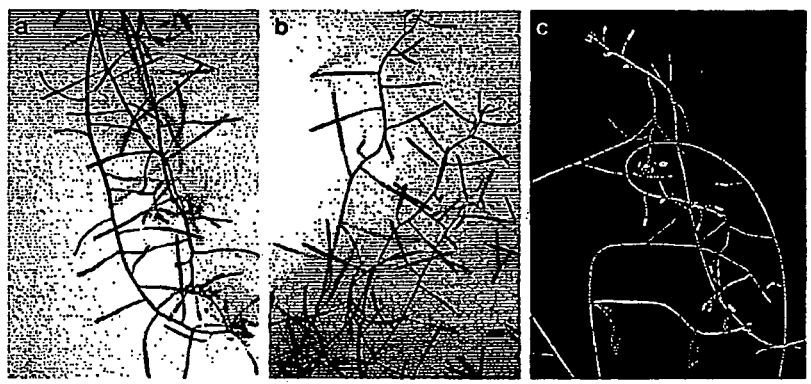
A
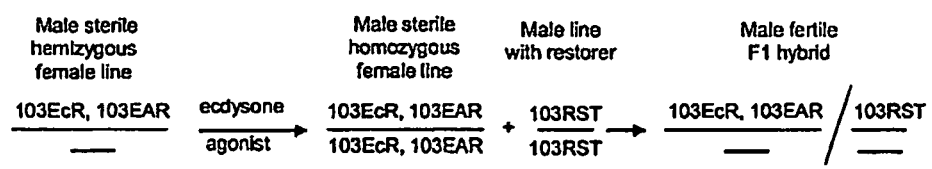

Figure 49
A
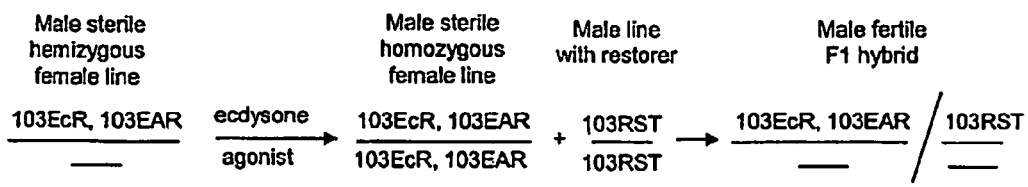
B
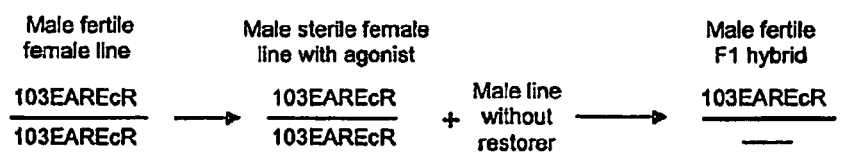

SEQUENCE LISTING

<160> NUMBER OF SEQ ID NOS: 50

<210> SEQ ID NO 1
<211> LENGTH: 270
<212> TYPE: PRT
<213> ORGANISM: Brassica napus

<400> SEQUENCE: 1

```
Met Gly Arg Ser Pro Cys Cys Glu Lys Asp His Thr Asn Lys Gly Ala
1               5                   10                  15

Trp Thr Lys Glu Glu Asp Lys Leu Val Ser Tyr Ile Lys Ser His
            20                  25                  30

Gly Glu Gly Cys Trp Arg Ser Leu Pro Arg Ser Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr Leu Glu Glu Asp Leu Ile Ile Lys
65                  70                  75                  80

Leu His Ser Leu Leu Gly Asn Lys Trp Ser Leu Ile Ala Thr Arg Leu
                85                  90                  95

Pro Gly Arg Thr Asp Asn Glu Ile Lys Asn Tyr Trp Asn Thr His Val
            100                 105                 110

Lys Arg Lys Leu Leu Arg Gly Gly Ile Asp Pro Thr Thr His Arg Pro
        115                 120                 125

Ile Asn Glu Ala Lys Ala Pro Arg Asp Ser Ser Glu Thr Arg Glu Thr
    130                 135                 140

Glu Asp Ser Leu Val Lys Phe Leu Ser Phe Ser Arg Gln Leu Glu Lys
145                 150                 155                 160

Lys Glu Ser Phe Gly Glu Glu Arg Asn Asp Gln Lys Gly Leu Ile Cys
                165                 170                 175

Lys Lys Glu Arg Val Glu Tyr Ser Ile Val Glu Glu Lys Cys Leu Asp
            180                 185                 190

Leu Asn Leu Glu Leu Arg Ile Ser Pro Pro Trp Gln Asp Gln Gln His
        195                 200                 205

His Asp Glu Thr Lys Leu Trp Phe Gly Lys Gly Lys Tyr Met Cys Thr
    210                 215                 220

Ala Cys Arg Phe Gly Leu Gly Asn Gly Lys Lys Cys Ser Cys Asp Asn
225                 230                 235                 240

Val Lys Cys Gln Val Glu Tyr Ser Ser Ser Ser Ser His Ser Ser
                245                 250                 255

Ser Asp Ile Ser Ser Ser Val Ile Gly Tyr Asp Phe Leu Gly
            260                 265                 270
```

<210> SEQ ID NO 2
<211> LENGTH: 821
<212> TYPE: DNA
<213> ORGANISM: Brassica napus

<400> SEQUENCE: 2

```
tgataagctt atgggaaggt ctccttgctg tgagaaggac cacacgaaca aaggagcttg    60
gactaaagaa gaagacgata agctcgtctc ttacatcaaa tctcacggcg aaggctgttg   120
gcgctctctt ccaagatccg ccggtcttct ccgctgcggc aaaagctgcc gtcttcggtg   180
gattaactat ctccgacctg atctcaagag aggtaacttc accctcgaag aagacgatct   240
catcatcaaa ctccatagcc tccttggaaa caaatggtct cttatcgcga cgagattacc   300
```

```
ggggagaaca gataacgaga tcaagaacta ctggaataca cacgtaaaga ggaagctttt      360
gagaggaggg attgatccca cgactcatcg gccgatcaac gaagccaaag ctcctcgtga      420
ttcgtctgag actagagaga cagaggactc gcttgtgaag tttctatctt tcagtcgtca      480
actggagaaa aaggaaagtt ttggggaaga gagaaatgat cagaaaggac tgatttgcaa      540
aaaagagaga gttgagtatt cgattgttga agaaaagtgc ttagatttga atcttgagct      600
tagaatcagc ccgccatggc aagaccaaca gcaccatgat gagaccaaac tttggtttgg      660
gaaagagaag tacatgtgca ctgcatgccg ttttgggttg ggaaacggca agaagtgtag      720
ctgcgataat gttaaatgtc aagtcgagta cagtagtagc agcagcagcc attcttcaag      780
cgatattagt agtagcgtta ttggttatga cttcttgggt a                         821
```

```
<210> SEQ ID NO 3
<211> LENGTH: 320
<212> TYPE: PRT
<213> ORGANISM: Brassica napus

<400> SEQUENCE: 3

Met Gly Arg Ile Pro Cys Cys Glu Lys Glu Asn Val Lys Arg Gly Gln
1               5                   10                  15

Trp Thr Pro Glu Glu Asp Asn Lys Leu Ala Ser Tyr Ile Ala Gln His
            20                  25                  30

Gly Thr Arg Asn Trp Arg Leu Ile Pro Lys Asn Ala Gly Leu Gln Arg
        35                  40                  45

Cys Gly Lys Ser Cys Arg Leu Arg Trp Thr Asn Tyr Leu Arg Pro Asp
    50                  55                  60

Leu Lys His Gly Gln Phe Ser Glu Ala Glu His Ile Ile Val Lys
65                  70                  75                  80

Phe His Ser Val Leu Gly Asn Arg Trp Ser Leu Ile Ala Ala Gln Leu
                85                  90                  95

Pro Gly Arg Thr Asp Asn Asp Val Lys Asn Tyr Trp Asn Thr Lys Leu
            100                 105                 110

Lys Lys Lys Leu Ser Gly Met Gly Ile Asp Pro Val Thr His Lys Pro
        115                 120                 125

Phe Ser His Leu Met Ala Glu Ile Thr Thr Thr Leu Asn Pro Pro Gln
    130                 135                 140

Val Ser His Leu Ala Glu Ala Ala Leu Gly Cys Phe Lys Asp Glu Met
145                 150                 155                 160

Leu His Leu Leu Thr Lys Lys Arg Val Asp Leu Asn Gln Ile Asn Phe
                165                 170                 175

Ser Ser Pro Asn Pro Asn Asn Phe Thr Arg Thr Val Asp Ser Glu Ala
            180                 185                 190

Gly Lys Met Lys Met Asp Gly Leu Glu Asn Gly Asn Gly Ile Met Lys
        195                 200                 205

Leu Trp Asp Met Gly Asn Gly Phe Ser Tyr Gly Ser Ser Ser Ser
    210                 215                 220

Phe Gly Asn Glu Asp Lys Asn Asp Gly Ala Ala Ser Pro Ala Val Ala
225                 230                 235                 240

Ala Trp Arg Gly His Gly Gly Ile Arg Thr Ala Val Ala Glu Thr Ala
                245                 250                 255

Ala Ala Glu Glu Glu Glu Arg Arg Lys Leu Lys Gly Glu Val Val Asp
            260                 265                 270

Gln Glu Glu Asn Gly Ser Gln Gly Gly Arg Gly Asp Gly Met Leu Met
        275                 280                 285
```

```
Met Arg Ser Gln His Asp Gln His Gln His His Val Phe Asn Val Asp
    290                 295                 300

Asn Val Leu Trp Asp Leu Gln Ala Asp Asp Leu Ile Asn His Val Val
305                 310                 315                 320
```

<210> SEQ ID NO 4
<211> LENGTH: 963
<212> TYPE: DNA
<213> ORGANISM: Brassica napus

<400> SEQUENCE: 4

```
atgggtagga ttccatgctg tgaaaaggag aatgtgaaga gagggcaatg gactcctgaa      60
gaagacaaca aactggcttc ttacattgct caacatggta ctcgtaattg cgtctcatc     120 cctaaaaacg ctggattgca gagatgtgga aagagttgta gactacggtg acaaactat     180 ttgcgtcctg acctgaaaca tggtcaattt tctgaggctg aagaacatat catcgtcaag     240
tttcactctg ttcttggtaa ccggtggtcg ttgattgcgg cccagcttcc tggtcgaaca     300
gacaacgatg tgaaaaatta ttggaacaca aagctgaaga gaagttgtc gggaatggga     360 atagatcccg taacccacaa gcctttctcg catctaatgg cagagataac cactacactc     420
aatcctcctc aagtctcaca cctcgctgaa gctgccctcg gatgtttcaa ggacgagatg     480
cttcacttgc tcaccaagaa acgtgttgat ctaaaccaaa tcaacttctc cagccctaac     540
cctaacaact ttacccgaac cgttgatagc gaagctggta aaatgaaaat ggatggtttg     600
gagaatggta atgggataat gaagctatgg gacatgggga atggattctc ctatggatct     660
tcttcgtcat cgtttgggaa tgaagacaaa aatgatggag ctgcgtctcc tgcggttgcg     720
gcgtggaggg gtcacggtgg aatacgtaca gcggtggctg aaactgcggc agcggaggag     780
gaagagagga ggaaattgaa gggagaagtg gtggaccaag aggagaatgg atctcaagga     840
ggaagaggag atggaatgtt gatgatgagg agccagcatg atcaacatca acatcatgtg     900
tttaatgtgg acaatgtctt gtgggattta caagctgatg atctcattaa tcatgtggtt     960
tga                                                                     963
```

<210> SEQ ID NO 5
<211> LENGTH: 264
<212> TYPE: PRT
<213> ORGANISM: Brassica napus

<400> SEQUENCE: 5

```
Gly Arg Ile Pro Cys Cys Glu Lys Glu Asn Val Lys Arg Gly Gln Trp
1               5                   10                  15

Thr Pro Glu Glu Asp Asn Lys Leu Ala Ser Tyr Ile Ala Gln His Gly
            20                  25                  30

Thr Arg Asn Trp Arg Leu Ile Pro Lys Asn Ala Gly Leu Gln Arg Cys
        35                  40                  45

Gly Lys Ser Cys Arg Leu Arg Trp Thr Asn Tyr Leu Arg Pro Asp Leu
    50                  55                  60

Lys His Gly Gln Phe Ser Asp Ala Glu Glu His Ile Ile Val Lys Phe
65                  70                  75                  80

His Ser Val Leu Gly Asn Arg Trp Ser Leu Ile Ala Ala Gln Leu Pro
                85                  90                  95

Gly Arg Thr Asp Asn Asp Val Lys Asn Tyr Trp Asn Thr Lys Leu Lys
            100                 105                 110

Lys Lys Leu Ser Gly Met Gly Ile Asp Pro Val Thr His Lys Pro Phe
        115                 120                 125
```

```
Ser His Leu Met Ala Glu Ile Thr Thr Thr Leu Asn Pro Pro Gln Val
    130                 135                 140

Ser His Leu Ala Glu Ala Ala Leu Gly Cys Phe Lys Asp Glu Met Leu
145                 150                 155                 160

His Leu Leu Thr Lys Lys Arg Val Asp Leu Asn Gln Ile Asn Phe Ser
                165                 170                 175

Ser Pro Asn His Asn His Asn Pro Asn Asn Phe Asn Gln Thr Val Asp
            180                 185                 190

Asn Glu Ala Gly Lys Met Lys Leu Asp Tyr Gly Asn Gly Ile Met Lys
            195                 200                 205

Leu Trp Asp Met Gly Asn Gly Phe Ser Tyr Gly Ser Ser Ser Ser
210                 215                 220

Phe Gly Asn Asp Glu Arg Asn Glu Gly Ser Ala Ser Pro Ala Val Ala
225                 230                 235                 240

Ala Trp Arg Gly His Gly Gly Ile Arg Thr Ser Val Ala Glu Thr Ala
                245                 250                 255

His Glu Glu Glu Glu Ser Phe Pro
            260
```

<210> SEQ ID NO 6
<211> LENGTH: 792
<212> TYPE: DNA
<213> ORGANISM: Brassica napus

<400> SEQUENCE: 6

```
ggtcggattc catgttgtga aaggagaat gtgaaagag acaatggac tcctgaagaa      60
gacaacaaat tggcttctta cattgctcaa cacggtactc gtaattggcg tctcatccct    120
aaaaacgctg gattgcagag atgtgggaag agttgtagac taagatggac gaactatttg    180
cgtcctgacc tgaaacacgg acagttttct gacgctgaag aacatatcat tgtcaagttt    240
cactctgttc ttggtaacag gtggtcgttg attgcggcgc agcttccagg tcgaacagac    300
aacgatgtga aaactattg gaacacgaag ctgaagaaga agttgtcggg aatggggata    360
gatccagtta ctcacaagcc tttctcgcac ctaatggcag agatcaccac tacactcaac    420
cctccccagg tctctcacct cgctgaagct gcactcggtt gtttcaagga cgagatgctt    480
cacttgctca ccaagaaacg tgttgaccta aaccaaatca acttctcaag ccctaaccat    540
aaccataacc ctaacaactt taaccaaact gttgataacg aagctggtaa gatgaaactg    600
gattatggta tgggataat gaagctatgg gacatggta atggattctc gtatggatca    660
tcttcctcgt cctttgggaa tgatgaaagg aacgagggat ccgcgtctcc tgcggttgcg    720
gcgtggaggg gtcacggtgg aatacgtaca tcagtggctg aaaccgcgca cgaggaggag    780
gaaagcttcc cc                                                        792
```

<210> SEQ ID NO 7
<211> LENGTH: 273
<212> TYPE: PRT
<213> ORGANISM: Arabidopsis thaliana

<400> SEQUENCE: 7

```
Met Gly Arg Ser Pro Cys Cys Glu Lys Asp His Thr Asn Lys Gly Ala
1               5                  10                  15

Trp Thr Lys Glu Glu Asp Asp Lys Leu Ile Ser Tyr Ile Lys Ala His
                20                  25                  30

Gly Glu Gly Cys Trp Arg Ser Leu Pro Arg Ser Ala Gly Leu Gln Arg
            35                  40                  45
```

```
Cys Gly Lys Ser Cys Arg Leu Arg Trp Ile Asn Tyr Leu Arg Pro Asp
         50                  55                  60

Leu Lys Arg Gly Asn Phe Thr Leu Glu Glu Asp Asp Leu Ile Ile Lys
 65                  70                  75                  80

Leu His Ser Leu Leu Gly Asn Lys Trp Ser Leu Ile Ala Thr Arg Leu
                 85                  90                  95

Pro Gly Arg Thr Asp Asn Glu Ile Lys Asn Tyr Trp Asn Thr His Val
                100                 105                 110

Lys Arg Lys Leu Leu Arg Lys Gly Ile Asp Pro Ala Thr His Arg Pro
            115                 120                 125

Ile Asn Glu Thr Lys Thr Ser Gln Asp Ser Ser Asp Ser Ser Lys Thr
    130                 135                 140

Glu Asp Pro Leu Val Lys Ile Leu Ser Phe Gly Pro Gln Leu Glu Lys
145                 150                 155                 160

Ile Ala Asn Phe Gly Asp Glu Arg Ile Gln Lys Arg Val Tyr Ser Val
                165                 170                 175

Val Glu Glu Arg Cys Leu Asp Leu Asn Leu Glu Leu Arg Ile Ser Pro
                180                 185                 190

Pro Trp Gln Asp Lys Phe His Asp Glu Arg Asn Leu Arg Phe Gly Arg
            195                 200                 205

Val Lys His Arg Cys Ser Ala Cys Arg Phe Gly Phe Gly Asn Gly Lys
    210                 215                 220

Glu Cys Ser Cys Asn Asn Val Lys Cys Gln Thr Glu Asp Ser Ser Ser
225                 230                 235                 240

Ser Ser Tyr Ser Ser Thr Asp Ile Ser Ser Ile Gly Tyr Asp Phe
                245                 250                 255

Leu Gly Leu Asn Asn Thr Arg Val Leu Asp Phe Ser Thr Leu Glu Met
            260                 265                 270

Lys

<210> SEQ ID NO 8
<211> LENGTH: 1950
<212> TYPE: DNA
<213> ORGANISM: Arabidopsis thaliana

<400> SEQUENCE: 8
gtttgtgtct tctagattaa tcctccaaac ttttgattaa ccaaaaaaat tatcaaacta      60
acatgttctc cttttttctt tagaaattct aacgaattta tctttatact gatttgaata     120
tacttaattt ggtcatttgg atgccctttta caacctcctt accaaactca ctatggcaaa    180
tatatactat tttccattgt aacataaatg tccataattt gaattaaatt cgttgcagta     240
cgaaaccatc caactttgtc caaaacaaa atccttataa ctatttactt taatgtaaat      300
atatcctcta cttttgtttt tacaaccccta gctcaaacaa atttattatt tgcgataaaa    360
aatcatatcg aacaaactcg atgattttt ttttcttacg ttattaatga aactaaaata     420
tagaaaaaaa caagatgaac caaatttttca cctatctaac tacttaaata taatatgatt     480
aaatttggta agtttgaaa agtttcttta gaaatgtgaa atattgatca cagtttctat     540
tgctaaaatc accaacaaaa cgcatgtcgc cattcataat tatggtttca cacctacaac    600
taggctaata agtaaataag tagacaacta gactcaggtt tgaaaaaacc ataaaagcca    660
tatagcgttt tctcattgaa actgcgaaca cgatcgtgtg aatgttgcag tttctagttt    720
tgatacaaac aaacaaaaac acaatttaat cttagattaa aaagaaaaaa gagaacggag    780
cccactagcc actccttcaa acgtgtctta ccaactctct tctagaaaca aattaggctt    840
```

```
caccttcctc ttccaacctc tctctctctc tctctctctt tttctcaaac catctctcca    900
taaagcccta atttcttcat cacaagaatc agaagaagaa agatgggaag gtctccttgc    960
tgtgagaaag accacacaaa caaaggagct tggactaagg aagaagacga taagctcatc   1020
tcttacatca aagctcacgg tgaaggttgt tggcgttctc ttcctagatc cgccggtctt   1080
caacgttgcg aaaaagctg tcgtctccga tggattaact atctccgacc tgatctcaag    1140 agggtaact tcaccctcga agaagatgat ctcatcatca aactacatag ccttctcggt    1200
aacaagtgag tcacaaaaca actcctctgt tttttttac tatcctctgt tatgttaaaa    1260
agctctgttt tttaaacttt gttttttttt tcttctatca ggtggtctct tattgcgacg    1320
agattaccag gaagaacaga taacgagatt aagaattact ggaacacaca tgttaagagg    1380
aagctattaa gaaaagggat tgatccggcg actcatcgac ctatcaacga gaccaaaact    1440
tctcaagatt cgtctgattc tagtaaaaca gaggaccctc ttgtcaagat tctctctttt    1500
ggtcctcagc tggagaaaat agcaaatttc ggggacgaga gaattcaaaa gagagttgag    1560
tactcagttg ttgaagaaag atgtctggac ttgaatcttg agcttaggat cagtccacca    1620
tggcaagaca agttccatga tgagaggaac ctaaggtttg ggagagtgaa gcataggtgc    1680
agtgcgtgcc gttttggatt cgggaacggc aaggagtgta gctgtaataa tgtgaaatgt    1740
caaacagagg acagtagtag cagcagttat tcttcaaccg acattagtag tagcattggt    1800
tatgacttct tgggtctaaa caacactagg gttttggatt ttagcacttt ggaaatgaaa    1860
tgaaatgaaa tactatatta atcaatttat agctgtgaat tgtgatataa aagctattaa    1920
cagactcgtt catggttctc aacttttcta                                     1950
```

<210> SEQ ID NO 9
<211> LENGTH: 273
<212> TYPE: PRT
<213> ORGANISM: Lycopersicon esculentum

<400> SEQUENCE: 9

```
Met Gly Arg Ser Pro Cys Cys Glu Lys Ala His Thr Asn Lys Gly Ala
1               5                  10                  15

Trp Thr Lys Glu Glu Asp Glu Arg Leu Ile Ser Tyr Ile Arg Ala His
                20                  25                  30

Gly Glu Gly Cys Trp Arg Ser Leu Pro Lys Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Thr Thr His Arg Ser
        115                 120                 125

Ile Asn Asp Pro Thr Thr Ile Pro Lys Val Thr Thr Ile Thr Phe Ala
    130                 135                 140

Ala Ala His Glu Asn Ile Lys Asp Ile Asp Gln Gln Asp Glu Met Ile
145                 150                 155                 160

Asn Ile Lys Ala Glu Phe Val Glu Thr Ser Lys Glu Ser Asp Asn Asn
                165                 170                 175
```

-continued

Glu Ile Ile Gln Glu Lys Ser Ser Cys Leu Pro Asp Leu Asn Leu
            180                 185                 190

Glu Leu Arg Ile Ser Pro Pro His Gln Gln Leu Asp His His Arg
            195                 200                 205

His His Gln Arg Ser Ser Leu Cys Phe Thr Cys Ser Leu Gly Ile
210                 215                 220

Gln Asn Ser Lys Asp Cys Ser Cys Gly Ser Glu Ser Asn Gly Asn Gly
225                 230                 235                 240

Trp Ser Asn Asn Met Val Ser Met Asn Ile Met Ala Gly Tyr Asp Phe
                245                 250                 255

Leu Gly Leu Lys Thr Asn Gly Leu Leu Asp Tyr Arg Thr Leu Glu Thr
            260                 265                 270

Lys

<210> SEQ ID NO 10
<211> LENGTH: 264
<212> TYPE: PRT
<213> ORGANISM: Gossypium hirsutum

<400> SEQUENCE: 10

Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Ala Thr His Arg Pro
        115                 120                 125

Leu Asn Glu Ala Ser Gln Asp Val Thr Thr Ile Ser Phe Ser Gly Ala
130                 135                 140

Lys Glu Glu Lys Glu Lys Ile Asn Thr Asn Ser Asn Asn Pro Ile
145                 150                 155                 160

Gly Phe Ile Thr Lys Asp Glu Lys Lys Ile Pro Val Gln Glu Arg Cys
                165                 170                 175

Pro Asp Leu Asn Leu Asp Leu Arg Ile Ser Pro Tyr Tyr Gln Gln
            180                 185                 190

Thr Gln Pro Glu Ser Phe Lys Thr Gly Gly Arg Thr Leu Cys Phe Ile
        195                 200                 205

Cys Ser Leu Gly Val Lys Asn Ser Lys Asp Cys Thr Cys Ser Thr Ile
210                 215                 220

Thr Thr Ala Ala Gly Ser Ser Ser Ser Ser Ser His Ser Asn Ser
225                 230                 235                 240

Asn Asn Ser Ser Gly Tyr Asp Phe Leu Gly Leu Lys Ser Gly Ile Leu
                245                 250                 255

Glu Tyr Arg Ser Leu Glu Met Lys
            260

```
<210> SEQ ID NO 11
<211> LENGTH: 285
<212> TYPE: PRT
<213> ORGANISM: Oryza sativa

<400> SEQUENCE: 11

Arg Trp Ser Val Ile Ala Ala Gln Leu Pro Gly Arg Thr Asp Asn Asp
1               5                   10                  15

Val Lys Asn His Trp Asn Thr Lys Leu Lys Lys Lys Leu Ser Gly Met
            20                  25                  30

Gly Ile Asp Pro Val Thr His Lys Ser Phe Ser His Leu Met Ala Glu
        35                  40                  45

Ile Ala Thr Thr Leu Ala Pro Pro Gln Val Ala His Leu Ala Glu Ala
    50                  55                  60

Ala Leu Gly Cys Phe Lys Asp Glu Met Leu His Leu Thr Lys Lys
65                  70                  75                  80

Arg Pro Ser Asp Phe Pro Ser Pro Ala Val His Asp Gly Ala Gly Ala
                85                  90                  95

Gly Ala Ser Ala Ser Ala Leu Ala Ala Pro Cys Phe Pro Ala Ala Pro
            100                 105                 110

Pro His His Pro Gln Ala Asp Asp Thr Ile Glu Arg Ile Lys Leu Gly
        115                 120                 125

Leu Ser Arg Ala Ile Met Ser Asp Pro Ser Thr Ala Ser Ala Ala Ala
    130                 135                 140

Ala Ala Ala Ala Pro Ser Ala Pro Ala Glu Asp Lys Pro Trp Pro Pro
145                 150                 155                 160

Gly Asp Met Ser Glu Gly Leu Ala Gly Met Tyr Ala Thr Tyr Asn Pro
                165                 170                 175

Ala Ala His Ala His Ala Gln Ala Gln Ala Glu Phe Arg Tyr Asp Gly
            180                 185                 190

Ala Ser Ala Ala Gln Gly Tyr Val Leu Gly Gly Asp Gly Asp Gln Gly
        195                 200                 205

Thr Ser Met Trp Ser His Gln Ser Leu Tyr Ser Gly Ser Ser Gly Thr
    210                 215                 220

Glu Glu Ala Arg Arg Glu Leu Pro Glu Lys Gly Asn Asp Ser Val Gly
225                 230                 235                 240

Ser Ser Gly Gly Asp Asp Ala Ala Asp Gly Lys Asp Ser Gly
                245                 250                 255

Lys Gly Ala Ala Ser Asp Met Ser Gly Leu Phe Ala Ser Asp Cys Val
            260                 265                 270

Leu Trp Asp Leu Pro Asp Glu Leu Thr Asn His Met Val
        275                 280                 285

<210> SEQ ID NO 12
<211> LENGTH: 273
<212> TYPE: PRT
<213> ORGANISM: Zea mays

<400> SEQUENCE: 12

Met Gly Arg Ser Pro Cys Cys Glu Lys Ala His Thr Asn Lys Gly Ala
1               5                   10                  15

Trp Thr Lys Glu Glu Asp Glu Arg Leu Val Ala His Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60
```

Leu Lys Arg Gly Asn Phe Thr Glu Glu Asp Glu Leu Ile Val Lys
65                  70                  75                  80

Leu His Ser Val Leu Gly Asn Lys Trp Ser Leu Ile Ala Gly Arg Leu
            85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
            115                 120                 125

Val Thr Glu His His Ala Ser Asn Ile Thr Ile Ser Phe Glu Thr Glu
130                 135                 140

Val Ala Ala Ala Arg Asp Asp Lys Lys Gly Ala Val Phe Arg Leu
145                 150                 155                 160

Glu Glu Glu Glu Glu Arg Asn Lys Ala Thr Met Val Val Gly Arg Asp
                165                 170                 175

Arg Gln Ser Gln Ser Gln Ser His Ser His Pro Ala Gly Glu Trp Gly
            180                 185                 190

Gln Gly Lys Arg Pro Leu Lys Cys Pro Asp Leu Asn Leu Asp Leu Cys
            195                 200                 205

Ile Ser Pro Pro Cys Gln Glu Glu Glu Met Glu Glu Ala Ala Met
210                 215                 220

Arg Val Arg Pro Ala Val Lys Arg Glu Ala Gly Leu Cys Phe Gly Cys
225                 230                 235                 240

Ser Leu Gly Leu Pro Arg Thr Ala Asp Cys Lys Cys Ser Ser Ser Ser
            245                 250                 255

Phe Leu Gly Leu Arg Thr Ala Met Leu Asp Phe Arg Ser Leu Glu Met
            260                 265                 270

Lys

<210> SEQ ID NO 13
<211> LENGTH: 255
<212> TYPE: PRT
<213> ORGANISM: Zea mays

<400> SEQUENCE: 13

Met Gly Arg Ser Pro Cys Cys Glu Lys Ala His Thr Asn Arg Gly Ala
1               5                   10                  15

Trp Thr Lys Glu Glu Asp Glu Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
50                  55                  60

Leu Lys Arg Gly Asn Phe Thr Ala Asp Glu Asp Asp Leu Ile Val Lys
65                  70                  75                  80

Leu His Ser Leu Leu Gly Asn Lys Trp Ser Leu Ile Ala Ala Arg Leu
            85                  90                  95

Pro Gly Arg Thr Asp Asn Glu Ile Lys Asn Tyr Trp Asn Thr His Val
            100                 105                 110

Arg Arg Lys Leu Leu Gly Arg Gly Ile Asp Pro Val Thr His Arg Pro
            115                 120                 125

Ile Ala Ala Asp Ala Val Thr Val Thr Val Ser Phe Gln Pro Ser
130                 135                 140

Pro Ser Ala Ala Ala Ala Ala Ala Glu Ala Glu Ala Thr Ala Ala
145                 150                 155                 160

```
Lys Ala Pro Arg Cys Pro Asp Leu Asn Leu Asp Leu Cys Ile Ser Pro
                165                 170                 175

Pro Cys Gln Gln Gln Glu Glu Glu Val Asp Leu Lys Pro Ser Ala
        180                 185                 190

Ala Val Val Lys Arg Glu Val Leu Leu Gly Gly Arg Gly His Gly His
            195                 200                 205

Gly His Gly Gly Ala Leu Cys Phe Gly Cys Ser Leu Gly Val Gln Lys
        210                 215                 220

Gly Ala Pro Gly Cys Ser Cys Ser Ser Ser Asn Gly His Arg Cys Leu
225                 230                 235                 240

Gly Leu Arg Gly Gly Met Leu Asp Phe Arg Gly Leu Lys Met Lys
                245                 250                 255

<210> SEQ ID NO 14
<211> LENGTH: 267
<212> TYPE: PRT
<213> ORGANISM: Hordeum vulgare

<400> SEQUENCE: 14

Met Gly Arg Ser Pro Cys Cys Glu Lys Ala His Thr Asn Lys Gly Ala
1               5                   10                  15

Trp Thr Lys Glu Glu Asp Asp Arg Leu Thr Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
50                  55                  60

Leu Lys Arg Gly Asn Phe Ser His Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Thr Ser Arg Gly Ile Asp Pro Val Thr His Arg Ala
        115                 120                 125

Ile Asn Ser Asp His Ala Ala Ser Asn Ile Thr Ile Ser Phe Glu Ser
130                 135                 140

Ala Gln Arg Asp Asp Lys Gly Ala Val Phe Arg Arg Asp Ala Glu Pro
145                 150                 155                 160

Ala Lys Ala Ala Ala Ala Ala Ala Ile Ser His His Val Asp His
            165                 170                 175

His His Arg Ser Asn Pro Gln Leu Asp Trp Gly Gln Gly Lys Pro Leu
        180                 185                 190

Lys Cys Pro Asp Leu Asn Leu Asp Leu Cys Ile Ser Pro Pro Ile His
    195                 200                 205

Glu Asp Pro Met Val Asp Thr Lys Pro Val Val Lys Arg Glu Ala Gly
        210                 215                 220

Val Gly Val Gly Val Val Gly Leu Cys Phe Ser Cys Ser Met Gly Leu
225                 230                 235                 240

Pro Arg Ser Ser Asp Cys Lys Cys Ser Ser Phe Met Gly Leu Arg Thr
                245                 250                 255

Ala Met Leu Asp Phe Arg Ser Ile Glu Met Lys
            260                 265

<210> SEQ ID NO 15
<211> LENGTH: 234
```

<212> TYPE: PRT
<213> ORGANISM: Nicotiana tabacum

<400> SEQUENCE: 15

```
Met Gly Arg Ser Pro Cys Cys Glu Lys Ala His Thr Asn Lys Gly Ala
1               5                   10                  15

Trp Thr Arg Glu Glu Asp Glu Arg Leu Val Ala His Val Arg Ala His
            20                  25                  30

Gly Glu Gly Cys Trp Arg Ser Leu Pro Ser Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Ser Arg Asp Glu Asp Glu Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Leu Thr Asp Ala Ala Thr Val Ser Phe Val His Pro Ala Glu Ala Thr
    130                 135                 140

Lys Gln Gln Ala Thr Glu Glu Arg Lys Pro Pro Arg Cys Pro Asp Leu
145                 150                 155                 160

Asn Leu Asp Leu Cys Ile Ser Leu Pro Phe Gln Gln Glu Glu Glu Arg
                165                 170                 175

Pro Pro Ala Arg Ala Cys Ala Lys Pro Val Lys Met Glu Gln Leu Gln
            180                 185                 190

Gln Gly Gly Ile Cys Phe Arg Cys Ser Ile Leu Arg Val Arg Gly Ala
        195                 200                 205

Ala Thr Glu Cys Ser Cys Gly Ser Lys Phe Leu Gly Leu Arg Ala Gly
    210                 215                 220

Met Leu Asp Phe Arg Gly Leu Glu Met Lys
225                 230
```

<210> SEQ ID NO 16
<211> LENGTH: 849
<212> TYPE: DNA
<213> ORGANISM: Triticum aestivum

<400> SEQUENCE: 16

```
agtcatcggc ggcggcagac catctacaga gatagtgaga tggggaggtc gccgtgctgc      60
gagaaggcgc acaccaacaa gggcgcctgg accaaggagg aggacgaccg gctcaccgcc     120
tacatcaagg cgcacggcga gggctgctgg cgctccctgc ccaaggccgc ggggttgctc     180
cgctgcggca agagctgccg cctccgctgg atcaactacc tccgcccga cctcaagcgc     240
ggcaacttca gcgatgagga ggacgagctc atcatcaagc tccacagcct cctgggcaac     300
aaatggtctc tgatagccgg gagactccca ggaggacgg acaacgagat caagaactac     360
tggaacacgc acatcaggag gaagctcacg agccggggga tcgacccggt gacccaccgc     420
gcgatcaaca cgaccacgc cgtccaac atcaccatat ccttcgagac ggcgcagagg     480
gacgacaagg gcgccgtgtt ccggcgagac gccgagccca ccaaggtagc ggcagcggca     540
gcggcgatca cccacgtgga ccaccatcac catcaccgta gcaacccct ccaccagatg     600
gagtggggcc aggggaagcc gctcaagtgc ccggacctga acctggacct ctgcatcagc     660
```

-continued

```
cccccgtccc acgaggaccc catggtggac accaagcccg tggtgaagag ggaggccgtc      720
gtgggcctct gcttcagctg cagcatgggg ctccccagga gcgcggactg caagtgcagc      780
agcttcatgg ggctccggac cgccatgctc gacttcagaa gcatcgagat gaaatgagca      840
gagcagagc                                                              849
```

```
<210> SEQ ID NO 17
<211> LENGTH: 265
<212> TYPE: PRT
<213> ORGANISM: Triticum aestivum

<400> SEQUENCE: 17
```

Met Gly Arg Ser Pro Cys Cys Glu Lys Ala His Thr Asn Lys Gly Ala
1               5                   10                  15

Trp Thr Lys Glu Glu Asp Asp Arg Leu Thr Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Ser Asp Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Thr Ser Arg Gly Ile Asp Pro Val Thr His Arg Ala
        115                 120                 125

Ile Asn Ser Asp His Ala Ala Ser Asn Ile Thr Ile Ser Phe Glu Thr
    130                 135                 140

Ala Gln Arg Asp Asp Lys Gly Ala Val Phe Arg Arg Asp Ala Glu Pro
145                 150                 155                 160

Thr Lys Val Ala Ala Ala Ala Ala Ile Thr His Val Asp His His
                165                 170                 175

His His His Arg Ser Asn Pro Leu His Gln Met Glu Trp Gly Gln Gly
            180                 185                 190

Lys Pro Leu Lys Cys Pro Asp Leu Asn Leu Asp Leu Cys Ile Ser Pro
        195                 200                 205

Pro Ser His Glu Asp Pro Met Val Asp Thr Lys Pro Val Val Lys Arg
    210                 215                 220

Glu Ala Val Val Gly Leu Cys Phe Ser Cys Ser Met Gly Leu Pro Arg
225                 230                 235                 240

Ser Ala Asp Cys Lys Cys Ser Ser Phe Met Gly Leu Arg Thr Ala Met
                245                 250                 255

Leu Asp Phe Arg Ser Ile Glu Met Lys
            260                 265

```
<210> SEQ ID NO 18
<211> LENGTH: 372
<212> TYPE: PRT
<213> ORGANISM: Oryza sativa

<400> SEQUENCE: 18
```

Met Gly Arg Val Pro Cys Cys Glu Lys Asp Asn Val Lys Arg Gly Gln
1               5                   10                  15

Trp Thr Pro Glu Glu Asp Asn Lys Leu Leu Ser Tyr Ile Thr Gln Tyr
            20                  25                  30

```
Gly Thr Arg Asn Trp Arg Leu Ile Pro Lys Asn Ala Gly Leu Gln Arg
            35                  40                  45

Cys Gly Lys Ser Cys Arg Leu Arg Trp Thr Asn Tyr Leu Arg Pro Asp
 50                  55                  60

Leu Lys His Gly Glu Phe Thr Asp Ala Glu Gln Thr Ile Ile Lys
 65                  70                  75                  80

Leu His Ser Val Val Gly Asn Arg Trp Ser Val Ile Ala Ala Gln Leu
                    85                  90                  95

Pro Gly Arg Thr Asp Asn Asp Val Lys Asn His Trp Asn Thr Lys Leu
                100                 105                 110

Lys Lys Lys Leu Ser Gly Met Gly Ile Asp Pro Val Thr His Lys Ser
            115                 120                 125

Phe Ser His Leu Met Ala Glu Ile Ala Thr Thr Leu Ala Pro Pro Gln
130                 135                 140

Val Ala His Leu Ala Glu Ala Ala Leu Gly Cys Phe Lys Asp Glu Met
145                 150                 155                 160

Leu His Leu Leu Thr Lys Lys Arg Pro Ser Asp Phe Pro Ser Pro Ala
                165                 170                 175

Val His Asp Gly Ala Gly Ala Gly Ala Ser Ala Ser Ala Leu Ala Ala
                180                 185                 190

Pro Cys Phe Pro Ala Ala Pro Pro His His Pro Gln Ala Asp Asp Thr
                195                 200                 205

Ile Glu Arg Ile Lys Leu Gly Leu Ser Arg Ala Ile Met Ser Asp Pro
            210                 215                 220

Ser Thr Ala Ser Ala Ala Ala Ala Ala Pro Ser Ala Pro Ala
225                 230                 235                 240

Glu Asp Lys Pro Trp Pro Pro Gly Asp Met Ser Glu Gly Leu Ala Gly
                245                 250                 255

Met Tyr Ala Thr Tyr Asn Pro Ala Ala His His Ala Gln Ala Gln
                260                 265                 270

Ala Glu Phe Arg Tyr Asp Gly Ala Ser Ala Ala Gln Gly Tyr Val Leu
            275                 280                 285

Gly Gly Asp Gly Asp Gln Gly Thr Ser Met Trp Ser His Gln Ser Leu
290                 295                 300

Tyr Ser Gly Ser Ser Gly Thr Glu Glu Ala Arg Arg Glu Leu Pro Glu
305                 310                 315                 320

Lys Gly Asn Asp Ser Val Gly Ser Ser Gly Asp Asp Ala Ala
                325                 330                 335

Asp Asp Gly Lys Asp Ser Gly Lys Gly Ala Ala Ser Asp Met Ser Gly
                340                 345                 350

Leu Phe Ala Ser Asp Cys Val Leu Trp Asp Leu Pro Glu Leu Thr
            355                 360                 365

Asn His Met Val
    370

<210> SEQ ID NO 19
<211> LENGTH: 1309
<212> TYPE: DNA
<213> ORGANISM: Oryza sativa

<400> SEQUENCE: 19 atgggcggg  tgccgtgctg  cgagaaggac  aacgtgaagc  gcgggcagtg  gacgcccgag    60
gaggacaaca  agctgctctc  ctacatcacc  cagtacggca  cccgcaactg  gcgcctcatc   120
cccaagaacg  ccggtacgtt  ggcgcgcgcg  ccgccaccgg  cgaacgcgtg  gttgcagcag   180
```

```
cggcggcgct ctgaccgggg tgtttgttgc tggaacgttg gcagggttgc agcggtgcgg      240
gaagagctgc cggctgcggt ggaccaacta cctccggccc gacctcaagc acggcgagtt      300
caccgacgcc gaggagcaga ccatcatcaa gctccactcc gtcgtcggca acaggtaggc      360
atcaacgagt ggtctcgcta caccgtcttg tgatcttggg tcatttttgg aggaatgtat      420
tgagcaatgc gggatggggc tgtgtgtggc aaggtggtcg gtgatcgcgg cgcagcttcc      480
ggggcggacg gacaacgacg tgaagaacca ctggaacacg aagctgaaga agaagctgtc      540
cgggatgggc atcgaccccg tcacgcacaa gtccttctcg cacctcatgg ccagatcgc      600 caccacgctg gcgccgccgc aggtggcgca cctcgccgag gccgcgctgg ggtgcttcaa      660
ggacgagatg ctccacctcc tcaccaagaa gcgcccctcc gacttcccct cgcccgccgt      720
gcacgacggg gccggcgccg gcgccagcgc gtccgcgctc gccgcgccct gtttccccgc      780
cgcgccgccg caccacccgc aggccgacga caccatcgag cgcatcaagc tcggcctgtc      840
ccgcgccatc atgagcgatc cctccaccgc ctccgccgcc gccgccgcg ccgcgccctc      900 cgcccccgcg gaggacaagc cgtggccgcc cggcgacatg tccgaggggc tcgccgggat      960
gtacgccacg tacaacccgg cggcgcacgc gcacgcgcag gcccaggccg agttccggta     1020
cgacggggcc tccgcggcgc agggctacgt cctcggcggc gacggcgacc agggcacgtc     1080
gatgtggagc caccagagcc tgtacagcgg gagctccggc accgaggagg ccaggcggga     1140
gttgccggag aagggcaacg acagcgtcgg cagcagcggc ggcgacgacg acgccgcgga     1200
cgacggcaag gacagcggga agggggcagc ctccgacatg tcgggcctgt tcgcctccga     1260
ctgcgtgctc tgggacttgc ccgacgagct cacgaatcac atggtgtag              1309

<210> SEQ ID NO 20
<211> LENGTH: 69
<212> TYPE: PRT
<213> ORGANISM: Triticum aestivum

<400> SEQUENCE: 20

Thr Asp Asn Asp Val Lys Asn His Trp Asn Thr Lys Leu Lys Lys Lys
1               5                   10                  15

Leu Ser Gly Met Gly Ile Asp Pro Val Thr His Lys Ser Phe Ser His
            20                  25                  30

Leu Met Ala Glu Ile Ala Thr Thr Leu Ala Pro Pro Gln Val Ala His
        35                  40                  45

Leu Ala Glu Ala Ala Leu Gly Cys Phe Lys Asp Glu Met Leu His Leu
    50                  55                  60

Leu Thr Lys Lys Arg
65

<210> SEQ ID NO 21
<211> LENGTH: 185
<212> TYPE: DNA
<213> ORGANISM: Triticum aestivum

<400> SEQUENCE: 21
accgacaacg atgtcaagaa ccactggaac accaagctca agaagaagct gtccgggatg       60
ggcatcgacc ccgtcacgca caagtccttc tcgcacctca tggccgagat cgccaccacg      120
ctcgccccgc cgcaggtggc gcacctcgcc gaggccgccc tggggtgctt caaagacgag      180
atgct                                                                  185

<210> SEQ ID NO 22
```

<211> LENGTH: 320
<212> TYPE: PRT
<213> ORGANISM: Arabidopsis thaliana

<400> SEQUENCE: 22

Met Gly Arg Ile Pro Cys Cys Glu Lys Glu Asn Val Lys Arg Gly Gln
1               5                   10                  15

Trp Thr Pro Glu Glu Asp Asn Lys Leu Ala Ser Tyr Ile Ala Gln His
            20                  25                  30

Gly Thr Arg Asn Trp Arg Leu Ile Pro Lys Asn Ala Gly Leu Gln Arg
        35                  40                  45

Cys Gly Lys Ser Cys Arg Leu Arg Trp Thr Asn Tyr Leu Arg Pro Asp
50                  55                  60

Leu Lys His Gly Gln Phe Ser Glu Ala Glu His Ile Ile Val Lys
65                  70                  75                  80

Phe His Ser Val Leu Gly Asn Arg Trp Ser Leu Ile Ala Ala Gln Leu
                85                  90                  95

Pro Gly Arg Thr Asp Asn Asp Val Lys Asn Tyr Trp Asn Thr Lys Leu
            100                 105                 110

Lys Lys Lys Leu Ser Gly Met Gly Ile Asp Pro Val Thr His Lys Pro
        115                 120                 125

Phe Ser His Leu Met Ala Glu Ile Thr Thr Thr Leu Asn Pro Pro Gln
130                 135                 140

Val Ser His Leu Ala Glu Ala Ala Leu Gly Cys Phe Lys Asp Glu Met
145                 150                 155                 160

Leu His Leu Leu Thr Lys Lys Arg Val Asp Leu Asn Gln Ile Asn Phe
                165                 170                 175

Ser Asn His Asn Pro Asn Pro Asn Asn Phe His Glu Ile Ala Asp Asn
            180                 185                 190

Glu Ala Gly Lys Ile Lys Met Asp Gly Leu Asp His Gly Asn Gly Ile
        195                 200                 205

Met Lys Leu Trp Asp Met Gly Asn Gly Phe Ser Tyr Gly Ser Ser Ser
210                 215                 220

Ser Ser Phe Gly Asn Glu Glu Arg Asn Asp Gly Ser Ala Ser Pro Ala
225                 230                 235                 240

Val Ala Ala Trp Arg Gly His Gly Gly Ile Arg Thr Ala Val Ala Glu
                245                 250                 255

Thr Ala Ala Glu Glu Glu Arg Arg Lys Leu Lys Gly Glu Val
            260                 265                 270

Val Asp Gln Glu Glu Ile Gly Ser Glu Gly Arg Gly Asp Gly Met
        275                 280                 285

Thr Met Met Arg Asn His His His Gln His Val Phe Asn Val Asp
290                 295                 300

Asn Val Leu Trp Asp Leu Gln Ala Asp Asp Leu Ile Asn His Met Val
305                 310                 315                 320

<210> SEQ ID NO 23
<211> LENGTH: 963
<212> TYPE: DNA
<213> ORGANISM: Arabidopsis thaliana

<400> SEQUENCE: 23
atgggtcgga ttccatgttg tgaaaaggag aatgtgaaga gaggacaatg gactcctgaa    60
gaagacaaca aattggcttc ttatattgct caacatggta ctcgtaattg gcgtctcatc   120
cctaagaatg ctgggttgca agatgtggg aagagttgta ggctgcgatg gacaaactat   180

```
ctgcgtccgg atttgaaaca tggccagttc tcggaggctg aagaacatat cattgtcaag    240
tttcactctg ttcttggtaa ccggtggtcg ttgattgcgg cgcaacttcc tggtcggaca    300
gacaacgatg tgaaaaatta ttggaacacg aagctgaaga agaagttgtc aggaatggga    360
atagatccgt gacccacaa gcctttctcg catctaatgg cagagatcac cactacactt     420
aatcctcctc aggtttctca cctagccgaa gctgccctcg gctgtttcaa ggacgagatg    480
cttcacttgc tcaccaagaa acgtgttgac ctaaaccaaa tcaacttttc aaaccataac    540
cctaacccaa acaactttca cgagattgct gataatgaag ctggtaagat aaagatggat    600
ggtttggacc atgggaatgg gataatgaag ttatgggaca tgggtaatgg attctcatat    660
ggatcctctt cgtcttcgtt tgggaatgaa gaaagaaatg atggatcagc gtctcctgcc    720
gttgcagctt ggaggggtca cggaggaata cgtaccgcgg tagctgaaac cgcggcagcg    780
gaggaggagg agagaaggaa gctgaaggga gaagtggttg atcaagagga gattggatct    840
gaaggaggaa gaggagatgg aatgacgatg atgaggaacc atcatcatca tcaacatgtg    900
tttaatgtgg ataatgtctt gtgggattta caagctgatg atctcatcaa tcatatggtt    960
tga                                                                  963
```

<210> SEQ ID NO 24
<211> LENGTH: 262
<212> TYPE: PRT
<213> ORGANISM: Brassica napus

<400> SEQUENCE: 24

```
Met Gly Arg Ile Pro Cys Cys Glu Lys Glu Asn Val Lys Arg Gly Gln
1               5                   10                  15

Trp Thr Pro Glu Glu Asp Asn Lys Leu Ala Ser Tyr Ile Ala Gln His
            20                  25                  30

Gly Thr Arg Asn Trp Arg Leu Ile Pro Lys Asn Ala Gly Leu Gln Arg
        35                  40                  45

Cys Gly Lys Ser Cys Arg Leu Arg Trp Thr Asn Tyr Leu Arg Pro Asp
    50                  55                  60

Leu Lys His Gly Gln Phe Ser Asp Ala Glu Glu His Ile Ile Val Lys
65                  70                  75                  80

Phe His Ser Val Leu Gly Asn Arg Trp Ser Leu Ile Ala Ala Gln Leu
                85                  90                  95

Pro Gly Arg Thr Asp Asn Asp Val Lys Asn Tyr Trp Asn Thr Lys Leu
            100                 105                 110

Lys Lys Lys Leu Ser Gly Met Gly Ile Asp Pro Val Thr His Lys Pro
        115                 120                 125

Phe Ser His Leu Met Ala Glu Ile Thr Thr Thr Leu Asn Pro Pro Gln
    130                 135                 140

Val Ser His Leu Ala Glu Ala Ala Leu Gly Cys Phe Lys Asp Glu Met
145                 150                 155                 160

Leu His Leu Leu Thr Lys Lys Arg Val Asp Leu Asn Gln Ile Asn Phe
                165                 170                 175

Ser Ser Pro Asn His Asn His Asn Pro Asn Phe Asn Gln Thr Val
            180                 185                 190

Asp Asn Glu Ala Gly Lys Met Lys Leu Asp Tyr Gly Asn Gly Ile Met
        195                 200                 205

Lys Leu Trp Asp Met Gly Asn Gly Phe Ser Tyr Gly Ser Ser Ser Ser
    210                 215                 220

Ser Phe Gly Asn Asp Glu Arg Asn Glu Gly Ser Ala Ser Pro Ala Val
225                 230                 235                 240
```

Ala Ala Trp Arg Gly His Gly Gly Ile Arg Thr Ser Val Ala Glu Thr
                245                 250                 255

Ala His Glu Glu Glu Glu
            260

<210> SEQ ID NO 25
<211> LENGTH: 261
<212> TYPE: PRT
<213> ORGANISM: Brassica napus

<400> SEQUENCE: 25

Tyr Leu Arg Pro Asp Leu Lys His Gly Gln Phe Ser Glu Ala Glu Glu
1               5                   10                  15

His Ile Ile Val Lys Phe His Ser Val Leu Gly Asn Arg Trp Ser Leu
            20                  25                  30

Ile Ala Ala Gln Leu Pro Gly Arg Thr Asp Asn Asp Val Lys Asn Tyr
        35                  40                  45

Trp Asn Thr Lys Leu Lys Lys Leu Ser Gly Met Gly Ile Asp Pro
    50                  55                  60

Val Thr His Lys Pro Phe Ser His Leu Met Ala Glu Ile Thr Thr Thr
65                  70                  75                  80

Leu Asn Pro Pro Gln Val Ser His Leu Ala Glu Ala Ala Leu Gly Cys
                85                  90                  95

Phe Lys Asp Glu Met Leu His Leu Leu Thr Lys Lys Arg Val Asp Leu
            100                 105                 110

Asn Gln Ile Asn Phe Ser Ser Pro Asn Pro Asn Phe Thr Arg Thr
        115                 120                 125

Val Asp Ser Glu Ala Gly Lys Met Lys Met Asp Gly Leu Glu Asn Gly
130                 135                 140

Asn Gly Ile Met Lys Leu Trp Asp Met Gly Asn Gly Phe Ser Tyr Gly
145                 150                 155                 160

Ser Ser Ser Ser Ser Phe Gly Asn Glu Asp Lys Asn Asp Gly Ala Ala
                165                 170                 175

Ser Pro Ala Val Ala Ala Trp Arg Gly His Gly Gly Ile Arg Thr Ala
            180                 185                 190

Val Ala Glu Thr Ala Ala Ala Glu Glu Glu Arg Arg Lys Leu Lys
        195                 200                 205

Gly Glu Val Val Asp Gln Glu Glu Asn Gly Ser Gln Gly Gly Arg Gly
    210                 215                 220

Asp Gly Met Leu Met Met Arg Ser Gln His Asp Gln His Gln His His
225                 230                 235                 240

Val Phe Asn Ala Asp Asn Val Leu Trp Asp Leu Gln Ala Asp Asp Leu
                245                 250                 255

Ile Asn His Val Val
            260

<210> SEQ ID NO 26
<211> LENGTH: 320
<212> TYPE: PRT
<213> ORGANISM: Brassica napus

<400> SEQUENCE: 26

Met Gly Arg Ile Pro Cys Cys Glu Lys Glu Asn Val Lys Arg Gly Gln
1               5                   10                  15

Trp Thr Pro Glu Glu Asp Asn Lys Leu Ala Ser Tyr Ile Ala Gln His
            20                  25                  30

```
Gly Thr Arg Asn Trp Arg Leu Ile Pro Lys Asn Ala Gly Leu Gln Arg
             35                  40                  45

Cys Gly Lys Ser Cys Arg Leu Arg Trp Thr Asn Tyr Leu Arg Pro Asp
 50                  55                  60

Leu Lys His Gly Gln Phe Ser Asp Ala Glu Glu His Ile Ile Val Lys
 65                  70                  75                  80

Phe His Ser Val Leu Gly Asn Arg Trp Ser Leu Ile Ala Ala Gln Leu
                 85                  90                  95

Leu Gly Arg Thr Asp Asn Asp Val Lys Asn Tyr Trp Asn Thr Lys Leu
            100                 105                 110

Lys Lys Lys Leu Ser Gly Met Gly Lys Asp Pro Val Thr His Lys Pro
        115                 120                 125

Phe Ser His Leu Met Ala Glu Ile Thr Thr Thr Leu Asn Pro Pro Gln
    130                 135                 140

Val Ser His Leu Ala Glu Ala Ala Leu Gly Cys Phe Lys Asp Glu Met
145                 150                 155                 160

Leu His Leu Leu Thr Lys Lys Arg Val Asp Leu Asn Gln Ile Asn Phe
                165                 170                 175

Ser Ser Pro Asn His Asn His Asn Pro Asn Asn Phe Asn Gln Thr Val
            180                 185                 190

Asp Asn Glu Ala Gly Lys Met Lys Leu Asp Tyr Gly Asn Gly Ile Met
        195                 200                 205

Lys Leu Trp Asp Met Gly Asn Gly Phe Ser Tyr Gly Ser Ser Ser Ser
    210                 215                 220

Ser Phe Gly Asn Asp Glu Arg Asn Glu Gly Ser Ala Ser Pro Ala Val
225                 230                 235                 240

Ala Ala Trp Arg Gly His Gly Gly Ile Arg Thr Ser Val Ala Glu Thr
                245                 250                 255

Ala Ala Val Glu Glu Glu Glu Arg Arg Lys Leu Lys Gly Glu Val Met
            260                 265                 270

Glu Gln Glu Glu Ile Gly Ser Glu Gly Gly Arg Gly Asp Gly Met Thr
        275                 280                 285

Met Arg Arg Gln His Asp Gln His Gln Gln His Ala Phe Asn Val Asp
    290                 295                 300

Asn Asp Leu Trp Asp Leu Gln Ala Asp Leu Ile Asn His Met Val
305                 310                 315                 320

<210> SEQ ID NO 27
<211> LENGTH: 12
<212> TYPE: PRT
<213> ORGANISM: Artificial
<220> FEATURE:
<223> OTHER INFORMATION: Transcription repressor motif suitable for use
      in plants

<400> SEQUENCE: 27

Leu Asp Leu Asp Leu Glu Leu Arg Leu Gly Phe Ala
 1               5                  10

<210> SEQ ID NO 28
<211> LENGTH: 12
<212> TYPE: PRT
<213> ORGANISM: Artificial
<220> FEATURE:
<223> OTHER INFORMATION: Transcription repressor motif suitable for use
      in plants

<400> SEQUENCE: 28

Leu Asp Leu Asn Leu Glu Leu Arg Ile Ser Pro Pro
```

```
<210> SEQ ID NO 29
<211> LENGTH: 12
<212> TYPE: PRT
<213> ORGANISM: Arabidopsis thaliana

<400> SEQUENCE: 29

Leu Asp Leu Asp Leu Glu Leu Arg Leu Gly Phe Ala
1               5                   10

<210> SEQ ID NO 30
<211> LENGTH: 12
<212> TYPE: PRT
<213> ORGANISM: Arabidopsis thaliana

<400> SEQUENCE: 30

Leu Asp Leu Asn Leu Glu Leu Arg Ile Ser Pro Pro
1               5                   10

<210> SEQ ID NO 31
<211> LENGTH: 38
<212> TYPE: DNA
<213> ORGANISM: Arabidopsis thaliana
<220> FEATURE:
<221> NAME/KEY: misc_feature
<222> LOCATION: (15)..(15)
<223> OTHER INFORMATION: n is c or t
<220> FEATURE:
<221> NAME/KEY: misc_feature
<222> LOCATION: (18)..(18)
<223> OTHER INFORMATION: n is c or t
<220> FEATURE:
<221> NAME/KEY: misc_feature
<222> LOCATION: (21)..(21)
<223> OTHER INFORMATION: n is a or g
<220> FEATURE:
<221> NAME/KEY: misc_feature
<222> LOCATION: (27)..(27)
<223> OTHER INFORMATION: n is a or g
<220> FEATURE:
<221> NAME/KEY: misc_feature
<222> LOCATION: (30)..(30)
<223> OTHER INFORMATION: n is c or t
<220> FEATURE:
<221> NAME/KEY: misc_feature
<222> LOCATION: (33)..(33)
<223> OTHER INFORMATION: n is c or t

<400> SEQUENCE: 31
cctggtcgta ctganaanga nattaanaan tantggaa                           38

<210> SEQ ID NO 32
<211> LENGTH: 20
<212> TYPE: DNA
<213> ORGANISM: Artificial
<220> FEATURE:
<223> OTHER INFORMATION: pBl 101

<400> SEQUENCE: 32
tgtggaattg tgagcggata                                               20

<210> SEQ ID NO 33
<211> LENGTH: 20
<212> TYPE: DNA
<213> ORGANISM: Artificial
<220> FEATURE:
<223> OTHER INFORMATION: pBl 101

<400> SEQUENCE: 33
```

-continued

```
attccacagt tttcgcgatc                                                 20

<210> SEQ ID NO 34
<211> LENGTH: 38
<212> TYPE: DNA
<213> ORGANISM: Arabidopsis thaliana
<220> FEATURE:
<221> NAME/KEY: misc_feature
<222> LOCATION: (15)..(15)
<223> OTHER INFORMATION: n is c or t
<220> FEATURE:
<221> NAME/KEY: misc_feature
<222> LOCATION: (18)..(18)
<223> OTHER INFORMATION: n is c or t
<220> FEATURE:
<221> NAME/KEY: misc_feature
<222> LOCATION: (21)..(21)
<223> OTHER INFORMATION: n is a or g
<220> FEATURE:
<221> NAME/KEY: misc_feature
<222> LOCATION: (27)..(27)
<223> OTHER INFORMATION: n is a or g
<220> FEATURE:
<221> NAME/KEY: misc_feature
<222> LOCATION: (30)..(30)
<223> OTHER INFORMATION: n is c or t
<220> FEATURE:
<221> NAME/KEY: misc_feature
<222> LOCATION: (33)..(33)
<223> OTHER INFORMATION: n is c or t

<400> SEQUENCE: 34
cctggtcgta ctganaanga nattaanaan tantggaa                             38

<210> SEQ ID NO 35
<211> LENGTH: 22
<212> TYPE: DNA
<213> ORGANISM: Arabidopsis thaliana

<400> SEQUENCE: 35
atgggaaggt ctccttgctg tg                                              22

<210> SEQ ID NO 36
<211> LENGTH: 22
<212> TYPE: DNA
<213> ORGANISM: Arabidopsis thaliana

<400> SEQUENCE: 36
tcatttcatt tccaaagtgc ta                                              22

<210> SEQ ID NO 37
<211> LENGTH: 217
<212> TYPE: PRT
<213> ORGANISM: Brassica napus

<400> SEQUENCE: 37

Met Gly Arg Ser Pro Cys Cys Glu Lys Asp His Thr Asn Lys Gly Ala
1               5                   10                  15

Trp Thr Lys Glu Glu Asp Asp Leu Ile Ile Lys Leu His Ser Leu Leu
            20                  25                  30

Gly Asn Lys Trp Ser Leu Ile Ala Thr Arg Leu Pro Gly Arg Thr Asp
        35                  40                  45

Asn Glu Ile Lys Asn Tyr Trp Asn Thr His Val Lys Arg Lys Leu Leu
    50                  55                  60

Arg Gly Gly Ile Asp Pro Thr Thr His Arg Pro Ile Asn Glu Ala Lys
65                  70                  75                  80

Ala Pro Arg Asp Ser Ser Glu Thr Arg Glu Thr Glu Asp Ser Leu Val
```

```
                    85                  90                  95
Lys Phe Leu Ser Phe Ser Arg Gln Leu Glu Lys Glu Ser Phe Gly
            100                 105                 110

Glu Glu Arg Asn Asp Gln Lys Gly Leu Ile Cys Lys Lys Glu Arg Val
            115                 120                 125

Glu Tyr Ser Ile Val Glu Glu Lys Cys Leu Asp Leu Asn Leu Glu Leu
            130                 135                 140

Arg Ile Ser Pro Pro Trp Gln Asp Gln Gln His His Asp Glu Thr Lys
145                 150                 155                 160

Leu Trp Phe Gly Lys Glu Lys Tyr Met Cys Thr Ala Cys Arg Phe Gly
                165                 170                 175

Leu Gly Asn Gly Lys Lys Cys Ser Cys Asp Asn Val Lys Cys Gln Val
                180                 185                 190

Glu Tyr Ser Ser Ser Ser Ser His Ser Ser Ser Asp Ile Ser Ser
                195                 200                 205

Ser Val Ile Gly Tyr Asp Phe Leu Gly
            210                 215

<210> SEQ ID NO 38
<211> LENGTH: 662
<212> TYPE: DNA
<213> ORGANISM: Brassica napus

<400> SEQUENCE: 38
tgataagctt atgggaaggt ctccttgctg tgagaaggac cacacgaaca aaggagcttg      60
gactaaagaa gaagacgatc tcatcatcaa actccatagc ctccttggaa acaaatggtc    120
tcttatcgcg acgagattac cggggagaac agataacgag atcaagaact actggaatac    180
acacgtaaag aggaagcttt tgagaggagg gattgatccc acgactcatc ggccgatcaa    240
cgaagccaaa gctcctcgtg attcgtctga gactagagag acagaggact cgcttgtgaa    300
gtttctatct ttcagtcgtc aactggagaa aaaggaaagt tttggggaag agagaaatga    360
tcagaaagga ctgatttgca aaaagagag agttgagtat tcgattgttg aagaaaagtg    420
cttagatttg aatcttgagc ttagaatcag cccgccatgg caagaccaac agcaccatga    480
tgagaccaaa ctttggtttg ggaaagagaa gtacatgtgc actgcatgcc gttttgggtt    540
gggaaacggc aagaagtgta gctgcgataa tgttaaatgt caagtcgagt acagtagtag    600
cagcagcagc cattcttcaa gcgatattag tagtagcgtt attggttatg acttcttggg    660
ta                                                                   662

<210> SEQ ID NO 39
<211> LENGTH: 17
<212> TYPE: DNA
<213> ORGANISM: Artificial
<220> FEATURE:
<223> OTHER INFORMATION: Universal primer used for sequencing in pGEM
      and pBluescript vectors

<400> SEQUENCE: 39
gtaaaacgac ggccagt                                                    17

<210> SEQ ID NO 40
<211> LENGTH: 16
<212> TYPE: DNA
<213> ORGANISM: Artificial
<220> FEATURE:
<223> OTHER INFORMATION: Universal primer used for sequencing in pGEM
      and pBluescript vectors
```

```
<400> SEQUENCE: 40
aacagctatg accatg                                                     16

<210> SEQ ID NO 41
<211> LENGTH: 20
<212> TYPE: DNA
<213> ORGANISM: Artificial
<220> FEATURE:
<223> OTHER INFORMATION: pBl 101 primer used for sequencing and
      amplification

<400> SEQUENCE: 41
tgtggaattg tgagcggata                                                 20

<210> SEQ ID NO 42
<211> LENGTH: 20
<212> TYPE: DNA
<213> ORGANISM: Artificial
<220> FEATURE:
<223> OTHER INFORMATION: pBl 101 primer used for sequencing and
      amplification

<400> SEQUENCE: 42
attccacagt tttcgcgatc                                                 20

<210> SEQ ID NO 43
<211> LENGTH: 20
<212> TYPE: DNA
<213> ORGANISM: Arabidopsis thaliana

<400> SEQUENCE: 43
gaaagaagaa atgggtcgga                                                 20

<210> SEQ ID NO 44
<211> LENGTH: 20
<212> TYPE: DNA
<213> ORGANISM: Arabidopsis thaliana

<400> SEQUENCE: 44
caaccacttc tcccttcagc                                                 20

<210> SEQ ID NO 45
<211> LENGTH: 32
<212> TYPE: DNA
<213> ORGANISM: Artificial
<220> FEATURE:
<223> OTHER INFORMATION: Oligonucleotide to AtMYB103 including a Sal I
      restriction site.

<400> SEQUENCE: 45 ggggggtcg acatgggtcg gattccatgt tg                                   32

<210> SEQ ID NO 46
<211> LENGTH: 30
<212> TYPE: DNA
<213> ORGANISM: Arabidopsis thaliana

<400> SEQUENCE: 46
ggggaagctt tcctcctcct cgtgcgcggt                                      30

<210> SEQ ID NO 47
<211> LENGTH: 20
<212> TYPE: DNA
<213> ORGANISM: Arabidopsis thaliana

<400> SEQUENCE: 47
```

```
taaaaatcaa accatatgat                                                    20

<210> SEQ ID NO 48
<211> LENGTH: 21
<212> TYPE: DNA
<213> ORGANISM: Brassica napus

<400> SEQUENCE: 48
ttaaagagag acgatcgaga g                                                  21

<210> SEQ ID NO 49
<211> LENGTH: 20
<212> TYPE: DNA
<213> ORGANISM: Brassica napus

<400> SEQUENCE: 49
ctatttggcg tcctggacct                                                    20

<210> SEQ ID NO 50
<211> LENGTH: 23
<212> TYPE: DNA
<213> ORGANISM: Brassica napus

<400> SEQUENCE: 50
ccaatgggat ccaaaatgaa tca                                                23
```

NUCLEIC ACID MOLECULES AND THEIR USE IN PLANT STERILITY

This application is a division of U.S. application Ser. No. 11/494,919, filed Jul. 28,2006, now U.S. Pat. No. 8,163,975, U.S. application Ser. No. 11/494,919 is a continuation in part of PCT/AU05/00851, filed jun. 15,2005, which claims foreign priority to 2004903246, filed Jun. 15,2004.

The present invention relates to nucleic acid molecules. More particularly, the invention relates to genes involved in pollen formation and genetic methods for producing male sterile plants using constructs which disrupt expression of such genes. The invention further relates to the constructs used and transgenic plants transformed by the constructs.

BACKGROUND OF THE INVENTION

Heterosis is the term used to describe the superior performance of F1 hybrids over parental lines from which the F1 is derived. In crop plants heterosis often manifests in the production of larger plants, tolerance to stress, disease resistance, uniformity and improved yield, which are collectively referred to as hybrid vigour.

Heterosis has been observed and documented in many important crop species and the development of hybrids by plant breeders is established practice. However, hybrids can only be used in crops when effective and economical means of pollination control exist to ensure cross pollination and prevent self-pollination. Pollination control mechanisms include mechanical, chemical and genetic means.

A mechanical means for hybrid plant production can be used if the plant of interest has spatially separate male and female flowers or separate male and female plants. For example, a maize plant has pollen-producing male flowers in an inflorescence at the apex of the plant, and female flowers in the axiles of leaves along the stem. Outcrossing of maize is assured by mechanically detasseling the female parent to prevent selfing. Even though detasseling is currently used in hybrid seed production for plants such as maize, the process is labor-intensive and costly, both in terms of the actual detasseling cost and yield loss as a result of detasseling the female parent. Further, most major crop plants have both functional male and female organs within the same flower, and therefore emasculation is not a simple procedure. While it is possible to remove by hand the pollen forming organs before pollen is shed, this form of hybrid production is extremely labor intensive and expensive.

Chemical means of producing hybrid plants involves the use of chemicals that kill or block viable pollen formation. These chemicals, termed gametocides, are used to impart a transitory male-sterility. Commercial production of hybrid plants by use of gametocides is limited by the expense and availability of the chemicals and the reliability and length of action of the applications. A serious limitation of gametocides is that they have phytotoxic effects, the severity of which are dependent on genotype. Other limitations include that these chemicals may not be effective for crops with an extended flowering period because new flowers produced may not be affected. Consequently, repeated application of chemicals is required.

Many current commercial hybrid plant production systems for field crops rely on a genetic means of pollination control. In such systems, plants that are used as females either fail to make pollen, fail to shed pollen, or produce pollen that is biochemically unable to effect self-fertilization. Plants that are unable to self-fertilize are said to be "self-incompatible" (SI). Difficulties associated with the use of a self-incompatibility system include availability and propagation of the self-incompatible female line, and stability of the self-compatibility. In some instances, self-incompatibility may be overcome chemically, or immature buds can be pollinated by hand before the biochemical mechanism that blocks pollen is activated. Self-incompatible systems that can be deactivated are often very vulnerable to stressful climatic conditions that break or reduce the effectiveness of the biochemical block to self-pollination.

Genetic systems involving cytoplasmic or nuclear genes may be used to generate male sterility. Cytoplasmic male sterility (CMS) is at present the most widely used mechanism of pollen control in crops. However, CMS has a number of disadvantages including increased disease susceptibility, breakdown of sterility under certain conditions, undesirable characters linked to restorer genes (genes that can suppress the male-sterile effect of the cytoplasm and are incorporated into the male parent to restore pollen fertility in the F1 hybrid), unreliable restoration, etc. Crops in which such problems occur are, for example, maize, oilseed rape and wheat.

Consequently, plant breeders and seed producers require a versatile and durable male sterility system. The genetic engineering approach has a number of advantages over natural systems. The disruption of the genotype of new male-sterile plants normally associated with the introduction of sterility by sexual means is completely avoided and sterility is not linked to particular cytoplasms as in cytoplasmic male sterility.

Nuclear-encoded male sterility (NMS) is caused by mutations in the nuclear genome. The advent of plant genetic engineering technology has now made it feasible to develop strategies to permit the use of NMS genes.

Plant breeders and seed producers require a versatile and durable male sterility system. The problems that must be overcome include the isolation of genes that induce male sterility, the production of 100% male-sterile progeny, the achievement of complete female fertility and subsequent restoration of pollen fertility in the F1 hybrid.

An aim of the present invention is to determine gene(s) involved in pollen formation and develop methods of preventing pollen formation by disrupting the expression or activity of the gene(s) or their gene product(s). A further aim of the present invention is to develop a method for the production of transgenic male sterile plants and/or seeds and harvest plants and/or seeds so produced.

SUMMARY OF THE INVENTION

Accordingly the present invention provides in a first aspect a method for disrupting pollen development in a plant, the method comprising inhibiting the expression of an endogenous nucleic acid molecule which is, under normal conditions, detectably expressed in anther tissue of a plant during pollen formation, and which codes for a protein belonging to the MYB class of DNA binding transcription factors.

Preferably the nucleic acid molecule whose expression is blocked encodes MYB 32 or MYB 103. Preferably MYB32 has the amino acid sequence provided in FIG. 1 or is a homologue, orthologue or derivative thereof having at least 50% similarity to the amino acid sequence of FIG. 1 and which capable of being detectably expressed in anther tissue of a plant during pollen formation, and which codes for a protein belonging to the MYB class of DNA binding transcription factors.

The invention extends to ortholgues of MYB32, including that from *Brassica napus*, where BnMYB32 has the amino acid sequence provided in FIG. 1 (SEQ ID NO 1), *Arabidop-*

*sis thaliana*, where AtMYB32 has the amino acid sequence provided in FIG. 4 (SEQ ID NO. 7), tomato, where TmH27 has the amino acid sequence provided in FIG. 5a (SEQ ID NO. 9), cotton, where GhMYB9 has the amino acid sequence provided in FIG. 5b (SEQ ID NO 10), *Zea mays*, where ZmMYB32-1 has the amino acid sequence provided in FIG. 7a (SEQ ID NO. 12) and ZmMYB32-2 has the amino acid sequence provided in FIG. 7b (SEQ ID NO. 13), *Hordeum vulgare*, where HvMYB32 has the amino acid sequence provided in FIG. 7c (SEQ ID NO. 14), *Nicotiana tabacum*, where TaMYB32 has the amino acid sequence provided in FIG. 7d (SEQ ID NO. 15) or *Triticum aestivum*, where TaMYB32 has the amino acid sequence provided in FIG. 36 (SEQ ID NO. 17).

The invention also extends to orthologues of MYB103, including *Brassica napus*, where BnMYB 103-1 has the amino acid sequence provided in FIG. 2 (SEQ ID NO. 3) and BnMYB103-2 has the amino acid sequence provided in FIG. 3 (SEQ ID NO. 5), *Arabidopsis thaliana*, where AtMYB103 has the amino acid sequence provided in FIG. 11 (SEQ ID NO. 22), rice, where OsMYB103 has the amino acid sequence provided as FIG. 6 (SEQ ID NO. 11) or FIG. 37 (SEQ ID NO. 18), or *Triticum aestivum*, where TaMYB103 has the amino acid sequence provided in FIG. 38 (SEQ ID NO. 20).

Expression of the endogenous nucleic acid molecule may be effected by sense or co-suppression technology, for example by antisense RNA interference technology.

The disruption of pollen formation according to the first aspect, of the invention may induce male sterility in plants. In a preferred embodiment the induction of male sterility is inducible and reversible. The use of a reversible repressor system is particularly preferred.

To bring about 100% male sterility it may be necessary to block expression of nucleic acid molecules encoding both MYB 32 and MYB 103. This is particularly the case for *Arabidopsis thaliana*.

In a second aspect the invention provides an isolated nucleic acid molecule capable of blocking expression of a gene encoding MYB32 having the amino acid sequence provided in FIG. 1 or an orthologue thereof having at least 50% sequence homology to the amino acid sequence provided in FIG. 1, which MYB32 gene or orthologue are detectably expressed in anther tissue during pollen formation.

In a preferred embodiment the MYB32 gene comprises the nucleotide sequence provided in FIG. 1 (SEQ ID NO. 2), 4 (SEQ ID NO. 8), or FIG. 36 (SEQ ID NO. 16) or a sequence complementary or antisense thereto, or a fragment of the nucleotide sequence or its complement, which nucleic molecule is capable of blocking expression of the gene encoding MYB32.

In a third aspect the invention provides an isolated nucleic acid molecule capable of blocking expression of a gene encoding MYB103 having the amino acid sequence provided in FIG. 2 or FIG. 3 or an orthologue thereof having at least 50% sequence homology to the amino acid sequence provided in FIG. 2 or FIG. 3, which MYB103 gene or orthologue are detectably expressed in anther tissue during pollen formation.

In a preferred embodiment the MYB103 gene comprises the nucleotide sequence provided in FIG. 2 (SEQ ID NO. 4), 3 (SEQ ID NO. 6), 37 (SEQ ID NO. 19) or FIG. 38 (SEQ ID NO. 21) or a sequence complementary or antisense thereto, or a fragment of the nucleotide sequence or its complement, which nucleic molecule is capable of blocking expression of the gene encoding MYB103.

The MYB103 or MYB32 genes according to the second and, or third aspects of the invention may be provided in a nucleic acid construct. The construct may further comprise a promoter capable of targeting expression of the nucleic acid molecule in the construct to the anther, preferably during pollen formation. The construct may further comprise means for controlling the expression of the gene(s). Preferably such means comprises a dominant repression motif, for example the motif LXLXLX (the EAR motif described by Hiratsu et al., 2003 Plant J. 35, 177-192).

The construct may comprise both a MYB32 and a MYB103 gene, or more than one copy of the, or each, gene. The construct may further comprise one or more additional genes involved in male specific development, such as the AtMYB103 gene shown in FIG. 12 (SEQ ID NO. 23). The construct may comprise an inducible promoter.

In a fourth aspect the invention provides a plant cell transformed with the isolated nucleic acid molecule according to the second or third aspect of the invention or a construct comprising such nucleic acid molecule.

In a fifth aspect the invention provides a transgenic plant generated from the plant cells according to the fourth aspect of the invention. Also encompassed are the progeny of such plants and seeds, tissues, roots, shoots, tubers or propagating material of such transgenic plants or their progeny.

The nucleic acid molecules according to the second and third aspects of the invention find particular utility in the production of male sterile plants.

In a sixth aspect the invention provides a male sterile plant in which expression of an endogenous nucleic acid molecule is blocked, which nucleic acid molecule is, under normal conditions, detectably expressed in anther tissue of a plant during pollen formation, and which codes for a protein belonging to the MYB class of DNA binding transcription factors.

In a preferred embodiment of the sixth aspect expression of one or more endogenous genes is blocked using a nucleic acid molecule according to the second or third aspect of the invention or a nucleic acid construct comprising said nucleic acid molecule.

The male sterile plant may be monocotyledonous or dicotyledonous. The invention is particularly suitable to legumes, crops, cereals, native grasses, fruiting plants or flowering plants.

Preferred plants include Brassicaceae or other Solanaceae species, including potato and cole vegetables, cabbage, kale, collards, turnips, rutabaga, kohlrabi, Brussels sprouts, broccoli and cauliflower, mustards and oilseeds, crucifers, broccoli, canola, tomato, grain legumes, wheat, barley, maize, tobacco and rice.

Reversible male sterility is critical for the production of hybrid plant varieties that exhibit a higher yield than either of the parents. In particular the present invention enables regulation of plant genes by turning off the endogenous gene encoding MYB 32 or MYB 103 in a female parental line but turning on the endogenous equivalent of a the gene on the hybrid that results from crossing the female parental line with another line.

BRIEF DESCRIPTION OF THE FIGURES

FIG. 1 provides the nucleic acid sequence (SEQ ID NO. 2) and proposed amino acid sequence (SEQ ID NO. 1) of BnMYB32.

FIG. 2 provides the nucleic acid sequence (SEQ ID NO. 4) and proposed amino acid sequence (SEQ ID NO. 3) of BnMYB103-1. Conserved amino acids are indicated by underscore.

FIG. 3 provides the nucleic acid sequence (SEQ ID NO. 6) and proposed amino acid sequence (SEQ ID. NO. 5) of BnMYB103-2.

FIG. 4 provides the nucleic acid sequence (SEQ ID. 8) and proposed amino acid sequence (SEQ ID NO. 7) of AtMYB32. No known plant transcription elements were identified in the promoter region of AtMYB32. The Bbsl sites are shown underlined, as is the putative TATA consensus sequence. The conserved amino acid sequences found in the carboxyl region of other plant MYB-related proteins are shown underlined.

FIG. 5 provides the proposed amino acid sequences of (a) TmH27 (SEQ ID NO. 9) and (b) GhMYB9 (SEQ ID NO. 10).

FIG. 6 provides the proposed amino acid sequence of OsMYB103 (SEQ ID NO. 11).

FIG. 7 provides the proposed amino acid sequence of (a) ZzmMYB32-1, SEQ ID NO. 12 (b) ZmMYB32-2, (SEQ ID NO. 13) (c) HvMYB32 (SEQ ID NO. 14) and (d) TaMYB32 (SEQ ID NO. 15).

FIG. 11 shows the AtMYB103 (SEQ ID NO. 22) and p8.1.1 CLUSTAL X (1.8) sequence alignment. Both sequences contain conserved tryptophan and phenylalanine residues typical of the R2R3 repeat regions of plant MyB genes (indicated by underscore).

FIG. 12 shows the AtMYB103 (SEQ ID NO. 23) and BnMYB103-1 (SEQ ID NO. 4) CLUSTAL X (1.8) sequence alignment. Arrow heads indicate conserved intron sites.

FIG. 13 shows the BnMYB103-1 (SEQ ID NO. 3) amino acid sequence indicating conserved amino acids by underscore.

FIG. 14 shows the AtMYB103 (SEQ ID NO. 22) and BnMYB103-1 (SEQ ID NO. 3) CLUSTAL X (1.8) sequence alignment.

FIG. 16 shows the AtMYB103 (SEQ ID NO. 22) and p700-1 (SEQ ID NO. 24) CLUSTAL X (1.8) sequence alignment.

FIG. 18 shows the AtMYB103 (SEQ ID NO. 22) and p800-19 (SEQ ID NO. 25) CLUSTAL X (1.8) sequence alignment.

FIG. 20 shows the AtMYB103 (SEQ ID NO. 22) and P900-10 (SEQ ID NO. 26) CLUSTAL X (1.8) sequence alignment.

FIG. 21 shows the AtMYB103 (SEQ ID NO. 22), BnMYB103-1 (SEQ ID NO. 3), p700-1 (SEQ ID NO. 24), p800-19 (SEQ ID NO. 25) and P900-10 (SEQ ID NO. 26) CLUSTAL X (1.8) multiple sequence alignment. All sequences contain conserved tryptophan and phenylalanine residues typical of the R2R3 repeat regions in plant MYB genes (indicated by underscore. Differences in the amino acid sequences are highlighted.

FIG. 22 shows A —AtMYB103 promoter —gusA in A. thaliana (Bar =15mm). B- BnMYB103-1 promoter —gusA in A. thaliana (Bar =25 mm).

FIG. 28 shows TA39 promoter GUS expression. A shows TA39::gusA expression in *A. thaliana* (Bar =25 mm). B shows TA39::gusA expression in *B. napus* (Bar =2 mm).

A & B show sense and antisense BnMYB103-1 constructs cloned into pBluescipt with the TA39 promoter.

C shows restriction enzyme digests (PvuII & SnaBI) of two clones, indicating the sense orientation in lane 2 (expect fragments of 2513 by —vector, 2512 by & 475 bp) and antisense orientation in lane 3 (expect fragments of 2513 by —vector, 2171 by & 816 bp).

Figure 30:
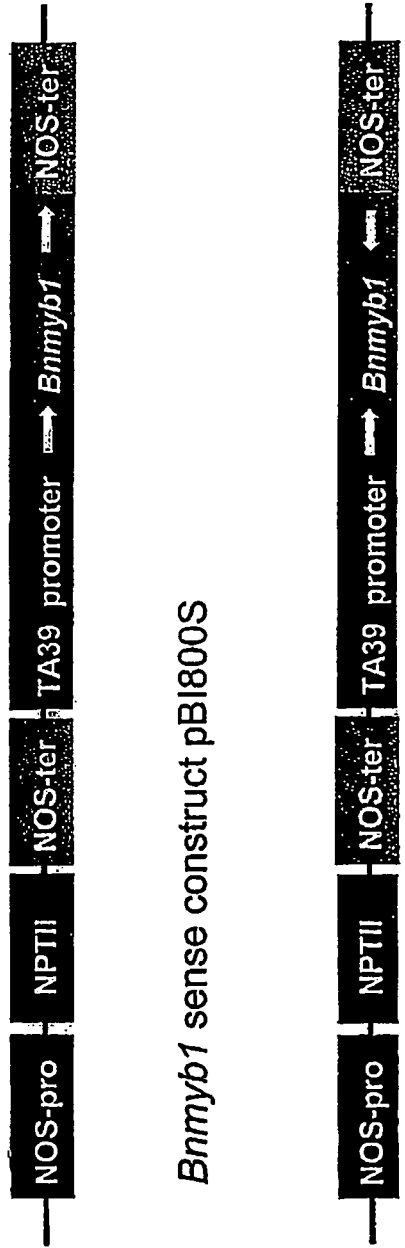

FIG. 30 shows BnMYB103-1 (SEQ ID NO. 4) sense and antisense constructs. NOS pro indicates nopaline synthase promoter, FPTII indicates neomycin phosphotransferase II and NOS-ter indicates nopaline synthase terminator.

Figure 31:
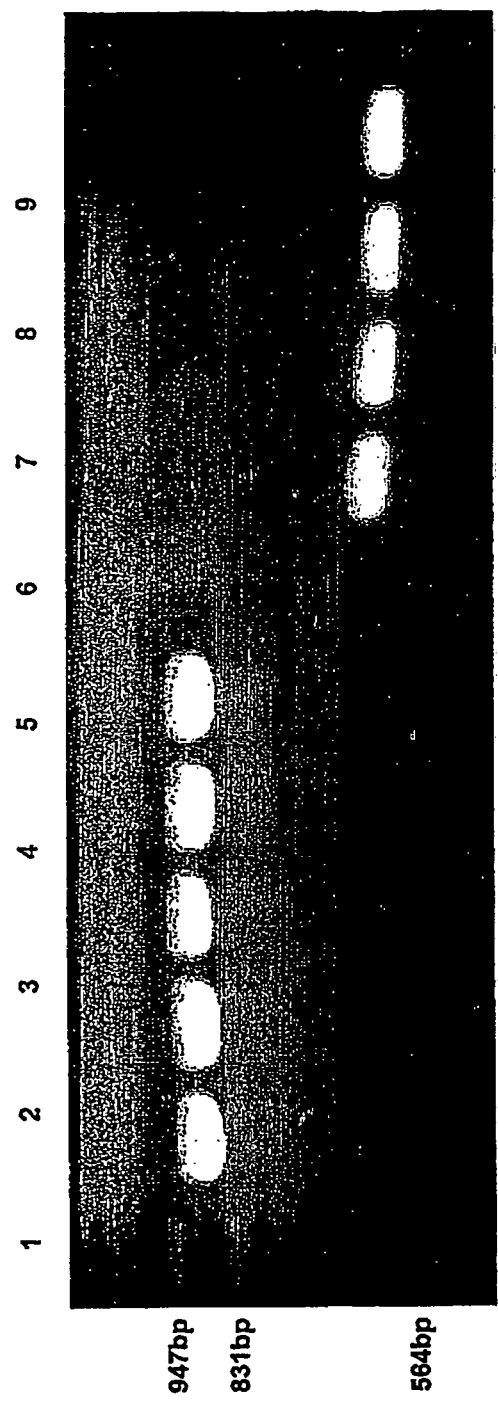

FIG. 31 shows PCR analysis of *A. thaliana* plants transformed with sense and antisense BnMYB103-1 (SEQ ID NO. 4) constructs.

Lane 1 molecular weight markers
Lanes 2-6 PCR products generated from plants transformed with antisense constructs using primers P30 & P32 (903 bp)
Lanes 7-11 PCR products generated from plants transformed with sense constructs using primers P30 & P34 (636 bp).

Figure 32A:
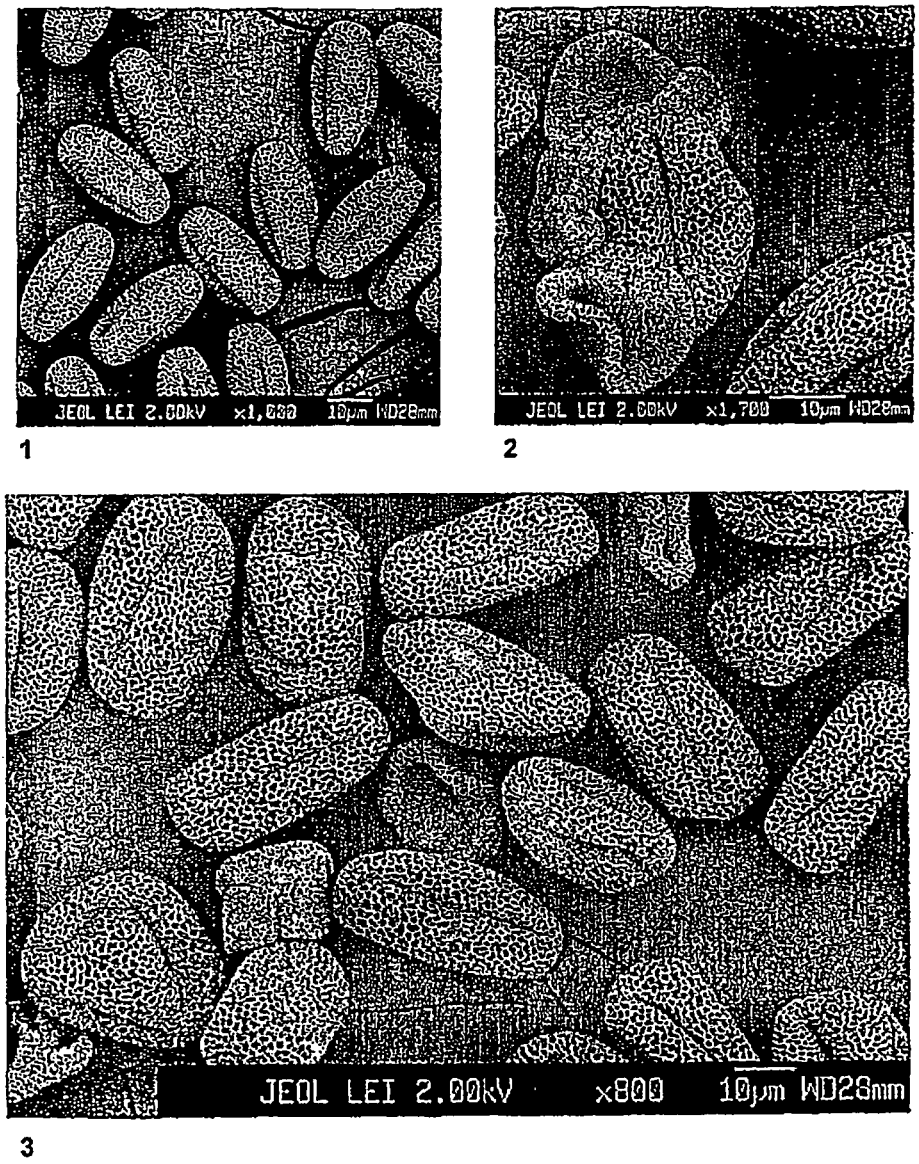

FIG. 32a shows scanning electron micrographs of pollen from *A. thaliana* wild type and BnMYB103-1 (SEQ ID NO. 4) transgenic plants.
1 shows wild type pollen grains
2 gives detail showing flattened pollen grains from AS22
3 shows representative field of pollen from AS 15 showing abnormal grain shape and positioning of germinal apertures.

FIG. 32b shows scanning electron micrographs of pollen from *A. thaliana* BnMYB103-1 (SEQ ID NO. 4) transgenic plants. These panels show pollen from plants transgenic for the sense construct.
1 representative field of pollen from S11.
2 representative field of pollen from S20.

Figure 33:
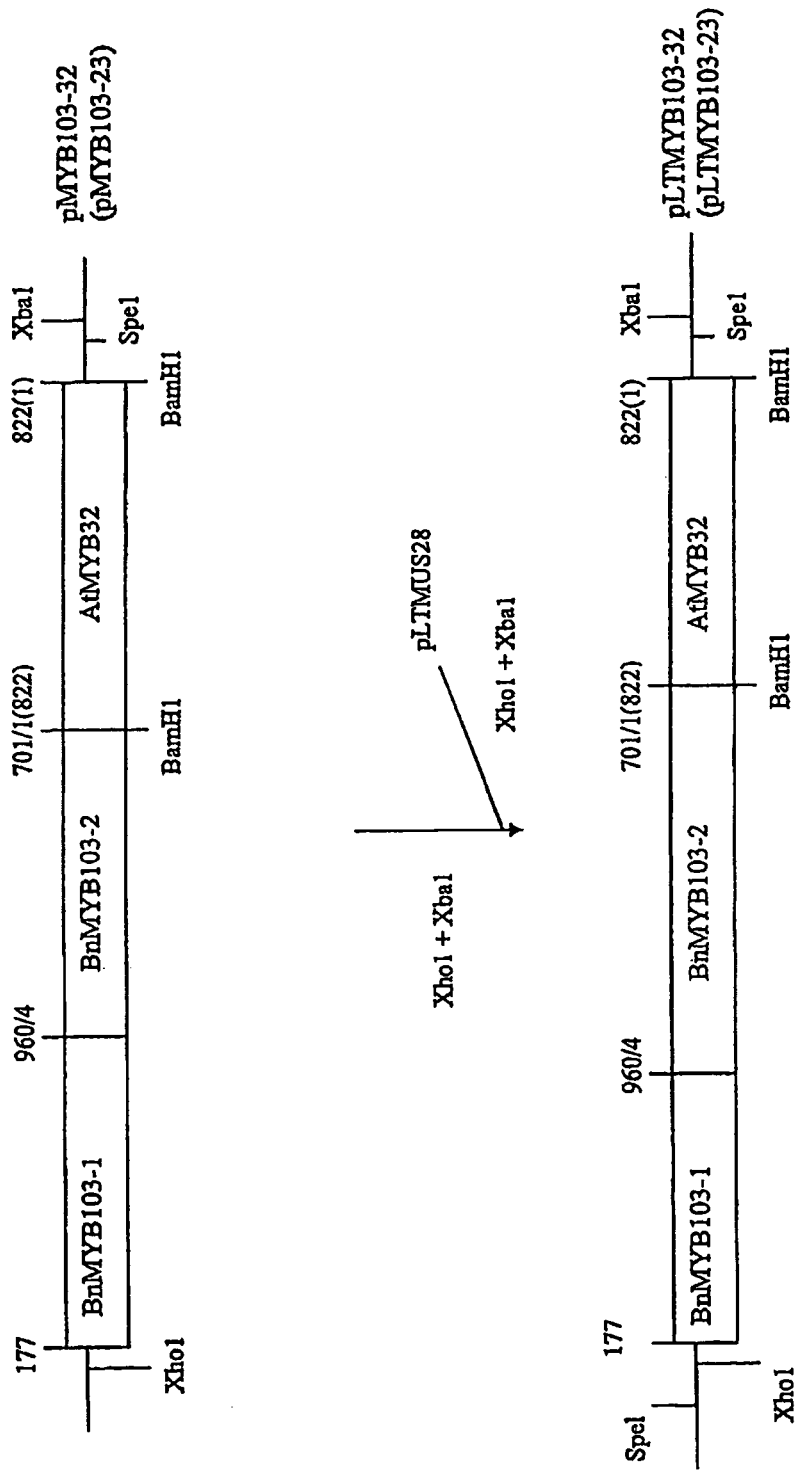
Figure 33:
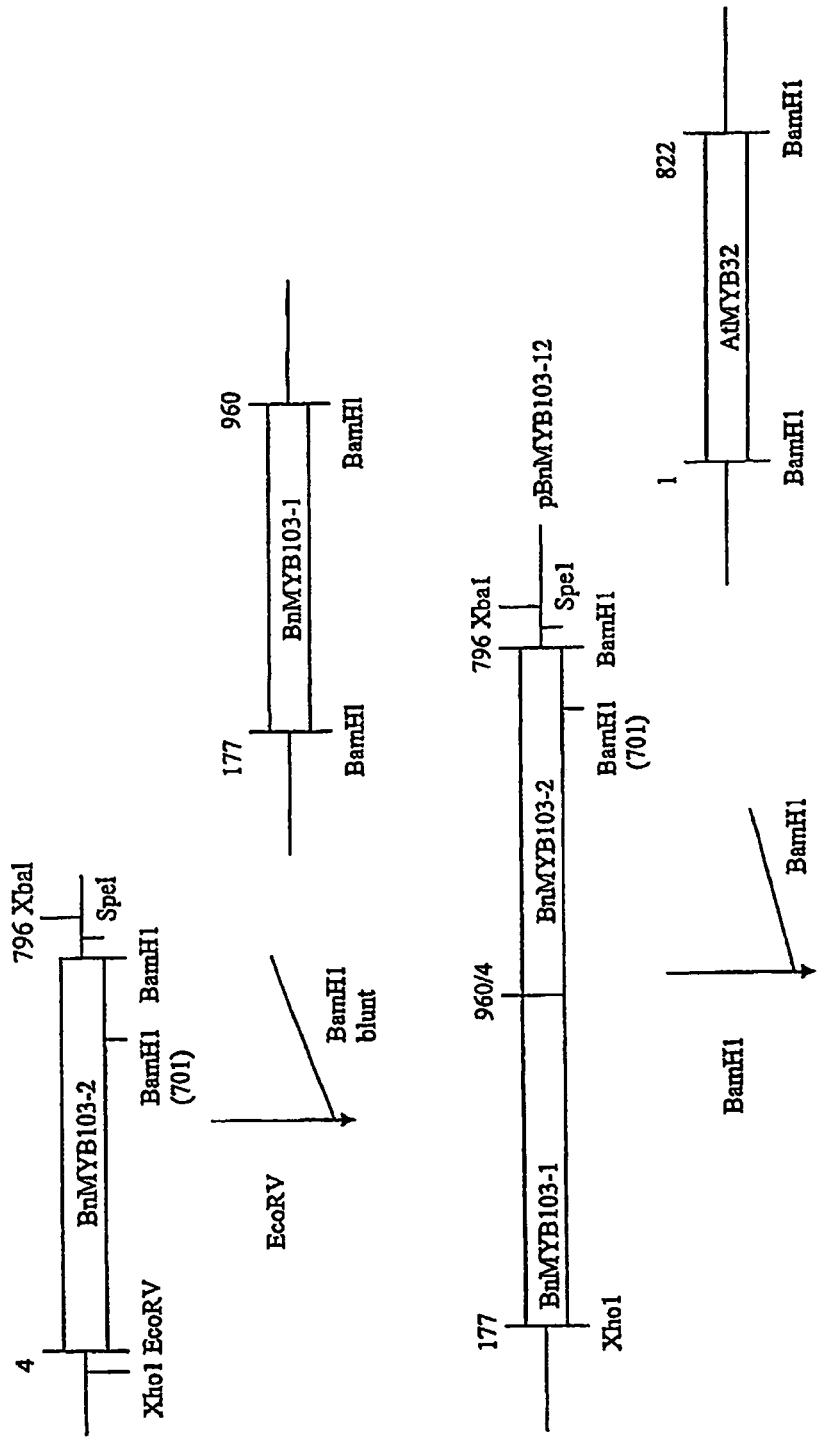

FIG. 33 shows production of a construct according to a preferred embodiment of the present invention.

Figure 34:
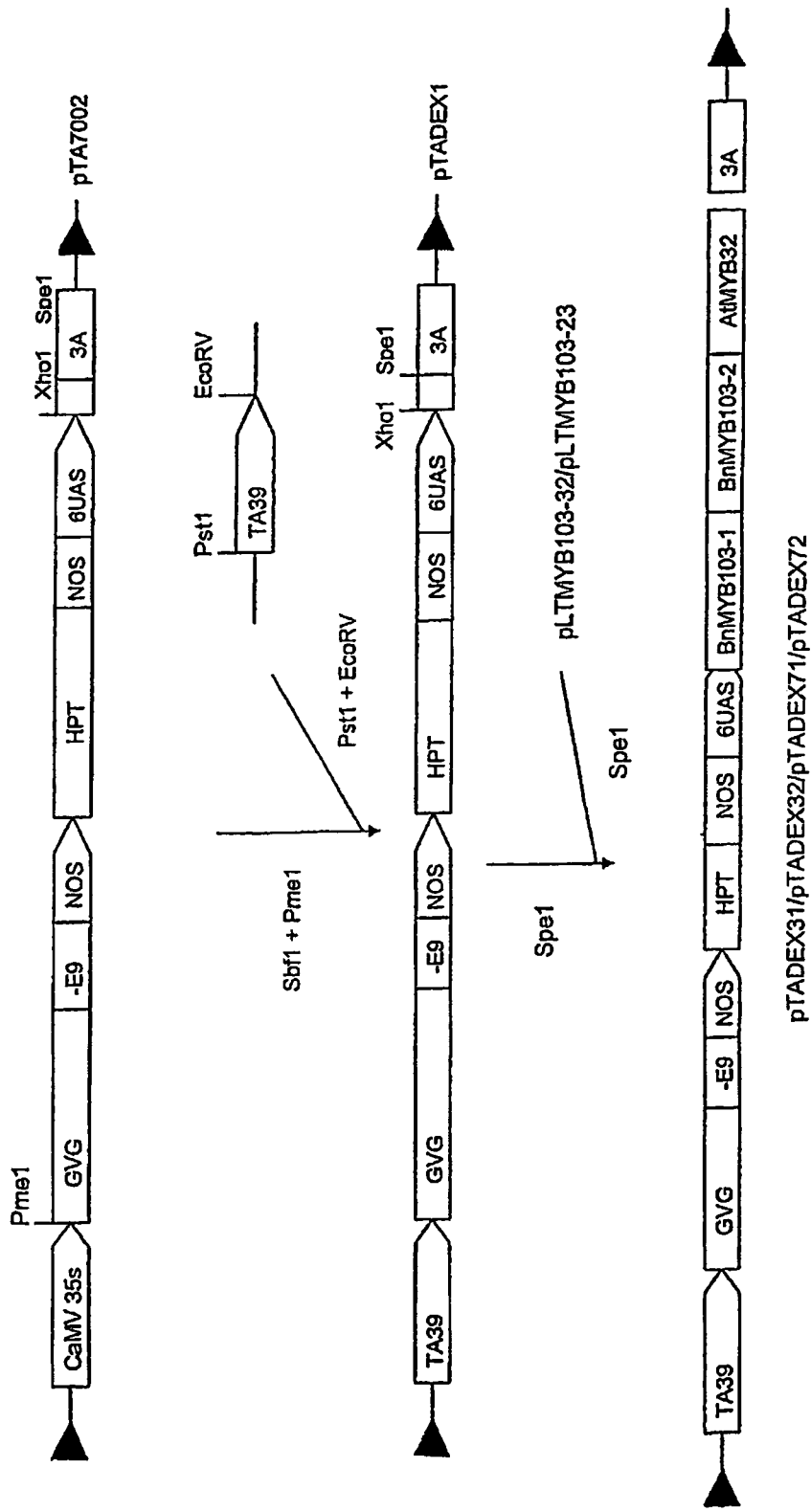

FIG. 34 shows production of a further construct according to a preferred embodiment of the present invention.

Figure 35:
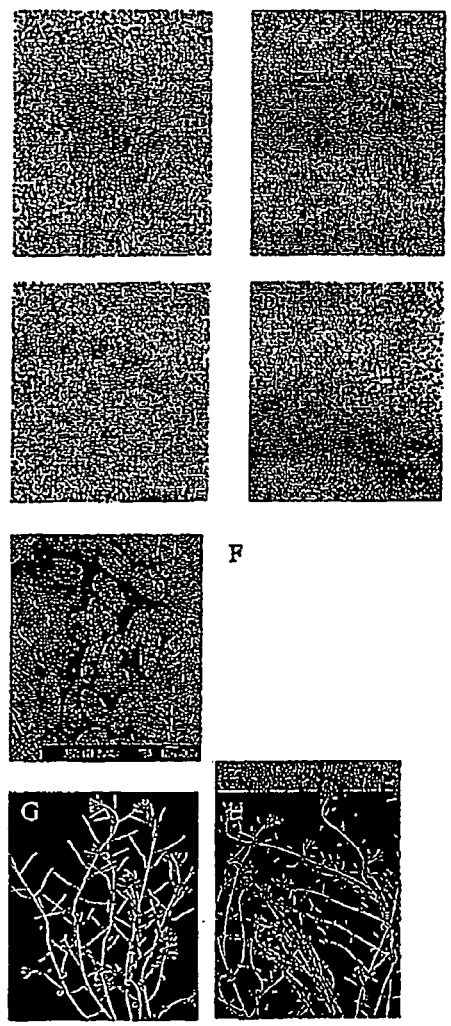

FIG. 35 A-H illustrate changes in phenotype in *A. thaliana* as a result of carrying out a method according to a preferred embodiment of the present invention.

FIG. 36 shows the nucleotide sequence of TaMYB32 (SEQ ID NO. 16) and the alignment of the deduced amino acid sequences of AtMYB32 (SEQ ID NO. 7) and TaMYB32 (SEQ ID NO. 17). The MYB domain sequences are marked in bold letters and the identical amino acids are underlined. The gaps introduced for optimal alignment are represented by broken lines.

FIG. 37 shows the putative rice AtMYB103 (SEQ ID NO. 22) orthologue, OsMyB103 (SEQ ID NO. 19). Sequence was obtained from Genbank. Introns are shown in lower case and amino acid sequence (SEQ ID NO. 18) is shown below the nucleotide sequence. In the alignment shaded boxes show the position of primers. Conserved MYB repeats R2 and R3 are underlined. Conserved residues important for protein folding are shown in bold. Note —sections of low homology (between 168 and 306 in the eAtMyB103 protein) are not shown.

FIG. 38 shows an alignment of the deduced amino acid sequences of AtMYB103 (SEQ ID NO. 22) and TaMYB103 (SEQ ID NO. 20) fragments and a partial nucleotide sequence of the wheat TaMYB103 gene (SEQ ID NO. 21). Identical amino acids in the alignment are underlined.

Figure 39:
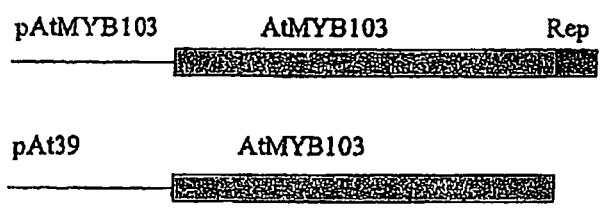

FIG. 39 shows the structure of repressor (top) and restorer (bottom) constructs. The promoters are represented by the lines and the AtMYB103 gene (SEQ ID NO. 23) by light shading, and the repression motif by dark shading.

Figure 40:
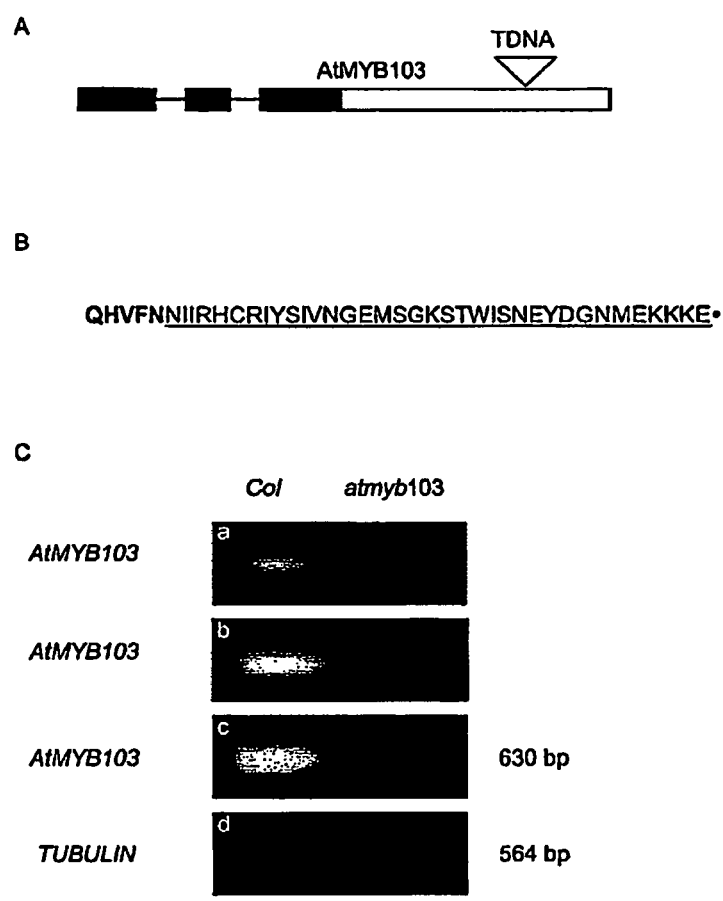

FIGS. 40A-C illustrate the structure of AtMYB103 and shows RT-PCR analysis of AtMYB103 transcript. FIG. 40A shows the structure of AtMYB103 in the insertion mutant. Boxes represent exons and lines introns. Filled boxes indicate the region coding for the MYB domain and a triangle the T-DNA insertion site. In FIG. 40B the amino acid sequence in frame with AtMYB103 sequence (SEQ ID NO. 22) at the insertion site is shown and the sequence encoded by the T-DNA underlined. FIG. 40C RT-PCR analysis of RNA extracted from the developing florets of wild-type (Col) and the AtMYB103 insertion mutant plants. PCR amplifications of AtMYB103 transcripts were carried out for 32 cycles (a), 34 cycles (b) and 36 cycles (c), respectively. The β-tubulin transcript was amplified for 24 cycles.

FIGS. 41a-41e shows silique elongation and pollen morphology of wild-type and insertion mutant plants. (a) shows elongated siliques in a wild-type inflorescence (Columbia) and aborted siliques in a mutant inflorescence. (b) shows Alexander's stainin (Alexander, M.P. (1969) Stain Technol. 44, 117-122) of a wild type anther and (c) a mutant anther. (d) shows scanning electron micrographs of pollen from a wild-type plant and (e) from a mutant plant. Scale bar =10 μm.

FIGS. 42a-42q shows sections of anthers from wild-type and insertion mutant plants. A Flower sections of wild-type (a, c, e, g, i, k) and mutant (b, d, f, h, j, 1, m) plants were stained with safrinin and anther cross-sections were photographed. Developmental states were assigned according to Sanders et al. (1999) Sex. Plant Reprod. 11, 297-322. (a) and (b) show stage 5, (c) and (d) stage 6, (e) and (f) stage 7, (g) and (h) stage 8, (i) and (j) stage 9, (k) and (1) and (m) stage 12. Transmission electron micrographs of sections of a wild-type anther are shown in (n) and mutant anthers (o, p, q). (n) and (o) stage 6, (p) stage 7 and (q) stage 9. Pmc, pollen mother cell, td, tetrad; tp, tapetum; ms, microspore; cms collaspsed microspores; v, vacuole; dms degenerating microspores; pw, pollen wall; db, debris. Sale bars =10 μm.

FIGS. 43a-43d shows Silique elongation and pllen morthology of wild-type and repressor plants. A shows the structures of the repressors and the amino acid sequence at the fusion joint. Introns are represented by filled boxes, exons by empty boxes and promoters by lines. The C terminal sequence of AtMYB103 (SEQ ID NO. 22) and EAR sequence (SEQ ID NO: 27) are underlined. B shows elongated siliques in a wild-type plant (Columbia) (a) and aborted siliques in a P103/103EAR plant (b). Alexander's staining of a wild-type anther (c) and a P103/103EAR anther (d).

FIGS. 44a-44e shows sections of anthers from a repressor line. Flower sections of repressor plants were stained with safrinin and anther sections are shown. (a) stage 5, (b) stage 7, (c) stage 9 (longitudinal section), (d) stage 12 and (e) stage 13.

Figure 45:

FIG. 45 shows RT-PCR analysis of the repressor and endogenous AtMYB103 transcripts. The RNA samples were extracted from developing florets with closed buds of wild-type plants (lanes 1, 2), repressor lines 1, 2, 3 and 4 (lanes 3 and 4, 5 and 6, 7 and 8, 9 and 10), respectively. RT-PCR amplications were carried out using primers specific to endogenous AtMYB103 transcript (a), repressor transcript (b) and β-tubulin transcript (c). The PCR reactions (a, b) were terminated at cycles 31 (lanes 1, 3, 5, 7, 9) and 35 (lanes, 2, 4, 6, 8, 10). The PCR reactions (c) were stopped at cycles 24 (lanes 1, 3, 5, 7, 9) and 27 (lanes 2, 4, 6, 8, 10). The primers in each reaction were positioned on either side of an intron to identify cDNA products.

Figure 46:
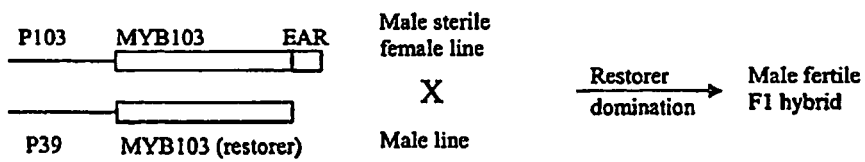

FIG. 46 shows a model for hybrid seed production. A male sterile female line transgenic for P103/103EAR is pollinated with pollen from a male line containing the restorer P39/103. The restorer out-competes the repressor in F1 hybrid resulting in the restoration of male fertility.

Figure 47:
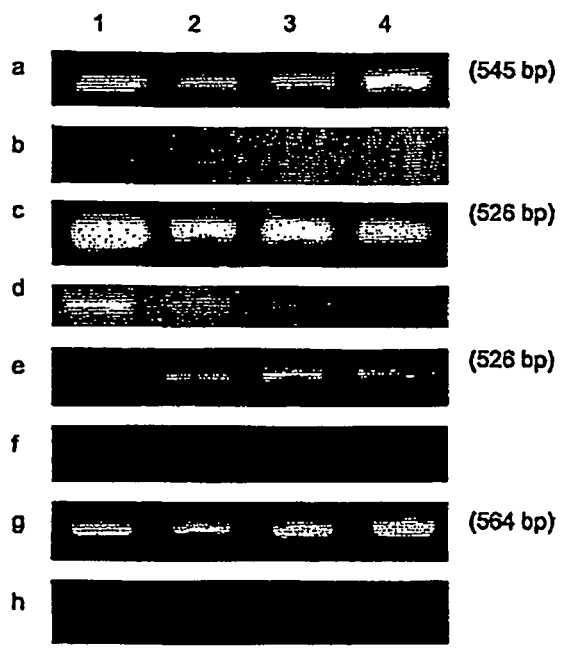

FIG. 47 shows RT-PCR analysis of the restorer and endogenous AtMYB103 transcripts. The RNA samples were extracted from developing florets with closed buds of restorer lines 1, 2, 3, and 4 (lanes 1, 2, 3, 4), respectively. The RNA samples were transcribed using a reverse transcriptase with the exception of the samples in (e) and (f). Endogenous AtMYB103 (a, b) and the restorer (c, d) transcripts were amplified for 28 cycles (b, d) and 32 cycles (a, c). The β-tubulin (g, h) transcript was amplified for 19 cycles (h) and 23 cycles (g). The control samples were subjected to PCR amplification without prior reverse-transcription for 28 cycles (f) and 32 cycles (e). Low levels of genomic restorer products (e, f) were detected.

FIGS. 48a-48c shows silique elongation of F1 plants. Male sterile P103/103EAR plants were pollinated with pollen from P39/103 plants and F1 silique elongation was examined. Partial restoration (a) and full restoration (b) of F1 silique elongation and aborted siliques (c) from parental male sterile plants.

FIGS. 49A-B shows the potential application of the MYB103EAR chimeric repressor in hybrid seed production. A —The inducible activator MYB103EcR and the chimeric repressor MYB103EAR are introduced into a female line together or separately. The male sterility caused by the 103EAR is reversed by the agonist-activated MYB103EcR. The resultant male sterile and homozygous female line is then pollinated by a male line containing a restorer MYB103RST. B—the inducible chimeric repressor MYB103EAREcR is transformed into a female line. Male sterility induced by an ecdysone agonist enables the female line to be pollinated by a male line. No restorer is required.

DETAILED DESCRIPTION OF THE INVENTION

The present invention relates to the identification by the inventors of certain genes which are expressed in the anthers of plants during pollen formation and their work showing that such genes are vital for pollen formation and thus may be blocked to produce male sterile plants.

The inventors' earlier research papers, Li et al., Plant Cell Physiol. 40(3); 343-347 (1999) and Higginson et al., The Plant Journal (2003) 35, 177-192 describe a MYB-like gene from *Arabidopsis*, AtMYB103. This gene was shown to be expressed in the anther during the early stages of anther development and was suggested to be involved in pollen formation. Unpublished work by the inventors showed that blocking of this gene alone in *Arabidopsis* was insufficient to produce 100% male sterility. Without 100% male sterility pollen is still able to be produced and accordingly heterosis may not be achieved.

Subsequent work described in this specification shows the discovery of an additional *Arabidopsis* gene expressed in anther tissue and involved in pollen formation. Provided herein is evidence that blocking the expression of both the *Arabidopsis* genes allows production of 100% male sterile *Arabidopsis* plants.

Additionally the inventors have sought to find if there are functional ortholgues of the *Arabidopsis* genes in other plant species and here describe several such orthologues and methods of inducing male sterility in crop species such as *Brassica* by blocking the expression of the endogenous gene corresponding to the orthologues.

"Nucleic acid" as used herein refers to an oligonucleotide, polynucleotide, nucleotide and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "nucleic acid" is used to refer to a specific nucleic acid sequence "nucleic acid" is meant to encompass polynucleotides that encode a polypeptide that is functionally equivalent to the recited polypeptide, e.g., polynucleotides that are degenerate variants, or polynucleotides that encode biologically active variants or fragments of the polypeptide, including polynucleotides having substantial sequence similarity or sequence identity relative to the sequences provided herein.

Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein.

By "isolated" we mean free from material present in nature in the plant from which the nucleic acid molecule is derived, that is in an environment different from that in which the compound naturally occurs. "Isolated" is meant to include compounds that are within samples that are substantially enriched for the compound of interest and/or in which the compound of interest is partially or substantially purified.

The nucleic acid molecules of the present invention are expressed in anther tissue during pollen formation. Whilst the nucleic acid molecules are not exclusively expressed in the anther, nor only during pollen development, these molecules are more specific than "house-keeping" genes which are active in all plant cells. The invention does not encompass genes that are not expressed in the anther during pollen development. For the avoidance of any doubt the present invention does not encompass the ZmMYBP2 gene, the NtMYBAS1 gene or the NtMYNAS2 gene. None of the prior art in relation to these genes describes that the gene is expressed in the anther during pollen development. The inventors' studies would tend to suggest that the ZmMYBP2 gene, the NtMYBAS1 gene, and the NtMYNAS2 gene are not expressed in the anther during pollen development. The prior art does not specifically disclose that the AtMYB103 gene is expressed in the anther during pollen development. The inventors have found that it is and have also found that blocking expression of this gene alone is not capable of producing 100% male sterility. Accordingly the present invention does not encompass the AtMYB103 gene, although it does encompass the use of the gene in inducing male sterility.

Preferably, the majority of the expression of the nucleic acid molecule during pollen development is in the anther. Such molecules may be considered "anther specific".

Anther tissue describes the tissue of the male reproductive organs in a plant, be it fully developed or partially developed. The definition of anther tissue used herein is intended to include all structures making up the anther, that is, the epidermis, endothecium, middle layer and tapetum.

The nucleic acid molecules according to the second and third aspects of the invention encode proteins belonging to the MYB class of DNA binding transcription factors. MYB (myeloblastosis) genes represent the largest family of transcription factors found in plants with around 180 MYB genes known in the genome of *A. thaliana*. The first MYB genes were isolated from avian leukaemia viruses and they have now been described in mice, *Drosophila melanogaster*, *Dictyostelium discoideum*, yeast and fungi. It has been estimated that over 5% of the *Arabidopsis* genome codes for transcription factors. This accounts for approximately 1700 genes of which 180 (10.6%) belong to the MYB family. Maize expresses over 80 MYB genes, it is estimated that petunia has at least 40, rice more than 20 and others have been reported in Antirrhinum, barley, pea, sorghum and the moss *Physcomitrella patens*. The majority of MYB genes found in plants are of the R2R3 type, although some exceptions have been reported. Genes with a single repeat unit have been found in potato and *Arabidopsis*.

The vertebrate family of MYB transcription factors consists of A-, B- and c-MYB and all three are involved in the regulation of cellular proliferation, differentiation and apoptosis. This is in contrast to the many MYB proteins found in plants, none of which have been found to share a similar function. A study aimed at the functional characterisation of R2R3MYB genes in *Arabidopsis* has shown that they are expressed in different organs (seedlings, young and mature leaves, cauline leaves, stem, flower buds, siliques and roots) and in response to a variety of environmental conditions (that is different sucrose/nitrogen regimes, hormone treatments, pathogen attack, different light regimes and cold and drought stress). Plant MYB genes are involved in many functions including the regulation of secondary metabolism, cellular development and signal transduction.

A number of MYB genes are expressed in response to plant hormones, biotic and abiotic stress. Most of the plant MYB genes with known function are involved in regulating phenylpropanoid metabolism.

A number of MYB genes have been suggested to be involved in the regulation of developmental processes such as shoot morphogenesis (AtMYB13), growth and dorsoventrality of lateral organs (PHANTASTICA) embryogenesis (AtMYBR1 & AtMYBR2) and anther development (AtMYB103 [Li et al., 1999 supra].

Pollen is the haploid male gametophyte in flowering plants and carries the sperm cells required for fertilisation of the ovules. These tiny grains develop within the anther and are released as the anther matures by a process referred to as dehiscence.

Pollen formation requires the expression of temporally and spatially specific genes in the gametophyte and sporophyte. It has been estimated that 20,000 mRNA transcripts are present in the mature pollen of *Tradescantia paludosa* and maize. It is likely that many more transcripts are produced in the early stages of pollen formation, which reflects the complex nature of this process and the need for regulatory genes.

The study of pollen formation over many years has shown significant similarities in a number of plant species. In recent years attention has focussed on *Arabidopsis thaliana*, a model plant for research due to its compact size, short life cycle and small genome which has now been entirely sequenced.

The male haploid phase of development in angiosperms results in the production of pollen, the male gametophyte. Pollen develops within the anther a structure composed of four layers, the epidermis, endothecium, middle layer and tapetum. Within the anther locules, adjacent to the tapetum, lie sporogenous cells from which pollen will develop. The expression of temporally and spatially specific genes in the gametophyte (meiocytes) and sporophyte (tapetum) is required for complete pollen development. Mature pollen grains consist of a vegetative and generative cell (bicellular) or a vegetative cell and two sperm cells (tricellular), surrounded by the intine and exine. A number of common developmental stages have been identified:

Sporogenesis

Sporogenous cells form meiocytes and these undergo two meiotic divisions (meiosis I & II) resulting in a tetrad of haploid microspores surrounded by a β-1,3-glucan (callose) wall. The pollen wall begins to develop as sporopollenin is deposited, forming the exine. Tapetal cells increase in size, numerous ribosomes are present, the endoplasmic reticulum and Golgi proliferate and the number of secretory vesicles increases. As the callose wall degrades, the tapetum reaches its highest secretory phase and the stage of microgametogenesis development ensues.

Microgametogenesis

During this stage the free microspores grow rapidly with further deposition of the exine layer. This coincides with sporopollenin synthesis and secretion by the tapetum. The microspores become vacuolated, at first with many small vacuoles, which later fuse to form a single large vacuole. At this stage exine formation is complete, sporopollenin synthesis has ceased, deposition of the intine begins and internal degradation of the tapetum has commenced.

Microspore Maturation

This stage is characterised by an asymmetric mitotic division (mitosis I) that gives rise to a large vegetative cell and a smaller generative cell. The vegetative cell is involved in further pollen development and later in the formation of the pollen tube. The generative cell will undergo another mitotic division (mitosis II) to produce two sperm cells. The tapetum ruptures releasing cytoplasmic lipid bodies and elaioplasts that associate with the pollen to form a coat. This coat is involved in interactions at the stigmatic surface enabling hydration and successful germination of the pollen grain.

Both *A. thaliana* and *B. napus* belong to the 30% of angiosperms that produce mature pollen in a tricellular state, i.e. the generative cell divides before pollen dehiscence. The generative cell in the 70% of angiosperms producing bicellular pollen undergoes a mitotic division following germination on the stigmatic surface. The cytological processes and time frame of pollen development are relatively consistent within angiosperms despite obvious differences in floral morphology, pollen size and pollen shape that distinguish various genera and families. The conserved nature of pollen development suggests that the processes and genes involved are also likely to be conserved. Examples of conserved pollen-specific genes already exist. The gene P2 in *Oenothera organensis* hybridises to similar transcripts in families representing both monocots and dicots. The pollen specific genes Bcp1 and Bnm1 appear to be conserved within the family Brassicacea.

"Derivatives" of nucleic acid molecules as defined herein encompass those nucleic acid molecules comprising non-naturally occurring nucleotides or those naturally occurring nucleotides that have been modified by chemical or other means.

"Derivatives" of proteins or peptides as defined herein encompass those proteins or peptides comprising non-naturally occurring amino acids or those naturally occurring amino acids that have been modified by chemical or other means.

"Derivatives" as used hereon in relation to nucleic acid molecules, proteins and peptides are also intended to encompass single or multiple nucleotide or amino acid substitutions, deletions and/or additions as well as parts, fragments, portions, homologues and analogues of the nucleic acid molecule or protein or peptide.

Functional derivatives as defined herein encompass nucleic acid molecules, proteins and peptides that are derivatives of the wild type MYB nucleic acid molecules, proteins or peptides but that still retain the wild type function of being expressed in the anther during pollen formation.

Wild type as defined herein refers to the MYB gene, protein or peptide as found in nature.

"Under normal conditions" as used herein is intended to refer to conditions where the inhibiting nucleic acid molecule is not present, i.e. in a plant cell not transformed with the nucleic acid molecule according to the second or third aspects of the invention.

Complementary as used herein in relation to nucleic acid molecule "complementary" to the B. napus nucleic acid sequence or a region thereof, or a functional derivative thereof, is intended to encompass those sequences that are capable of hybridising under high stringency conditions at 42 degrees centigrade to the nucleic acid molecules defined according to the second or third aspects of the invention.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1994) and Sambrook et al., Molecular Cloning, A Laboratory Manual, 2nd Edition (1989) Cold Spring Harbor Laboratory Press, Cold Spring Harbor, N.Y.).

Reference herein to a "region" of the B. napus nucleic acid molecule encompasses a fragment of the B. napus nucleic acid molecule which is expressed in anther tissue during pollen formation and encodes a functional region of an MYB transcription factor.

The invention provides specific nucleic acid molecules BnMYB32, BnMYB103-1 and BnMYB103-2 which encode MYB transcription factors and are expressed in anthers during pollen formation.

The inventors provide evidence herein to show that BnMYB103-1 is expressed during early pollen development.

Experiments performed to ascertain the expression pattern of BnMYB103-1 show that it is expressed most strongly in flower buds 0.5-2.0 mm in length. These bud lengths correlate with specific stages of early pollen development.

BnMYB32 is expressed in developing anthers, its expression commencing in immature anthers and peaking in mature anthers, i.e. from the onset of pollen meiosis to a peak at the conclusion of meiosis. BnMYB32 is also weakly expressed in developing lateral roots and in emerging root tips.

In very young flowers anther primordia are composed of undifferentiated meristematic cells. These cells form a sporogenous cell mass, which will become distinguishable from the tapetum, middle layer, endothecium and epidermis. Archesporial cells align themselves in the anther and divide mitotically giving rise to the tapetum and meiocytes.

0.5 mm Bud Length

At a bud length of 0.5 mm the meiocytes undergo meiosis, an event that occurs synchronously in all locules within the bud. A second mitotic division produces a tetrad of microspores that secrete a β(1,3)-glucan (callose) wall. Mutants in which there is premature dissolution of this wall are usually male sterile, indicating the importance of callose deposition to the production of viable pollen. The tapetal cells undergo mitosis without cytokinesis producing tetraploid binucleate cells.

1.0 mm Bud Length

At 1 mm, meiosis is complete and the new microspores form a tetrad enclosed by a callose wall. The tapetal cells increase in size and volume associated with the proliferation of endoplasmic reticulum and Golgi. Vesicles are present, small vacuoles develop and sporadic lipid bodies are observed. The inner tapetal wall is in contact with the tetrad wall and the tapetum loses its tangential walls.

1.5 mm Bud Length

In 1.5 mm buds a cellulosic primexine develops outside the plasmalemma of young microspores. This provides a matrix for the deposition of sporopollenin, the precursors of which are formed within the microspore cytoplasm and secreted outside the cell between the plasma membrane and callose wall. This process begins the formation of the exine, a structure that gives the mature pollen grain its characteristic sculptured appearance. The callose wall is digested by β(1,3)-glucanase (callase), which is secreted into the locule from the tapetum and releases the microspores. Vacuolation of the microspores is initiated with numerous small vacuoles present. The tapetum secretes fibrillar and small osmiophillic vesicles.

2.0 mm Bud Length

At a bud length of 2 mm the unicellular microspores are characterised by the formation of a single large vacuole in the cytoplasm. Sporopollenin deposition continues until exine formation is complete. The radial cell walls of the tapetum are lost and it has started its final degeneration. Starch granules appear transiently in the tapetal plastids.

2.5 mm Bud Length

In 2.5 mm buds an important asymmetric mitotic division occurs producing bicellular microspores containing a large vegetative cell and a smaller generative cell. The tapetal cells continue to secrete nutrients into the locule but the cellular organelles exhibit characteristics of degradation. Many of the important developmental processes are complete by this stage as evidenced by the fact that meiotically dividing meiocytes can be removed from the anther and will continue development in vitro.

The fact that BnMYB103-1, BnMYB103-2 and BnMYB32 expression is strongest in flower buds 0.5-2.0 mm in length has implications for its role in regulating genes expressed during these early stages of pollen development. Various other anther expressed genes have been identified in A. thaliana and Brassica sp. Function has not yet been assigned to most of these genes and many other genes involved in this process are likely to be identified in the future. However, genes involved in meiotic division, the synthesis of a variety of compounds found in the pollen wall, functions of the tapetum and associated processes are all required during the period in which BnMYB103-1, BnMYB103-2 and BnMYB32 are expressed. The regulated expression of these genes will be necessary and transcriptional regulators such as BnMYB103-1, BnMYB103-2 and BnMYB32 will play an important role.

As well as providing isolated nucleic acid molecules involved in pollen formation in B. napus, the invention also provides othologues in other plant species and encompasses homologues.

A "homologue" is defined as a nucleic acid molecule sharing the same function as another nucleic acid molecule. Homologues are generally determined by sequence similarity as defined by alignment using algorithms such as that in the Advanced BLAST2 service provides by EMBL.

Homologous sequences are generally those with a percentage sequence identity of at least 50% at nucleotide or amino acid level according to BLAST analysis. Similarities of at least 60%, 70%, 80% and 90% that are functionally active are said to be homologous sequences.

"Percent (%) sequence identity" with respect to the nucleic acid sequences identified herein is defined as the percentage of nucleotides in a candidate sequence that are identical with the nucleotides in the specific MYB nucleotide sequence, after aligning the sequences and introducing gaps, if necessary, to achieve the maximum percent sequence identity, and not considering any conservative substitutions as part of the sequence identity.

Alignment for purposes of determining percent nucleotide sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % nucleotide sequence identity values are generated using the WU-BLAST-2 computer program (Altschul et al., *Methods in Enzymology* 266: 460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. For purposes herein, a % nucleotide sequence identity value is determined by dividing (a) the number of matching identical nucleic acid residues between the nucleotide sequence of the MYB gene of interest having a sequence derived from the MYB gene and the comparison nucleotide sequence of interest (i.e., the sequence against which the MYB sequence of interest is being compared which may be a MYB variant) as determined by WU-BLAST-2 by (b) the total number of nucleotides of the MYB gene of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, drop-off for final gapped alignment=25 and scoring matrix=BLOSUM62.

"MYB homologue" or "MYB variant nucleic acid sequence" means a nucleic acid molecule which encodes an active MYB polypeptide as defined below and which has at least about 50% nucleic acid sequence identity with a nucleotide acid sequence encoding a full-length native sequence MYB polypeptide sequence as disclosed herein, or any fragment of a full-length MYB polypeptide sequence as disclosed herein. Ordinarily, a MYB variant polynucleotide will have at least about 50% nucleic acid sequence identity, more preferably at least about 51% nucleic acid sequence identity, more preferably at least about 52% nucleic acid sequence identity, more preferably at least about 53% nucleic acid sequence identity, more preferably at least about 54% nucleic acid sequence identity, more preferably at least about 55% nucleic acid sequence identity, more preferably at least about 56% nucleic acid sequence identity, more preferably at least about 57% nucleic acid sequence identity, more preferably at least about 58% nucleic acid sequence identity, more preferably at least about 59% nucleic acid sequence identity, more preferably at least about 60% nucleic acid sequence identity, more preferably at least about 61% nucleic acid sequence identity, more preferably at least about 62% nucleic acid sequence identity, more preferably at least about 63% nucleic acid sequence identity, more preferably at least about 64% nucleic acid sequence identity, more preferably at least about 65% nucleic acid sequence identity, more preferably at least about 66% nucleic acid sequence identity, more preferably at least about 67% nucleic acid sequence identity, more preferably at least about 68% nucleic acid sequence identity, more preferably at least about 69% nucleic acid sequence identity, more preferably at least about 70% nucleic acid sequence identity, more preferably at least about 71% nucleic acid sequence identity, more preferably at least about 72% nucleic acid sequence identity, more preferably at least about 73% nucleic acid sequence identity, more preferably at least about 74% nucleic acid sequence identity, more preferably at least about 75% nucleic acid sequence identity, more preferably at least about 76% nucleic acid sequence identity, more preferably at least about 77% nucleic acid sequence identity, more preferably at least about 78% nucleic acid sequence identity, more preferably at least about 79% nucleic acid sequence identity, more preferably at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with the nucleic acid sequence encoding a full-length native sequence MYB polypeptide sequence as disclosed herein, or other fragments of a full-length MYB polypeptide sequence as disclosed herein. Variants do not encompass the native nucleotide sequence.

Ordinarily, MYB variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

An "orthologue" may be defined as genes or gene products which are derived from a common ancestor and share a common function. Orthologues are generally homologues.

A study of collinearity between regions of the *A. thaliana* and *B. napus* genomes has shown that genes present as a single copy in *Arabidopsis* are present in between two to eight copies in *B. napus*. Southern blot data reveals four hybridising bands in the *B. napus* genome when probed with AtMYB103. Southern blotting of the *B. oleracea* and *B. rapa* genomes with the same probe shows two hybridising bands in each species. This result is consistent with the AACC genome of *B. napus* and the collinearity data available. It is likely that the four clones obtained in this study represent two genes from each of the parental species that have come together in the *B. napus* genome.

Studies of the *A. thaliana* and *B. napus* genomes provide important insights into the relationship between these species. Genes that are orthologous between these species share an average of 87% DNA sequence identity and extensive conservation of marker order has been found. Work done to date suggests that *Brassica* genomes contain three representations of a basic genome with each representation being extensively collinear with the genome of *A. thaliana*.

A practical example of gene conservation between these species is the senescence specific gene SAG12. This gene which codes for a cysteine protease in *A. thaliana* was used to probe a *B. napus* genomic DNA library and resulted in the isolation of two homologues. These genes show between 83-86% nucleotide sequence identity with SAG12. The similarities in gene structure and expression patterns of these genes indicate they are orthologues.

The ultimate test of functional homology between the two MYB genes would be the rescue of an AtMYB103 mutant by transformation with BnMYB103-1. It is highly likely that AtMYB103 and BnMYB103-1 share a common function in the regulation of early pollen development and as such represent orthologues.

In this context "heterologous" DNA means that the DNA introduced into the cells is a DNA not naturally occurring in the cells in this form. On the one hand, it may be DNA which does naturally not at all occur in these transformed cells or DNA which, even if it does occur in these cells, is integrated at other genetic positions as exogenous DNA and is therefore situated within another genetic environment.

Comparison of the AtMYB103 and BnMYB103-1 sequences show a number of similarities that indicate these two genes are likely to be orthologues. Both genes consist of three exons interrupted by two introns at conserved sites and both have an open reading frame of 960 bp coding for a protein of 320aa. There is 90% identity between the two sequences at the nucleotide level and 93% at the amino acid level. Within the R2R3 repeat region there is 99% identity at the amino acid level. In the first 400 bp of the non-coding region upstream of the ATG start codon there is 74% identity. In *Arabidopsis* it has been shown that this 400 bp promoter region is responsible for the correct spatial and temporal expression of AtMYB103.

Other data support the likelihood that these two genes are orthologues, including promoter gusA experiments where AtMYB103::gusA and BnMYB103-1::gusA constructs transformed into *A. thaliana* both show identical staining patterns. GUS activity is evident in the anthers of flower buds from 0.5-3.0 mm long. Cross sections through stained anthers show that GUS activity is confined to the tapetum and developing microspores. We show herein that antisense and sense BnMYB103-1 constructs under the control of a tapetum-specific promoter (TA39 from tobacco), produce an abnormal pollen phenotype in *A. thaliana*. The abnormalities observed are similar to those seen in *B. napus* plants transformed with the same constructs, indicating that functional homology exists between these two genes.

A search of the literature indicates that this is not an isolated case. Examples exist where antisense and sense technology has been used to down regulate the expression of an endogenous gene in a temporally and spatially specific manner. This has been achieved using an homologous gene from another species under the control of a non-native promoter. The tapetum and microspore expressed *Brassica* gene Bcp1 shows 73% identity to its *Arabidopsis* homologue. A 0.5 kb fragment of the *Brassica* Bcp1 cDNA was used in an antisense construct under the control of a promoter from a pollen-expressed gene of tomato, LAT52. Transformation of this construct into *A. thaliana* was found to inhibit expression of the endogenous gene. The results showed that the *Brassica* Bcp1 antisense cDNA was able to inhibit function of the *Arabidopsis* Bcp1 homologue in haploid microspores, leading to pollen abortion.

During phenylpropanoid biosynthesis the first step is catalysed by phenylalanine ammonia-lyase (PAL), an enzyme active in the tapetum during pollen development. Antisense and sense constructs of PAL cDNA from sweet potato under the control of a tapetum-specific promoter from rice, Osg6B, have been transformed into tobacco. Analysis of anthers from transgenic plants showed a reduction in PAL activity, which was accompanied by a partial male sterility phenotype. Another example involves the use of a genomic DNA fragment for the alternative oxidase gene from *A. thaliana*. Expression of this gene has been demonstrated in the tapetum and pollen during anther development. An antisense construct of this fragment under the control of the tapetum-specific rice promoter Osg6B was transformed into tobacco. Expression of the alternative oxidase gene in transgenic plants was much lower than in wild type and resulted in partial male sterility.

The ultimate test of functional homology between the two MYB genes would be the rescue of an AtMYB103 mutant by transformation with BnMYB103-1. It is highly likely that AtMYB103 and BnMYB103-1 share a common function in the regulation of early pollen development and as such represent orthologues.

The Advanced BLAST2 and Orthologue Search Service at EMBL was used to find sequences likely to represent orthologues of BnMYB103-1. Using the BnMYB103-1 amino acid sequence as the query sequence the highest score of 1449 $3.6e^{-148}$ was obtained for AtMYB103. The other genes shown in this analysis are all recognised MYB genes or described as MYB-like, putative MYBs or putative transcription factors. Further analysis with this service produced a species tree (FIG. 8) using the NCBI database and a gene tree (FIG. 9) based on the neighbour-joining tree computed By CLUSTALW. The species tree is a phylogenetic tree representing evolutionary relationships between the species under consideration. Genes from several species were represented in this analysis and most grouped along family lines, *Lycopersicon esculentum* and *Petunia hybrida* from the Solanaceae, *Arabidopsis thaliana* and *Brassica napus* from the Brassicaceae and *Oryza sativa, Zea mays*, and *Hordeum vulgare* from the Poaceae. However, the grouping of *Antirrhinum majus, Gossypium hirsutum* and *Pimpinella brachycarpa* does not reflect a familial relationship. Unsurprisingly, the moss *Physcomitrella patens* does not group with any of these flowering plants. The sorting of genes according to this taxonomic tree groups BnMYB103-1 with thirty-one *A. thaliana* sequences. Fifteen of these genes are MYBs, including AtMYB103, the others are described as MYB-related or transcription factor-like proteins.

The inventors have isolated orthologues of the *B. napus* MYB genes from an *A. thaliana* cDNA library and these genes have been characterised:

AtMYB32 This gene is expressed in developing anthers from the onset of pollen meiosis and expression reaches its peak at the conclusion of meiosis. AtMYB32 is also expressed in developing lateral roots and in emerging root tips. Antisense and cosuppression AtMYB32 transgenic plants exhibit an abnormal pollen phenotype.

AtMYB103 Expression studies using a promoter::GUS construct suggest this gene is specifically expressed in developing flowers at a stage where the pollen mother cells separate and undergo meiosis to form a tetrad of microspores. GUS activity is highest during the tetrad stage and was expressed in the tapetum and middle layer of the anther and in microspores. The GUS activity results have been confirmed with in situ hybridisation experiments [Li et al., 1999 supra].

As AtMYB32 and AtMYB103-1 are expressed at the time of important processes in the anther and pollen indicates that these genes are likely to be involved in regulating other genes required for pollen development.

Thus, the isolation of the BNMYB32 and the BnMYB103-1 and BnMYB103-2 genes and their homologues and orthologues of the present invention provides a strategy for pollen-control. The gene BnMYB103-1 is exclusively active in developing anthers, whereas the gene BnMYB32 is active during lateral root initiation, as well as being expressed (turned on) in a number of tissues of the developing anther, including the tapetum (a tissue providing nutrients for pollen development as well as pollen-wall components and enzymes for microspore release from the enclosing callose wall) and the microspores themselves. Expression of the BnMYB103-1 and BnMYB103-2 genes and the BnMYB32 gene occurs only during the early stages of pollen development, the genes subsequently becoming "silent".

Although the precise functions of the genes are not known, they code for proteins that belong to a family of proteins (MYB-like) that bind to specific DNA sequences. Such MYB-like proteins regulate the activity of other genes. Two MYB-like proteins in maize, for example, control anthocyanin synthesis. The inventors' results indicate that the MYB103 gene(s) and the MYB32 gene regulate genes important in pollen development.

Experiments in which antisense MYB103 gene(s) and MYB32 gene constructs were placed under control of the Cauliflower Mosaic Virus 35S promoter and introduced into *A. thaliana* plants, resulted in plants with defective pollen.

The inventors have found that their MYB-like genes, express in the anther during pollen development are conserved between species. Consequently, the antisense approach using the *A. thaliana* or *B. napus* genes can be expected to function in crops both closely related and distinct (e.g. wheat).

Moreover, the introduced (sense or antisense) MYB103 gene(s) and MYB32 gene can be genetically engineered so that the genes are expressed at high levels in anthers and the expression can be induced by simple chemical treatment of plants.

Thus, sense or anti-sense constructs of the specified gene(s) of the invention can be utilized to put the invention into practice by being integrated into the genome of a number of relevant transformable plant species (e.g. canola, tomato, grain legumes, cereals) with anthers and pollen developed therefrom.

The inventors propose that the MYB-like genes of the present invention may be used in conjunction with other genes that are involved in male-specific development, such as those encoding putative transcription factors NOZZLE, MS1 and MYC class transcription factor (see for example Sorensen, A-M et al., The Plant Journal (2003) 33, 413-423). The use of such genes is likely to improve the percentage efficiency of the induction of male sterility.

"Antisense nucleic acid molecules" as described herein defines sequences that are complementary to the nucleic acid molecules of the first aspect of the invention or part thereof. Such antisense nucleic acid molecules, may bind to the endogenous gene and block prevent expression of the functional gene in a plant cell. Antisense techniques generally use short 10 to 20 oligonucleotide fragments which hybridise to essential parts of the gene thereby blocking its expression. Such essential regions of the gene may include regions within the 5' regulatory region such as enhancer and promoter regions and may also include the transcription start site.

By "promoter" is meant a minimal sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

A promoter may be constitutive but most preferably is inducible. The construct may contain one or more promoters.

Plasmids, phage and vectors are all terms to describe carriers for introducing nucleic acid into cells. There are a number of methods available for introducing foreign nucleic acid molecules into plant cells and it is not intended that the invention is restricted to any one of these carriers. The most generally used transformation methods include particle bombardment, polyethylene-mediated transformation and microinjection. The particular method chosen to obtain transformed plants containing nuclear genomes with the inserted nucleic acid will depend on the plant species.

In practice, any nucleic acid used to transform plant cells will most likely be in the form of a nucleic acid construct.

In practice, a construct used to transfect the plant nucleus will generally additionally comprise various control elements. Such control elements may include promoters and optionally a ribosome binding site (RBS), positioned at an appropriate distance upstream of a translation initiation codon to ensure efficient translation initiation.

Constructs envisaged according to the present invention include those constructs comprising an anther specific promoter and at least one gene coding for an MYB transcription factor, which gene is expressed in the anther during pollen formation.

A person skilled in the art will be readily able to determine suitable constructs. For example we provide a construct comprising an AtMYB103 gene under the control of the TA39 promoter, the AtMYB103 gene being provided in either the sense or antisense direction, i.e. 5' to 3' or 3' to 5'. We also provide a construct comprising the BnMYB103-1 and BnMYB103-2 genes lined together, and an AtMYB-32 gene, each gene in either the sense or antisense direction and all genes all under the control of an anther specific promoter.

Preferably most or all of the constituents of the construct are operably linked.

Due to the homology between the genes in different species the inventors propose that MYB genes from one species may be used in constructs used to transform other species and that species specific genes be used in constructs with orthologues from other species, for use in transforming any plant species.

For example a construct comprising BnMYB103-1 and BnMYB103-2 genes may also include an AtMYB32 gene and be used to transform Brassica species under the control of an anther specific promoter such as TA39 from tobacco.

A preferred construct further comprises GVG, a chimeric transcription factor which binds to and activates the 6UAS promoter in the presence of dexamethasone (see Aoyama, T. and Chua, N. H., The Plant Journal (1997) 11(3), 605-612). The construct may also comprise a selectable marker, for example HPT, encoding hygromycine phosphotransferase, to allow for selection of transgenic plants comprising the construct.

A further preferred construct further comprises a NOZZLE, MS1 or MYC gene, or other nucleic acid encoding proteins involved in male-specific development (see for example Sorensen, A-M, et al., supra).

The construct may incorporate into the plant nuclear genome through recombination events.

An anther specific promoter defines any promoter which targets the construct to the anther in preference to other positions.

A number of regulatory sequences from the promoter region of anther or pollen-specific genes have been identified using promoter deletion analysis. Minimal promoter regions required for tissue-specific gene expression have been described (Twell et al., (1991) Genes & Development 5: 496-507). The chiA promoter from petunia contains the CCACAAAAA motif (van Tunen et al., (1990) Plant Cell 2: 393-401) while the Bp19 gene from Canola contains the motif TGACG that is also present in the nos and 35S promoters (Albani et al., (1991) Plant Molecular Biology 16: 501-513. The A9 gene from Arabidopsis contains a TATATATA motif in the promoter region thought to direct tapetum-specific expression (Paul et al., (1992) Plant Molecular Biology 19: 611-622). The 52/56 box TGTGGTTATATA and the 56/59 box TGAAATTGTGA are conserved sequence motifs in the tomato LAT genes (Eyal et al., (1995) Plant Cell 7: 373-384). The pollen-specific α-tubulin gene from Arabidopsis also contains sequences similar to the 56/59 box (Carpenter et al., (1992) Plant Cell 4: 557-571). The AAATGA sequence directs pollen specificity in alfalfa promoters (Wu et al., (1998) Sexual Plant Reproduction 11: 181-182). Sequence similarities among tissue specific promoters are restricted to short sequence motifs. Promoters may share a similar sequence but are also influenced by upstream regulatory elements that influence expression levels (Twell et al., 1991 supra).

The tobacco TA39 promoter regulates tissue-specific gene expression in the anther tissue (Goldberg et al., (1993) Plant Cell 5: 1217-1229. This promoter is expressed in the microspheres, connective tissue and most highly in the tapetum during early pollen development. The TA39 promoter is widely used in gene constructs to control the expression of transgenes directed to the tapetum tissue in the anther and is a preferred promoter used in the constructs of the present invention. Another preferred anther specific promoter is the AT anther specific promoter described in our co-pending application entitled "Promoter and Uses Thereof".

The anther specific promoter is preferably a constitutive but tissue specific promoter.

The construct may further comprise means for controlling when the gene is expressed. Such means include the use of an inducible promoter so that expression of the construct may be achieved at a desired time point. Aoyama, T. and Chua, N. H. The Plant Journal (1997) 11(3), 605-612 describe a chemical induction system for transcription in plants. This system utilises a chimeric transcription factor, GVG, consisting of the DNA-binding domain or the yeast transcriptional factor GAL4, the transactivating domain of the herpes viral protein VP16 and the receptor domain of the rat glucocorticoid receptor (GR). The promoter is induced in response to dexamethsone (DEX), a strong synthetic glucocorticoid. Once activated by dexamethasone, GVG can induce the transcription from the chimeric promoter by about 100 fold.

This system, and other inducible promoter systems, may be used in the constructs of the present invention.

Another means for controlling the time of gene expression involves the use of a dominant repressor system. The construct may contain, optionally in combination with an inducible promoter, a repressor/restorer system (as described below) to allow control of expression of the genes in the construct.

The present invention provides transformed cells comprising a nucleic acid molecule or fragment thereof according to a first aspect of the invention or a construct according to the second aspect of the invention. By means of methods known to the skilled person the transgenic plant cells can be regenerated to whole plants. Thus, the plants obtained by regenerating the transgenic plant cells of the invention are also the subject-matter of the present invention. A further subject-matter of the invention are plants which contain the above-described transgenic plant cells. The transgenic plants may in principle be plants of any desired species as previously defined.

The invention also relates to propagation material of the plants of the invention, e.g. fruits, seeds, tubers, root-stocks, seedlings, cuttings etc.

The plants cells may be transformed with a first construct comprising one or more MYB genes and then be subsequently transformed with a further construct comprising one or more same or other MYB genes or fragments thereof or another gene involved in male-specific development, it is not necessary that all the genes to be introduced on the cell be provided on the same construct. In other words, rather than transforming the genome with a single construct comprising at least two MYB genes and optionally another gene, the genes may be introduced on separate carriers.

When two nucleic acid sequences are used they are preferably introduced together by co-transformation.

The invention in a fourth aspect provides method for controlling pollen development in a plant by introducing into the plant means of inhibiting the expression of the endogenous MYB gene expressed in the anther during pollen development.

Based on the nucleic acid sequences provides persons skilled in the art would be able to design suitable means to substantially block expression of the endogenous MYB gene.

An "endogenous gene" is a gene that is naturally present in a cell. The endogenous MYB gene as used herein describes the MYB gene that would be naturally expressed in a plant cell under normal conditions.

The production of plant cells which lack the expression of one or more endogenous MYB genes may for example be achieved by the expression of a corresponding antisense-RNA, of a sense-RNA for achieving a co-suppression effect or the expression of a correspondingly constructed ribozyme, which specifically cleaves transcripts encoding one of the proteins of the invention, using the nucleic acid molecules of the invention or the AtMYB103 gene.

In order to block expression of endogenous gene(s) according to the first aspect of the invention, antisense-RNA is preferably expressed in plant cells and the technique known as RNA interference (RNAi) is used. (Waterhouse et al., (1998) Proc. Natl. Acad. Sci. USA 95, 13959-13964).

In brief canola plants expressing the sense sequence of BnMYB103-1 are crossed with plants expressing the same BnMYB103-1 sequence in antisense orientation. F1 plants exhibited pollen abnormality and some male sterility. The F1 phenotypes were more severe than either parent. It is likely that the sense and antisense transcripts of the BnMYB103-1 transgenes formed double-stranded RNA molecules leading to the degradation of endogenous BnMYB103-1 transcript. The RNAi system using double stranded RNAs to block gene expression is widely used.

In order to express an antisense-RNA, on the one hand DNA molecules can be used which comprise the MYB gene(s) complete sequence, including possibly existing flanking sequences as well as DNA molecules, which only comprise parts of the coding region. These parts have to be long enough in order to prompt an antisense-effect within the cells. Basically, sequences with a minimum length of 15 bp, preferably with a length of 100-500 bp and for an efficient antisense-inhibition, in particular sequences with a length of more than 500 bp may be used. Generally DNA-molecules are used which are shorter than 5000 bp, preferably sequences with a length of less than 2500 bp.

Use may also be made of nucleic acid sequences which are highly homologous, but not completely identical to the sequences of the nucleic acid molecules of the invention. The minimal homology should be more than about 65%. Preferably, use should be made of sequences with homologies between 95 and 100%.

In an embodiment the cells of the invention differ from naturally occurring cells in that they contain a heterologous recombinant DNA molecule encoding an antisense RNA, a ribozyme or a cosuppression RNA. Due to the expression of this heterologous recombinant DNA molecule the expression of the MYB gene(s) is prevented, resulting in lack of production of the MYB transcription factors in the anther. As the MYB genes are implicated in the formation and production of pollen, preventing expression of the MYB nucleic acid molecules according to the present invention provides transgenic plants which do not produce pollen.

Sense oligonucleotides may also be used instead or together with antisense oligonucleotides.

Preferably the method comprises the use of a system that controls the expression of the MYB gene(s) and allows expression of the gene(s), and hence the production of pollen, to be turned on and off as desired.

In one embodiment the system is an inducible system. The inducible system may involve induction of the GVG promoter in a transgenic plant with dexamethasone or some other inducible systems may be used. It is preferred that the system be inducible so that production of male sterile plants may be reversible. The method of choice would involve the use of a cheap, non-toxic inducer molecule that can be sprayed on plants to activate antisense gene(s) and block pollen development. It is preferred that in the absence of inducer, the transgenic plants will produce normal pollen.

Another system for controlling expression of a gene of interest, which may be used in the present invention but may also find utility outside the constraints of the present invention, is a repressor/restorer system. In this system the functioning of an essential gene is repressed using a transcription repressor.

Transcription repressors use various repressive motifs to block the transcription of their target genes. One repressor motif suitable for use in plants has the amino acid sequence LDLDLELRLGFA (SEQ ID NO: 27) (Hiratsu, K. et al., (2003) supra. Another suitable repressor for use in plants has the amino acid sequence LDLNLELRISPP (SEQ ID NO: 28)(Jin, H. et al., (2000) EMBO J 15, 6150). These motifs are designated EAR (ERF-associated amphiphilic repression). It would appear that the amino acid sequence LXLXLX (SEQ ID NO. 29) is essential to the repression function of the EAR motif AtMYB103 was chosen to test the inducible repressor system in plants. This gene was a suitable candidate as it is strongly expressed in Arabidopsis and encodes a transcription factor, an essential factor in the development of viable pollen. In the system it was proposed that functioning of the AtMYB103 gene could be repressed using a repressor motif, but turned back on (restored) by crossing.

The two peptide sequences exhibit nine identical or homologous residues. The repressive motif (LDLDLELR-LGFA) (SEQ ID NO: 27) from Arabidopsis was fused to four different transcription factors with resultant loss-of-function phenotypes demonstrating that the motif converts transcription factors into strong dominant repressors. Inspection of AtMYB7 (Li, S.F., Parish, R.W. (1995) Plant J. 8, 963) and AtMYB32 C-terminal sequences identified the repressive sequence LDLNLELRISPP (SEQ ID NO: 28).

The strategy is to test the repressor/restorer system proposed by studying if you could convert AtMYB103 into a strong repressor using the motif of twelve amino acids to obtain male sterility. The heterozygous male sterile inbred A containing the chimeric AtMYB103 repressor (AtMYB103Rep) is crossed with inbred B containing a "restorer" to produce male fertile F1 hybrid seeds. The "restorer" will be AtMYB103 gene under the control of the strong anther-specific At39 promoter or multiple copy of the AtMYB103 promoter or their equivalents. Higher levels of the AtMYB103 protein (activator) in the hybrid plants will alleviate the repression by AtMYB103Rep protein leading to viable pollen production and seed setting.

The repressor/restorer system produces 50% male fertile inbred A seedlings. A selectable marker linked to the repressor will provide a selection to cull the male fertile inbred A seedlings before crossing with inbred B. Alternatively, a simple chemical which can overcome the repression by the AtMYB103Rep may be used to induce seed setting of the male sterile plants to obtain the homozygous inbred A seed. The homozygous and male sterile inbred A plants will then be crossed with inbred B plants to obtain F1 hybrid seed.

The repressor/restorer reversible male sterility system is being successfully tested in *Arabidopsis* and is suitable for hybrid seed production in any crop plants including canola and wheat. The repressor/restorer system is the preferred system for use controlling gene expression in the method of the first aspect of the invention because it potentially avoids the need to spray crops to achieve control of expression.

By disrupting pollen formation according to the first aspect of the invention there is provided a method for providing male sterile plants, that is transgenic plants which do not produce pollen. The ability to bring about male sterility by the directed expression of genes able to inhibit pollen development or the expression of antisense and co-suppression constructs designed to inhibit genes required for pollen formation in a controlled manner is particularly important.

To allow male sterility to be achieved it is important that pollen formation is completely disrupted rather than being merely produced. Blocking one or more of the MYB nucleic acid sequences according to the present invention may provide complete disruption of pollen formation and hence produces 100% male sterile plants. The percentage efficiency of blocking may be improved if, in addition to MYB32 and MYB103, other genes involved in male-specific development are also blocked.

With regard to the specific embodiments of the present invention, in *Brassica napus* blocking expression of the BnMYB103-1 gene alone does not give 100% male sterile plants. It is also necessary to block BnMYB32 and probably also BnMYB103-2. It may also be necessary to block MYC and/or other genes involved in male-specific development (see Sorensen, A-M, et al., supra).

In *Arabidopsis* blocking expression of AtMYB32 and AtMYB103 gives 100% male sterile plants.

In *Arabidopsis* an AtMYB103 insertional mutant is provided which exhibits complete male sterility with early tapetum degradation and collapsed pollen. Loss-of-function mutant plants were also obtained using an AtMYB103/EAR chimeric repressor. The plants are male sterile and the effects on tapetum and pollen development are similar to those observed in the insertional mutant. The chimeric repressor and restorer constitute a reversible male sterility system which can be adapted for hybrid seed production. This is the first reversible male sterility system targeting a transcription factor essential to pollen development.

It is proposed that because of the extensive homology of the MYB genes of the present invention between species that the sequence used to block expression of an MYB gene in one species could be derived from an MYB gene from anther species. For example a construct comprising the BnMYB103-1 and BnMYB103-2 genes and the AtMYB32 gene was shown to produce male sterile plants in *B. napus*. It is proposed that the *Brassica* and *Arabidopsis* MYB genes according to the present invention could be used to produce male sterility in other plant species, including wheat, barley etc.

Although such methods may have utility it is especially preferred that the MYB genes used are species specific, particularly to appease any problems perceived in relation to genetically modified organisms.

For the purposes of this specification it will be clearly understood that the word "comprising" means "including but not limited to", and that the word "comprises" has a corresponding meaning.

It will be clearly understood that, although a number of prior art publications are referred to herein, this reference does not constitute an admission that any of these documents forms part of the common general knowledge in the art, in Australia or in any other country.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Embodiments of the present invention will now be described in the following non-limited examples.

EXAMPLES

Example 1

Genes from *Arabidopsis* Expressed in the Anther During Pollen Development a) AtMYB32
Isolation of Genomic Clone
An *Arabidopsis thaliana* (Landsberg erecta) genomic library in the vector EMBL3 was screened with a 38-mer oligonucleotide directed against the conserved region of the third repeat of the mammalian MYB DNA-binding domain.

Screening procedures were carried out according to Ausubel et al. supra. Hybridisation was performed at 40° C. with the $^{32}$P-labelled 38-mer probe 38mer probe: CCTG-GTCGTACTGA(C/T)AA(C/T)GA(A/G)ATTAA(A/G)AA (C/T)TA(C/T)TGGAA (SEQ ID NO. 31), followed by washes of 6×SSC at 50° C. Positive clones were isolated and subjected to Southern analysis by digesting with restriction enzymes BamHI, EcoRI or Sa/I and probing with the $^{32}$P-labelled 38-mer. A 3.5 kb EcoRI-BamHI fragment and a 5.0 kb BamHI-Sa/I fragment were isolated and cloned into the vector pTZ18U (Bio-Rad). These clones were further subcloned and sequenced.

Plant Transformation

The following procedures were principally performed as outlined by Ausubel et al. supra unless otherwise specified. A Bbsl restriction fragment of approximately 1000 bp from the 3.5 kb EcoRI-BamHI clone comprising the 5' promoter region of AtMYB32 was blunt ended with T4 DNA Polymerase (Promega) and cloned into the Smal site of pBluescript (Strategene). The 1000 bp 5' promoter fragment in pBluescript was excised with BamHI and EcoRV and cloned into the BamHI and Smal sites of pBI101.3 (Clontech). This construct was transformed into *Agrobacterium tumefaciens* strain AGL1 using the method outlined by Ditta et al., (1980) PNAS 77: 7347-7351. *Agrobacterium* harbouring the construct were used to transform *Arabidopsis* root explants using the methods described by Valvekens et al., (1988) PNAS 85: 5536-5540. Transformed cells were selected on a shoot inducing media containing kanamycin (Sigma) 100 µg/ml, and subsequently transferred to a growth medium containing kanamycin at 50 µg/ml.

Growth of Plants

Transgenic seeds were sown onto plates containing germination media and grown under constant illumination at 22° C. for approximately four weeks. Plants were then transferred to hydroponic pots and grown in a nutrient solution under the above conditions. After approximately two weeks, auxin (2,4-Dichlorophenoxy-acetic acid) was added to the pots to a concentration of 25 µM. Plants were harvested and screened for GUS activity as outlined below.

Polymerase Chain Reaction (PCR)

The PCR was carried out according to Klimyuk et al., (1993) Plant J. 3: 493-494, in which whole plant tissue was subjected to an alkali treatment and used directly in the PCR. A primer pair was generated against regions outside the multi-cloning site of pBl101 (Clontech). Primers used were 5'TGTGGAATTGTGAGCGGATA (SEQ ID NO. 32) (725-744 of pBl101) and 5'ATTCCACAGTTTTCGCGATC (SEQ ID NO. 33) (929-910 of pBl101). Cycling conditions were 94° C. for 30 sec; 58° C. for 20 sec; 72° C. for 1 min; 36 cycles, followed by a 10 min extension at 72° C. PCR products were visualised on a 2.5% agarose gel.

GUS Assays and Histochemistry

Tissues from transformed plants were assayed for GUS activity by incubating overnight at 37° C. in a 0.5 mg/ml X-gluc (5-bromo-4-chloro-3-indoyl-β-D-glucuronide cyclohexylammonium salt) substrate solution. Histochemical analysis was carried out according to Caissard et al., (1992) Protoplasma 170: 68-76 with samples embedded in LR White resin (London Resin Company). Sections of 10 µm were stained with 1% Saffranin O and GUS activity observed under a light microscope.

Results
AtMYB32 clones were isolated and subjected to Southern analysis. Sequencing indicated that an *Arabidopsis* myb-like gene had been isolated and this was designated AtMYB32 (FIG. 4). The genomic organisation and amino acid sequence of AtMYB32 were determined through sequence comparison with previously reported plant myb-like genes. The AtMYB32 gene possesses one intron which occurs in the $R_3$ repeat of the DNA-binding domain. The putative AtMYB32 protein product is comprised of 274 residues with an estimated molecular weight of 31.5 kDa. The N-terminal domain is comprised of the two MYB repeats, ($R_2$ and $R_3$) and displays high sequence similarity to previously reported plant MYB-related proteins.

An *Arabidopsis thaliana* genomic library was screened with a degenerate 38-mer probe 38mer probe: CCTGGTCG-TACTGA(C/T)AA(C/T)GA(A/G)ATTAA(A/G)AA(C/T)TA(C/T)TGGAA (SEQ ID NO. 34), directed against a conserved region Three highly conserved tryptophan residues separated by 18-19 amino acids in each of the three c-MYB repeats constitute a hydrophobic core around which three α-helical bundles are positioned in each repeat.

Three tryptophan are residues present in the $R_2$ and two in the $R_3$ repeat of AtMYB32. As has been found in many plant MYB-related proteins, the first tryptophan in $R_3$ is substituted by phenylalanine. The binding capacity of c-MYB is not impaired when this tryptophan is exchanged for an aromatic/ hydrophobic residue. The carboxyl region of AtMYB32 shows little similarity with other MYB-like proteins except for the sequences GIDPATH, CLDLNLELRISPP and GLNNTRVLDFSTLEMK. A serine-rich region (10 of 14 amino acids are serine) occurs within the carboxyl terminus.

Expression of the AtMYB32 Promoter-Gus Construct

To elucidate the expression pattern of AtMYB32, the 5' promoter region was fused to the GUS reporter gene and used to transform *Arabidopsis* root explants. Fourteen transformant lines were obtained. To confirm the integrity of the constructs in the transgenic plants, PCR was carried out on plant tissue using primers directed against regions outside the cloning site of the binary vector pBl101 (data not shown). GUS activity was initially identified in the anthers during early stages of floral development. Initial GUS expression coincided with stage 9 of *Arabidopsis* floral development, while maximal GUS levels were observed at floral stage 10. Hence, initial GUS activity coincided with the onset of pollen mother cell meiosis and peaked at the conclusion of the meiotic stage when the microspores were present as tetrads. GUS activity subsequently declined during later stages. This developmental sequence takes approximately 72 hours (based on the estimates of floral development outlined in Bowman J (ed) *Arabidopsis* an atlas of morphology and development. Springer-Verlag NY (1994)).

GUS activity was also observed in emerging lateral roots. GUS activity was associated with the primordia involved in the initiation of lateral roots. As the roots extended, some activity remained in this region and also occurred in the root tip. This is probably because some cells expressing GUS in the primordia are destined to form the tip of the emerging root. Subsequently, GUS activity disappeared. Exogenously applied auxin promotes the formation of lateral roots and recent genetic evidence supports such a role for auxin in vivo. Transgenic lines were grown in hydroponic solution and treated with auxin. After treatment times of between 36 and 48 hours, a substantial increase in GUS activity was observed throughout the roots, reflecting both the hormone stimulation of lateral root initiation and new staining within the roots (e.g.

primary root apices, vascular tissue). No stimulation of GUS activity was detected in the anthers of auxin-treated plants (data not shown).

The levels of AtMYB32 expression in both developing anthers and lateral roots appear to be relatively low. Incubation periods of 16-18 hours in X-gluc were needed to obtain adequate staining. However, an 8-10 hour incubation was sufficient to detect activity in auxin-treated roots. Untransformed plants or control transgenic plants transformed with a promoterless GUS construct did not stain (results not shown).

Clearly, the presence of AtMYB32 in such divergent tissues as pollen and emerging roots, need not imply that it regulates identical genes in those tissues. Tissue specific MYB partners may be required to form functional transcriptional activators or repressors.

b) AtMYB103

AtMYB103 was isolated from a genomic library of *Arabidopsis* as described in Li et al., supra which is incorporated herein in its entirety by reference. The nucleotide sequence of AtMYB103 has been deposited in GenBank under accession number AF048839. The gene was shown to be expressed during the early stages of anther development and it was proposed, amongst other things, that the gene may regulate pollen development.

Example 2

Genes from *Brassica* Expressed in the Anther During Pollen Development

Materials and methods carried out in relation to *Brassica napus* are essentially the same as those carried out for *Arabidopsis thaliana* as described in detail above.

a) BnMYB32

Total RNA from young canola flower buds was subjected to RT-PCR amplification using nested primers, Primer sequences: ATGGGAAGGTCTCCTTGCTGTG (SEQ ID NO. 35), TCATTTCATTTCCAAAGTGCTA (SEQ ID NO. 36), designed using the nucleotide sequence of AtMYB32 and a fragment was sequenced. The protein sequence, shown in FIG. 1, codes for a peptide with 80% sequence identity with AtMYB32 (97% identity in the MYB domain) and is designated BnMYB32.

The expression pattern of BnMYB32 in canola was determined using Northern blot hybridisation as described in relation to AtMYB32, and was found to be similar to that of AtMYB32 in *Arabidopsis*. Poly A RNA samples were extracted from canola shoots, roots flower buds and anthers of various developmental stages. A 420 bp BnMYB32 fragment coding for the C-terminal was used as a probe in the Northern blot. The BnMYB32 expressed weakly in roots and young shoots. Its expression commenced in immature anthers and peaks in mature anthers. The nucleotide sequence of BnMYB32 is provided in FIG. 1.

Another clone identified encodes a protein identical to BnMYB32 but with the deletion of the R2 repeat in the MYB domain. The inventors propose that BnMYB32-R3 may be derived from BnMYB32 via alternative splicing of the BnMYB32 mRNA.

BnMYB32R3 Peptide Sequence:

(SEQ ID NO. 37)
MGRSPCCEKDHTNKGAWTKEEDDLIIKLHSLLGNKWSLIATRLPGRTDNEIKNYWNTHVKRKLLRGG

IDPTTHRPINEAKAPRDSSETRETEDSLVKFLSFSRQLEKKESFGEERNDQKGLICKKERVEYSIVE

EKCLDLNLELRISPPWQDQQHHDETKLWFGKEKYMCTACRFGLGNGKKCSCDNVKCQVEYSSSSSSH

SSSDISSSVIGYDFLG

BnMYB32R3 Nucleotide Sequence:

(SEQ ID NO. 38)
TGATAAGCTTATGGGAAGGTCTCCTTGCTGTGAGAAGGACCACACGAACAAAGGAGCTTGGACTAAA

GAAGAAGACGATCTCATCATCAAACTCCATAGCCTCCTTGGAAACAAATGGTCTCTTATCGCGACGA

GATTACCGGGGAGAACAGATAACGAGATCAAGAACTACTGGAATACACACGTAAAGAGGAAGCTTTT

GAGAGGAGGGATTGATCCCACGACTCATCGGCCGATCAACGAAGCCAAAGCTCCTCGTGATTCGTCT

GAGACTAGAGAGACAGAGGACTCGCTTGTGAAGTTTCTATCTTTCAGTCGTCAACTGGAGAAAAAGG

AAAGTTTTGGGGAAGAGAGAAATGATCAGAAAGGACTGATTTGCAAAAAAGAGAGAGTTGAGTATTC

GATTGTTGAAGAAAAGTGCTTAGATTTGAATCTTGAGCTTAGAATCAGCCCGCCATGGCAAGACCAA

CAGCACCATGATGAGACCAAACTTTGGTTTGGGAAAGAGAAGTACATGTGCACTGCATGCCGTTTTG

GGTTGGGAAACGGCAAGAAGTGTAGCTGCGATAATGTTAAATGTCAAGTCGAGTACAGTAGTAGCAG

CAGCAGCCATTCTTCAAGCGATATTAGTAGTAGCGTTATTGGTTATGACTTCTTGGGTA b) BnMYB103-1

Wild type *Arabidopsis thaliana* (Landsberg Erecta ecotype), *Agrobacterium tumefaciens* (AGLI strain) and the plasmid pRK2013 were supplied by Dr. David Smyth (Department of Genetics and Developmental Biology, Monash University, Melbourne, Australia).

Plasmids pGEM®-3Zf (+) cloning and transcription vector.
pBluescript®II SK (amp$^r$) phagemid vector.
pBI101.2 (kan$^r$) plasmid containing a promoter-less GUS cassette in the binary vector pBIN19, used for plant transformation. [Jefferson, 1987 EMBO J. 6: 3901-3907].
pRK2013 (kan$^r$) a helper plasmid for mobilisation of non-self-transmissible plasmids [[Ditta, 1980 supra].

Bacterial Strains

*E. coli* strain DH5α (F$^-$, end A1, hsd R17 [r$_k^-$, m$_k^-$]. supE44, thi –1, λ$^-$, recA1, gyrA96, relA1, Δ [lac/ZYA-argF] U169 deoR, [φ80d lac ZΔM15]).

*E. coli* strain MV1190 (Δ[lac-proAB], thi, supE, Δ[srt-recA] 306::Tn10 [tet$^R$] [F$^-$: tra D36, proAB$^q$, lacI$^q$ lacZΔM15]).

*Agrobacterium tumefaciens* strain AGLI (AGLO recA::bla pTiBo542ΔT Mop$^+$Cb$^R$) [Lazo, 1991 Biotechnology 9: 963-967].

*Arabidopsis Thaliana* Line

Landsberg erecta ecotype (isolated Landsberg, Germany) containing a homozygous recessive mutation, erecta, which confers a more compact phenotype.

Oligonucleotides

```
Universal primer -
5' GTAAAACGACGGCCAGT 3'     (SEQ ID NO. 39)
```

17mer used for sequencing in pGEM and pBluescript vectors.

```
Reverse primer -
5' AACAGCTATGACCATG 3'      (SEQ ID NO. 40)
```

17mer used for sequencing in pGEM and pBluescript vectors.

```
pBI101 forward primer -
5' TGTGGAATTGTGAGCGGATA 3'  (SEQ ID NO. 41)
```

20mer used for sequencing and amplification.

```
pBI101 reverse primer -
5' ATTCCACAGTTTTCGCGATC 3'  (SEQ ID NO. 42)
```

20mer 80 base pairs 3' to the multicloning site, used for sequencing and amplification.

```
A5962H02 -
5' GAAAGAAGAAATGGGTCGGA 3'  (SEQ ID NO. 43)
```

20mer situated at the 5' end of AtMYB103 including the ATG start

```
A6004A01 -
5' CAACCACTTCTCCCTTCAGC 3'  (SEQ ID NO. 44)
```

20mer situated 150 bp upstream of the AtMYB103 TGA stop codon.

```
A5956A10 -                  (SEQ ID NO. 45)
5' GGGGGGGTCGACATGGGTCGGATTCCATGTTG 3'
```

32mer beginning at the ATG start codon of AtMYB103, including a Sal I restriction site.

A2485F04 -
(SEQ ID NO. 46)
5' GGGGAAGCTTTCCTCCTCCTCGTGCGCGGT 3'

30mer situated 180 bp upstream of the AtMYB103 TGA stop codon.

Z1346E10 -
5' TAAAAATCAAACCATATGAT 3' (SEQ ID NO. 47)

20mer situated at 3' end of AtMYB103 including the TGA stop codon.

(SEQ ID NO. 48)
SRK1 -    5' TTAAAGAGAGACGATCGAGAG 3'

21mer situated 20 bp upstream of the BnMYB103-1 ATG start codon.

SRK2 - 5' CTATTTGGCGTCCTGGACCT 3' (SEQ ID NO. 49)

20mer situated 176 bp downstream of the BnMYB103-1 ATG start codon.

SRK7 -
5' CCAATGGGATCCAAAATGAATCA 3' (SEQ ID NO. 50)

23mer situated at the 3' end of BnMYB103-1 including the TGA stop codon.

Isolation of Plasmid DNA:

Alkaline-Lysis Extraction

A rapid alkaline extraction method for the isolation of plasmid [Birnboim, 1983 Enzymology 100: 243-255].

Alkaline-Lysis/PEG Precipitation Procedure for Sequencing

Plasmid DNA for sequencing was prepared using the modified "mini" alkaline-lysis/PEG precipitation procedure outlined in User Bulletin Number 18 from Perkin Elmer. Appendix A of the PRISM'Ready Reaction DyeDeoxy™ Terminator Cycle Sequencing kit protocol Rev.A Restriction Enzyme Digests 0.5-1.0 μg DNA was digested in a 20 μl reaction using 2 μl of the required 10× buffer and 2-4 units of the appropriate restriction enzyme. The reaction mix volume was made up to 20 μl with deionised water and incubated for 1-2 hours at the appropriate temperature.

Resolution of DNA Fragments

Agarose gel electrophoresis was used to resolve DNA fragments. The agarose concentrations ranged from 0.5-1.0% (w/v) agarose, [Maniatis, 1982 Molecular Cloning: A Laboratory Manuel: Cold Spring Harbour, New York].

Isolation and Purification of DNA Fragments

The BRESAclean® DNA purification kit was used to purify DNA fragments from agarose gels.

Subcloning of DNA Fragments

Vector DNA was digested with appropriate restriction enzymes as described in section 2.2.3. The restriction enzymes were heat inactivated at 70° C. for 15 minutes before treating the lineralised vector with calf intestinal phosphatase (CIP) to remove the 5' phosphate residues. This was achieved by adding 2 μl of 10×CIP buffer plus 1.4 units of CIP to the reaction mix and incubating for 20 minutes at 37° C. [Maniatis, 1982 supra]. To remove contaminating proteins and salts 400 μl of Wizard™ purification resin was added to the reaction. It was mixed by inversion for 1 minutes and passed through a Wizard™ minicolumn as per manufactures instructions. 150-300 ng fragment DNA and 50-100 ng of vector DNA was incubated in the presence of 3 units of T4 DNA ligase and 1 μl of 10× T4 DNA ligase buffer in a total volume of 10 μl at room temperature for 2-4 hours (sticky end ligation) or at 15° C. overnight (blunt end ligation) [Ausubel, 1994 supra].

Preparation of Electrocompetent E. Coli Cells

A single colony of the E. coli strain to be prepared was inoculated into a 5 ml overnight culture of 2YT broth (log yeast extract, 16g tryptone, 5g NaCl, per liter, pH 7.0) containing 10 mM $MgSO_4$ and grown at 37° C. This was diluted into 500 ml of 2YT containing 10 mM $MgSO_4$ and grown in two one liter flasks with shaking at 37° C. When the optical density at 550 nm reached between 0.8-1.0 the cultures were cooled on ice for 1 hr. The cells were then pelleted by centrifugation at 4° C. for 5 min. at 5000×G. The supernatant was discarded and the cells resuspended in 10 ml of ice cold 1 mM HEPES, pH 7.0. 200 ml of the HEPES was then added and the cells mixed by gentle inversion. This step was repeated and the supernatant discarded. The cells were resuspended in 200 ml ice cold 15% (v/v) glycerol and pelleted. Following centrifugation the supernatant was discarded and the cells resuspended in the glycerol remaining in the tube. Aliquots of the cells were frozen in microfuge tubes using liquid nitrogen and stored at −70° C.

Electroporation of E. Coli Cells

1 μl of a ligation reaction or 25 ng of plasmid DNA was added to 40 μl of thawed electrocompetent cells and incubated on ice for 1 minute. The cells were then transformed using the Invitrogen Eletroporator II. Cuvettes with a 0.1 cm gap were used and the apparatus set to 1.5 kV, 50 μF and 150 ohms. Electroporation was performed according to the manufacturers instructions. 200 μl of SOC broth was added to the transformed cells and incubated at 37° C. for 1 hour. The cells were then plated onto appropriate selective media and incubated overnight at 37° C.

Screening of Plasmid Size

The colonies to be screened were patched onto appropriate media and grown overnight at 37° C. A sterile toothpick was used to remove and resuspend cells in 40 μl of 10 mM Tris-HCl, pH8.0, 100 mM NaCl, 10 mM EDTA in a microfuge tube. An equal volume of phenol-chloroform-isoamyl alcohol (25:24:1) and 5 μl of stop mix was then added. The tubes were vortexed then centrifuged at full speed for two minutes. 20 □l of the aqueous layer was loaded onto an agarose gel for electrophoresis and analysis using a vector-only sample as a marker. Constructs found to be larger that the vector were then further assessed via restriction enzyme analysis.

DNA Sequencing

Dye terminator cycle sequencing was performed using the ABI Prism® BigDye™ Terminator Cycle Sequencing Ready Reaction kit from Perkin-Elmer and template prepared according to the manafacturers instructions. An MJ Research MiniCycler™ (PTC-150) was used to amplify the extension products with the following parameters, 96° C. for 30 seconds, 50° C. for 15 seconds and 60° C. for 4 minutes. This cycle was repeated twenty five times. The extension products were precipitated, dried under vacuum and sent to the Microbial Biotechnology and Diagnostic Unit at Monash University (Melbourne, Australia) for electrophoresis.

The Polymerase Chain Reaction

DNA amplification was performed using taq DNA polymerase and the MJ Research MiniCycler™ with Hot Bonnet™. The reaction mixture contained the following components, taq DNA polymerase reaction buffer (1×), MgCl (ranging from 1.0-2.0 mM), dNTP's (200 μM each dNTP), primers (10 μM each primer), template DNA (5-long), taq DNA polymerase (2.5 units) and double distilled water to make the final volume of 20 μl. Cycling parameters varied according the size of the fragment to be amplified and $T_m$ of the primers.

Extraction of Total RNA

The method used is a modification of the procedure by [Logemann, 1987 Analytical Biochemistry 163: 16-20] for RNA extraction from plant tissue. One gram of plant tissue was frozen in liquid nitrogen and ground to a fine powder using a mortar and pestle. The powder was transferred to a 15 ml tube and 2 ml of extraction buffer (8M guanidine hydrochloride, 20 mM MES, pH7.0, 20 mM EDTA, 50 mM mercaptoethanol) added. Three milliliters of phenol/chloroform (phenol/chloroform/iso-amylalcohol, 25:24:1) was added and the tube shaken to extract the nucleic acids. The tube was centrifuged for 10 min at 3,000×G, the upper phase transferred to a new tube containing 3 ml phenol/chloroform and the extraction and centrifugation steps repeated. The upper phase was transferred to another 15 ml tube containing 0.2 volumes 1M acetic acid and 0.7 volumes freezer-cold ethanol. The RNA was allowed to precipitate at −20° C. overnight. The tube was centrifuged for 25 min at 9500×G, the supernatant removed and the pellet air dried for 2 min. The pellet was then resuspended in 1 ml of DEPC-saturated water, transferred to a 1.5 ml microfuge tube and LiCl added to a final concentration of 2M. The tube was mixed and incubated overnight at 4° C. The tube was centrifuged for 15 min at full speed at 4° C. The supernatant was discarded and the pellet resuspended in 500 μl DEPC-saturated water. To this was added 50 μl 3M Na-acetate, pH5.2, and 100041 freezer-cold ethanol. This was mixed and incubated overnight at −20° C. The mixture was centrifuged at full speed for 15 min at 4° C., the pellet resuspended in DEPC-saturated water at a final concentration of 5 μg/ml and stored at −70° C.

Quantification of Total RNA

An aliquot of total RNA was diluted 1/1000 in 1×THE buffer (10×-100 mM Tris base, 10 mM EDTA, 2.0M NaCl, pH 7.4) and absorption of the sample measured at different wave lengths to determine concentration and purity. Absorbance at 260 nm was used to determine concentration. The ratio of absorbance at 260 and 280 nm was used to indicate purity and absorbance at 325 nm to indicate contaminating particulate matter.

Isolation of Polyadenylated RNA

Dynabeads® Oligo $(dT)_{25}$ were used to isolate polyadenylated RNA from total RNA according to the manufacturers instructions.

Reverse Transcriptase Polymerase Chain Reaction (RT-PCR)

SuperScript™ II Rnase H⁻ reverse transcriptase (Gibco BRL) was used to synthesize first strand cDNA according to the manufacturers instructions using gene specific primers. This first strand cDNA was used in a PCR to amplify the fragment of interest according to the protocol suggested by the manufacturer.

Extraction of Genomic DNA from *Arabidopsis*

2-5g of ground frozen tissue was transferred to a 50 ml tube containing 25 ml of CTAB extraction buffer. The sample was shaken vigorously and incubated at 65° C. for 20 minutes with occasional shaking. 10 ml of chloroform was added to the sample and placed on an inverter for 20 minutes. To resolve the phases, the sample was centrifuged for 5 minutes at 3,000 rpm in a bench top centrifuge. The aqueous phase was transferred into a fresh 50 ml tube containing 17 ml of isopropanol, mixed, and incubated on ice for 10 minutes.

The sample was centrifuged at 3,000 rpm for 5 minutes and the supernatant was discarded. The precipitate was resuspended in 4 ml of TE buffer by gently passing the solution up and down a pipette tip. 4 ml of 4 M LiAc was added and the sample was incubated on ice for 20 minutes. The sample was centrifuged for 5 minutes at 3,000 rpm. The supernatant was discarded and the pellet resuspended in 900 μl of TE buffer. To remove contaminating RNA, 25 μg/ml of RNase was added and incubated at 37° C. for 5 minutes. 100 μl of 3M NaOAc was added, mixed, and divided equally into two microfuge tubes. The samples were extracted with 500 μl of buffered phenol (pH 8.0), buffered phenol:chloroform (1:1) and chloroform, the aqueous phase was transferred to a fresh microfuge tube after each extraction. Two volumes of 100% ice cold ethanol was added and the samples incubated on ice for 5 minutes. The DNA precipitate was collected by spinning the samples for 5 minutes at 13,200 rpm at 4° C. The supernatant was discarded, the pellet washed twice with ice cold 70% (v/v) ethanol, dried under vacuum and resuspended in 200 μl of sterile deionised water.

DNA Quantification

DNA was diluted 1/1000 in TEN buffer and absorbance measured at 260 nm. The ratio of absorbance at 260 and 280 nm was used to indicate purity.

Construction of *Brassica Napus* cDNA Library

A *B. napus* flower-bud cDNA library was constructed using the ZAP Express® cDNA synthesis kit and ZAP Express® cDNA Gigapack®III Gold cloning kit from Stratagene. Total RNA was extracted from *B. napus* flower-buds using the protocol outlined above and poly(A)⁺ RNA isolated using Dynabeads. The synthesis of cDNA was carried out using 5 μg of poly(A)⁺ RNA and subsequent steps required for construction of the cDNA library were performed according to the instruction manual accompanying the kit (Revision #080012 and #200403-12). Plaque lifts, library screening and in vivo excision were all performed according to the instruction manual.

Northern Blotting

Approximately 3 μg of Poly(A)⁺ RNA from each sample was electrophoresed on a 1% agarose gel (50% formamide) with an RNA molecular marker (Promega). The RNA was blotted onto a positively charged nylon membrane (Hybond N, Amersham) using the upward capillary method of transfer [Ausubel, 1994 supra]. The filter was prehybridised (5×SSC, 5×Denhardt's, 1% SDS, 50% formamide with 100 μg/ml salmon sperm DNA) for two hours at 42° C. The probe was labeled with $^{32}$P dCTP (250 μCi, Geneworks) using the Megaprime DNA labeling kit (Amersham). Unincorporated nucleotides were removed using a Nickspin column (Amersham). The denatured probe was added to the prehybidisation solution in a glass tube and allowed to hybridise to the filter overnight at 42° C. with constant rotation in a Hybaid oven. Post hybridisation stringency washes included 2×SSC, 0.1% SDS at RT for 2×5 min; 0.2×SSC, 0.1% SDS, at RT for 2×15 min and 0.2×SSC, 0.1% SDS, at 42° C. for 2×15 min. The filter was then wrapped in plastic and exposed to x-ray film overnight at −70° C. in a film cassette.

Methods: Plant Transformation

The plant transformation protocol described below is based on methods devised by Lazo, 1991 supra and modified by C. Johnson, Department of Genetics and Developmental Biology, Monash University, (Melbourne, Australia).

Tri-Parental Mating

Fresh liquid cultures of *Agrobacterium tumefaciens* (AGLI strain), *E. coli* containing the required binary vector with insert and *E. coli* containing the plasmid pRK2013, were prepared. A 100 μl aliquot of each culture was mixed in a tube then plated onto 2YT plates and incubated overnight at 28° C. Two streaks of cells were resuspended in 100 μl of 2YT broth. The resuspended cells were streaked for single colonies on 2YT plates containing 75 µg/ml kanamycin and 100 µg/ml ampicillin. Several single colonies were inoculated in 2YT broth containing the appropriate antibiotics and grown for 2 days at 28° C. with vigorous shaking. Plasmid DNA extracted from the culture was used in a PCR with insert specific primers. Presence of the amplified insert indicates that successful tri-parental mating has occurred.

Growth and transformation of *Arabidopsis thaliana* roots *Arabidopsis thaliana* seeds were surface sterilised in a microfuge tube by washing the seeds with 0.5 ml of 70% (v/v) ethanol. The ethanol was removed, replaced with seed sterilising solution (4% chlorine, water, 5% SDS at a ratio of 8:15:1 respectively) and incubated for 10 minutes. The seed sterilising solution was removed and the seeds washed several times in sterile water. Sterilised seeds were sown into 12.5 mm petri dishes containing 50 ml of GM media and sealed with micropore tape. The seedlings were grown at 22° C. for 2 weeks under constant illumination (80 µm$^{-2}$s$^{-1}$)

Roots harvested from *Arabidopsis* plants were placed parallel onto CIM plates and sealed with micropore tape. The plates were wrapped in foil and incubated at 22° C. for 2 days. The roots were cut into 0.5 cm pieces, added to liquid cultures of AGLI, shaken and strained through a sterilised steel tea strainer. Excess AGLI was removed by lightly blotting onto sterile 3MM paper and the roots spread over a CIM plate. The plates were sealed with micropore tape, wrapped in foil and incubated for a further 2 days at 25° C. Roots removed from CIM plates were washed to remove bacteria by vigorous shaking with sterile water in 50 ml tubes. A sterile steel tea strainer was used to strain the roots, and they were blotted dry on sterile 3 mM paper. The roots were carefully spread over SIM media containing 100 µg/ml kanamycin and 200 µg/ml timetin, sealed with micropore tape and incubated at 22° C. under constant illumination (80 µEm$^{-2}$s$^{-1}$)

Selection of Transformants

Shoots produced from root cultures were transferred into 150 mm pots containing GM media with 50 µg/ml kanamycin and 200 µg/ml timentin. A small leaf from each shoot was used to check for successful transformation. The leaf was placed into a microfuge tube with 40 µl of 0.25M NaOH, boiled for 30 seconds and neutralised by adding 40 µl 0.25 MHCl and 20 µl 0.5M Tris-HCl (pH 8.0) containing 0.25% (v/v) Nonident P-40 before boiling for a further 2 minutes. The leaf sample was immediately used for PCR as described above. An amplified PCR product of the desired size indicated that successful transformation had occurred. Transformed shoots containing the insert of interest were grown to maturity Histochemical Assay of Transformed *Arabidopsis* Plants Seeds generated from plants transformed with pBI101 containing the promoter::gusA construct were surfaced sterilised and sown onto GM plates containing 50 µg/µl kanamycin and grown under constant illumination at 22° C. for 2 weeks. Germinated plants that retained their chlorophyll content were transferred to soil. Floral clusters were removed from the plant and placed into a microfuge tube containing X-gluc solution and incubated at 37° C. for 12-15 hours. The chlorophyll was leached from the plant tissue by placing the tissue into 100% ethanol. GUS staining was examined under a dissecting microscope.

Staining, embedding and sectioning of transformed plants Floral heads were pre-fixed with 1% (v/v) glutaraldehyde made up in 50 mM sodium phosphate buffer (pH 7.4) for 5 minutes at room temperature. Tissue was washed 4 times with 50 mM sodium phosphate buffer (pH 7.4) for 5 minutes each time. The tissue was covered with X-gluc and incubated overnight at 37° C. The tissue was post-fixed in a solution of 6% (v/v) glutaraldehyde and 4% (v/v) paraformaldehyde made up in 50 mM sodium phosphate (pH 7.4) and incubated for 2 hours at 4° C. after 1 minute vacuum infiltration. The tissue was washed three times with 50 mM sodium phosphate buffer (pH 7.4) for 5 minutes each time. The floral heads were slowly dehydrated by incubating them for 15 minutes each time with increasing concentrations of ethanol (15%, 50%, 70%, 90% and 100% (v/v)). The tissue was transferred into a fresh tube containing 30% LR white:70% ethanol (v/v) and incubated at room temperature for one hour. This solution was replaced with 50% LR white:50% ethanol (v/v) and incubated for a further hour. The tissue was placed in 100% LR white and incubated overnight at 4° C. The next day, the tissue samples were placed into plastic boats; covered with 100% LR white; covered to exclude oxygen and incubated overnight at 65° C. Embedded plant tissue was mounted on a microtome, cut into 10 µm sections and mounted on a clean slide. The sections were stained with 1% (w/v) safranine dye for 2 minutes with gentle heating. Excess dye was washed off with water and then with 50% (v/v) ethanol. Finally the sections were rinsed with 100% ethanol, arranged on the slide and dried with gentle heating. A small drop of clearene and 4 small drops of mounting medium were placed on the sections. The sections were covered with a coverslip and placed on a slide heater. The slide was incubated overnight at 50° C. with a small weight of 200 grams placed on top. The slides were viewed under the light microscope.

Electron Microscopy

Samples analysed using the scanning electron microscope were critical point dried in liquid $CO_2$. The samples were coated with palladium-gold and examined using a JEOL JSM 6340F field emission scanning electron microscope.

Flower buds at various stages of development were embedded in LR White Hard according to Chaudhury et al. (1994) supra. Sections of 70-90 nm were mounted on 50-100 nm FORMVAR coated copper grids and double stained in uranyl acetate for 6.5 minutes followed by staining in lead citrate for 1.5 minutes. The stained sections were then examined at 80 kV in a JEOL 2010 transmission electron microscope.

Results

Isolation of clone p8.1.1 from a *B. napus* cDNA library The isolation of an AtMYB103 homologue from *B. napus* began with the construction of a flower bud cDNA library (see above). Flower buds representing a number of developmental stages, from 0.5 mm to the point before flower opening were used for the extraction of RNA. Flower buds of these sizes contain microspores at a variety of developmental stages. These include meiocytes, tetrads and newly released microspores in the smaller buds and binucleate or trinuleate microspores prior to anthesis in the largest buds.

Figure 10:
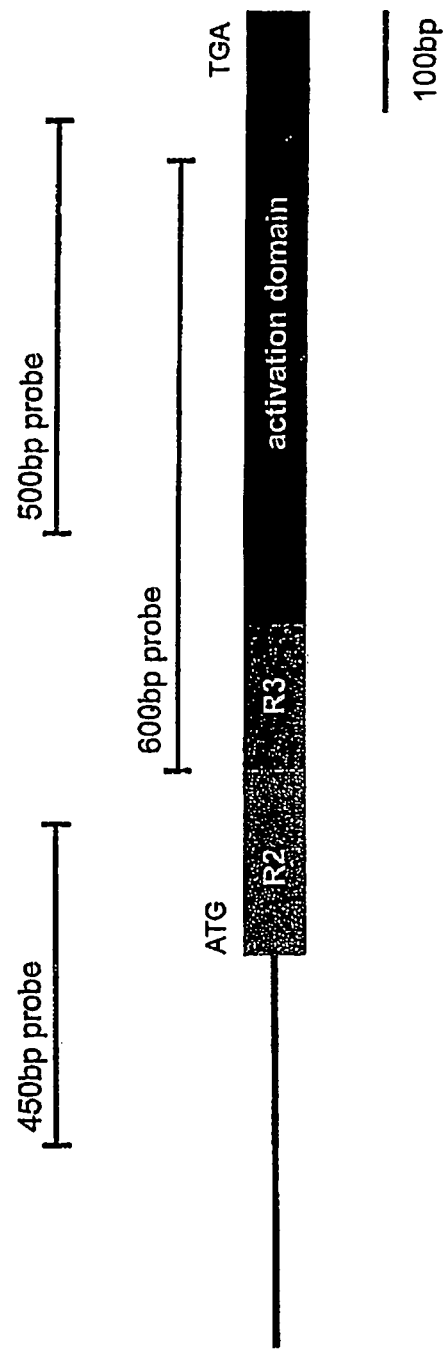
FIG. 10 illustrates AtMYB103 (SEQ ID NO. 23) probes used to screen B. napus cDNA (600 bp) and genomic DNA (450 by and 50bp) libraries.

The cDNA library was screened using a 600 bp probe derived from AtMYB103 including the R3 repeat and part of the C-terminal region, (FIG. 10). An initial screen of $1 \times 10^6$ plaques led to the isolation of four clones following tertiary screening at high stringency (0.2×SSC, 0.1% SDS, 65° C.). These four clones were sequenced and found to be identical.

The clone p8.1.1 consists of an ORF 969 bp long with a putative amino acid sequence of 323aa. It contains the imperfect R2R3 repeats characteristic of plant MYB genes, including conserved tryptophan residues. However, compared with AtMYB103 it shows an overall identity of 43% at the nucleotide level and 31% identity at the amino acid level (FIG. 11). A BLASTN search of the NCBI data base gave the following results. At the nucleotide level the highest identity is with an *A. thaliana* putative transcription factor, MYB35 (AF062877) with a score of 361 $4e^{-97}$. This partial sequence contains only 27 bp of the R2 repeat but shows significant homology within the repeat region, namely 92%. Portions of significant homology occur at the 3' end of the sequence with an overall identity of 62%. Romero et al. (1998) The Plant J. 14: 273-284 identified MYB35 in a systematic search for R2R3-MYB regulatory genes in the genome of *A. thaliana* but no functional characterisation has been reported. A phylogenetic tree based on the amino acid sequence outside the R2R3 domain classifies the MYB proteins into 22 subgroups [Romero, 1998 supra]. However, MYB35 does not fall within any of these subgroups. A BLASTP search showed highest identity with a transcription factor-like protein found on chromosome three of *A. thaliana*. This protein has a 95.6% identity in the R2R3 region and an overall identity of 75% with the clone p8.1.1.

Both the BLASTN and BLASTP searches showed identity to AtMYB103 with scores of 62 $5e^{-07}$ and $2131e^{-54}$ respectively. This may be considered significant, however the greatest identity between these sequences is in the conserved R2R3 repeats showing 69% identity at the amino acid level. The overall amino acid identity is only 31%, indicating that clone p8.1.1 is unlikely to represent an AtMYB103 homologue.

Isolation of an AtMYB103 homologue from a *B. napus* genomic library A *B. napus* genomic DNA library (Clonetech FL112d) was screened in this laboratory by Roger Kalla (personal communication) with AtMYB103 3' and 5' probes mixed (FIG. 11). The 3' probe was gene specific and excluded the R2R3 repeats. The 5' probe includes 130 bp of the R2 repeat and 320 bp of the sequence upstream from the ATG start codon. This screening identified two recombinant phage particles containing homologous sequences. Sequence data from these clones show a gene of similar structure to AtMYB103 consisting of three exons interrupted by two introns at conserved sites (FIG. 12). An ORF of 960*bp* coding for a protein of 320aa similar to that of AtMYB103 was identified (FIG. 13). This clone, BnMYB103-1, shows 93% identity to AtMYB103 at the amino acid level, with 99% identity in the R2R3 region and 89% identity in the putative activation domain (FIG. 14). A BLASTP search showed the highest score of $561e^{-159}$ with AtMYB103.

Figure 15:
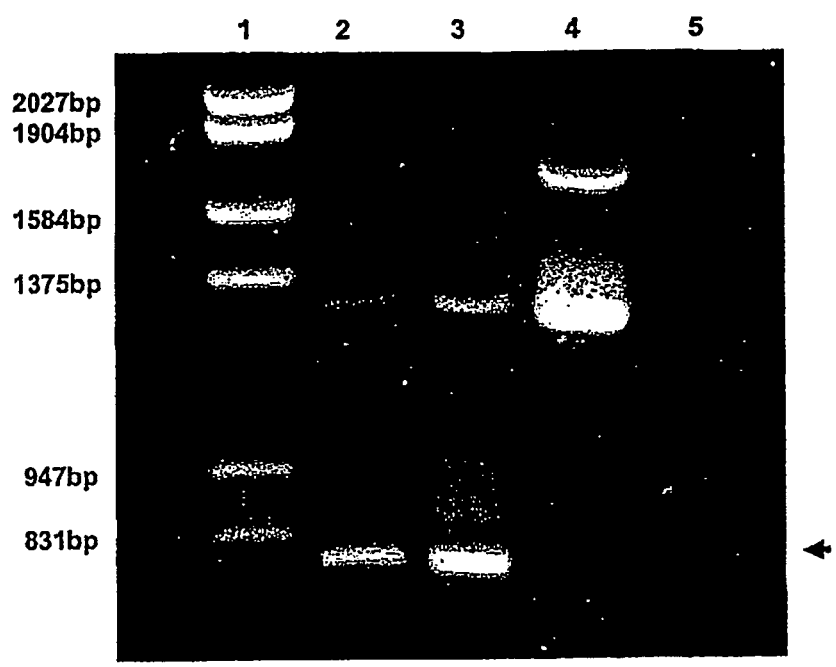
FIG. 15 shows the 700 by RT PCR product. The large product represents amplification from genomic DNA.
Lane 1 AEcORI/HindIII marker
Lane 2 700bp RT PCR product (1.5 mM MgCl$_2$)
Lane 3 700bp RT PCR product (2.0 mM MgCl$_2$)
Lane 4 products from B.napus genomic DNA
Lane 5 no DNA

Isolation of Clones p700-1, p800-19 and p900-10 Using the Reverse Transcriptase Polymerase Chain Reaction RT PCR was used in an attempt to isolate an AtMYB103 homologue. First strand cDNA derived from the polyA+ RNA of immature *B. napus* flowers was used as template in a reaction with AtMYB103 specific primers. A 700 bp product was obtained as a result of two rounds of amplification using nested primers. The first reaction used primers A5962H02 and A6004A01 situated at the 5' start site and putative 3' stop site of the AtMYB103 sequence respectively. (Subsequent analysis of the 3' region of AtMYB103 has placed the stop codon further downstream). A set of nested primers, A5956A10 and A2485F04 were then used to ensure specificity of the amplified product (FIG. 15). The 700 bp product was cloned as a blunt ended fragment into the Sma I site of pBluescript. Sequence comparison of the 700 bp RT PCR product, p700-1 (SEQ ID NO. 24), with AtMYB103 shows 93% identity at the amino acid level, 99% identity in the R2R3 region and 89% in the 3' region, although this sequence is incomplete (FIG. 16).

Figure 17:
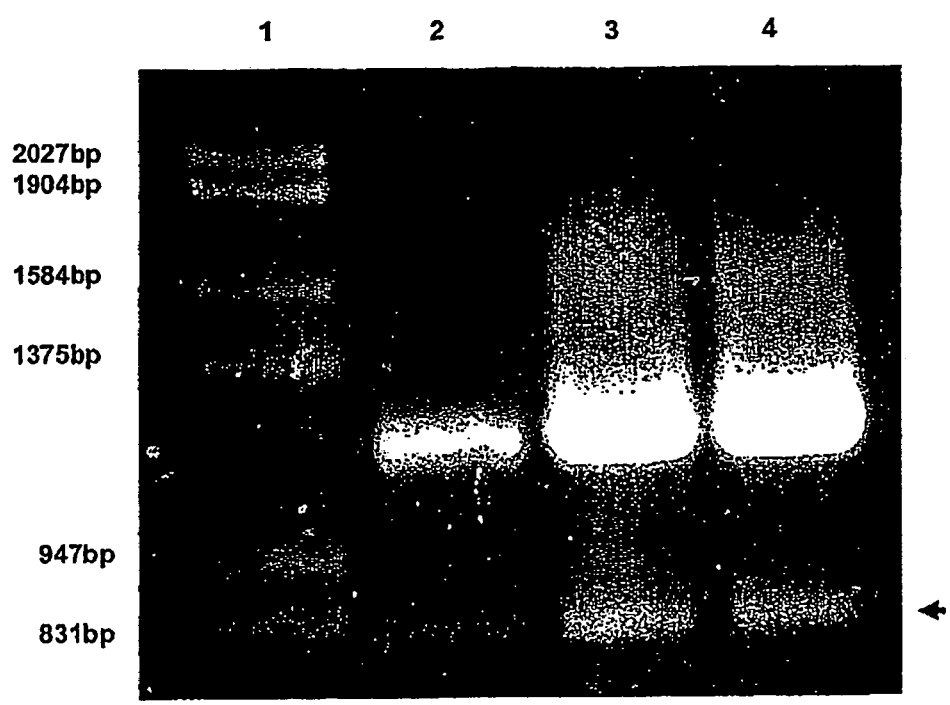
FIG. 17 shows the 800bp RT PCR product. The arrow indicates 800 by RT PCR product. The large product represents amplification from genomic DNA.
Lane 1 AEcORI/HindIII marker
Lane 2 800bp RT PCR product (1.0 mM MgCl$_2$)
Lane 3 800bp RT PCR product (1.5 mM MgCl$_2$)
Lane 4 800bp RT PCR product (2.0 mM MgCl$_2$)

Further RT PCR was performed using primers designed from the gDNA sequence and first strand cDNA obtained from immature *B. napus* flowers as template. The first round of PCR was performed using primers SRK1 and SRK7 situated at the 5' end upstream of the ATG start and at the 3' end including the TGA stop respectively. No products of the expected size were observed following electrophoresis on an agarose gel. A second round of PCR was performed using the first round PCR products as template with SRK2, a primer 180 bp downstream of SRK1, and SRK7. This time a product of approximately 800 bp was amplified which corresponds to the expected size of 805 bp (FIG. 17). Cloning and subsequent sequencing of this product (p800-19—SEQ ID NO. 25)) shows 99% identity to the genomic BnMYB103-1 sequence, with only three nucleotide differences. These differences may reflect the different cultivars used to produce the gDNA and cDNA libraries. Compared with AtMYB103 there is an overall amino acid identity of 93%, with 99% identity in the R2R3 region and 89% identity in the putative activation domain (FIG. 18). Screening of the *B. napus* flower cDNA library with a 350 bp 3' probe (gene specific) derived from this RT PCR product failed to give any positive signals.

Figure 19:
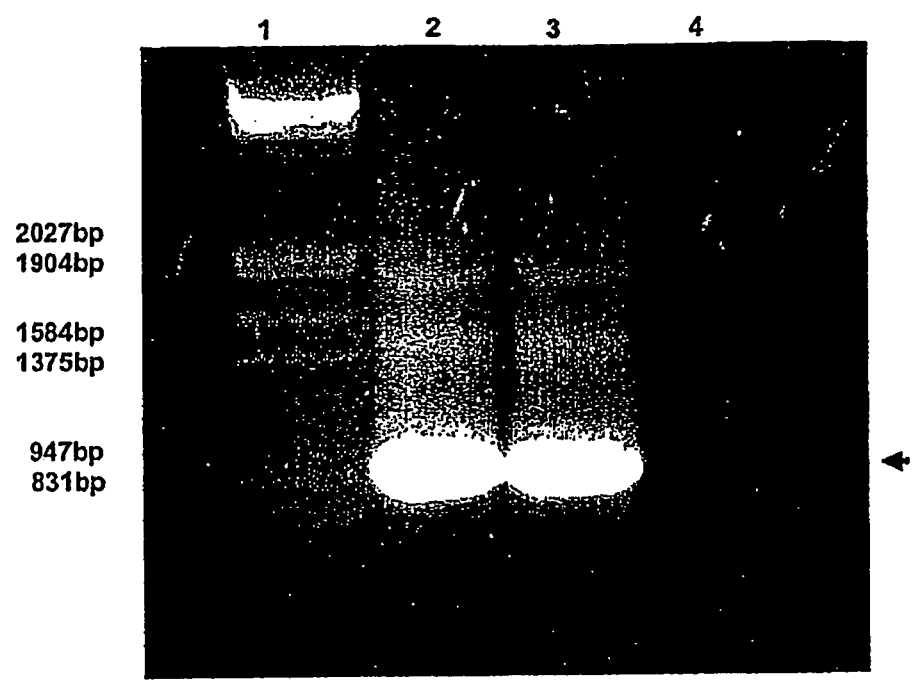
FIG. 19 shows the 950bp RT PCR product. The arrow indicates 950bp RT PCR product.
Lane 1 AEcORI/HindIII marker
Lane 2 950bp RT PCR product (2.0 mM MgCl$_2$)
Lane 3 950bp RT PCR product (2.5 mM MgCl$_2$)
Lane 4 no RNA

Using new primers designed from the AtMYB103 sequence another round of RT PCR was performed. First strand cDNA was generated from polyA+ RNA extracted from immature *B. napus* flower buds using the primer Z1346E10. This primer is situated at the 3' end of the gene and includes the TGA stop codon. This was used in a PCR with primers A5962H02, situated at the 5' end including the ATG start and Z1346E10. A 950 bp product was generated, the approximate size predicted from the AtMYB103 sequence (FIG. 19). This product was cloned (p900-10—SEQ ID NO. 26)) and sequenced and shares 97% identity with AtMYB103 at the amino acid level (FIG. 20). It also shares homology with p800-19 and BnMYB103-1, although the greatest homology is with p700-1.

A BLASTN and BLASTP search of the Genbank data base with p700-1, p800-19 and p900-10 all produce the most significant alignment with AtMYB103. Scores of 394 $e^{-107}$, 428 $e^{-117}$ and 407 $e^{-117}$ respectively, were obtained at the nucleotide level. Scores of 520 $e^{-146}$, 434 $e^{-121}$ and 450 $e^{-126}$ respectively, were obtained at the amino acid level. A Southern blot of *B. napus* genomic DNA probed with the 3' end of p700-1 (R. Kalla, personal communication) indicates that at least four different homologues of this gene are present in *B. napus*. *Brassica napus* which originates from a cross between *B. rapa* AA (n=10) and *B. oleracea* CC (n=9) contains an AACC genome. Southern blotting of genomic DNA from these parental species and probing with the same p700-1 probe provides evidence for at least two homologues in each organism (results not shown).

The fact that these four clones, BnMYB103-1, p700-1, p800-19 and p900-10, were isolated from *B. napus* flower buds and share significant identity with each other is in keeping with the amphidiploid nature of *B. napus*. Their homology to AtMYB103 is in keeping with other *Brassica* genes that have been isolated in a similar manner. FIG. 21 gives an overview of homology between these four clones and AtMYB103. It is likely that these four clones are homologues of AtMYB103.

BnMYB103-1, a Likely Orthologue of AtMYB103

Figure 8:
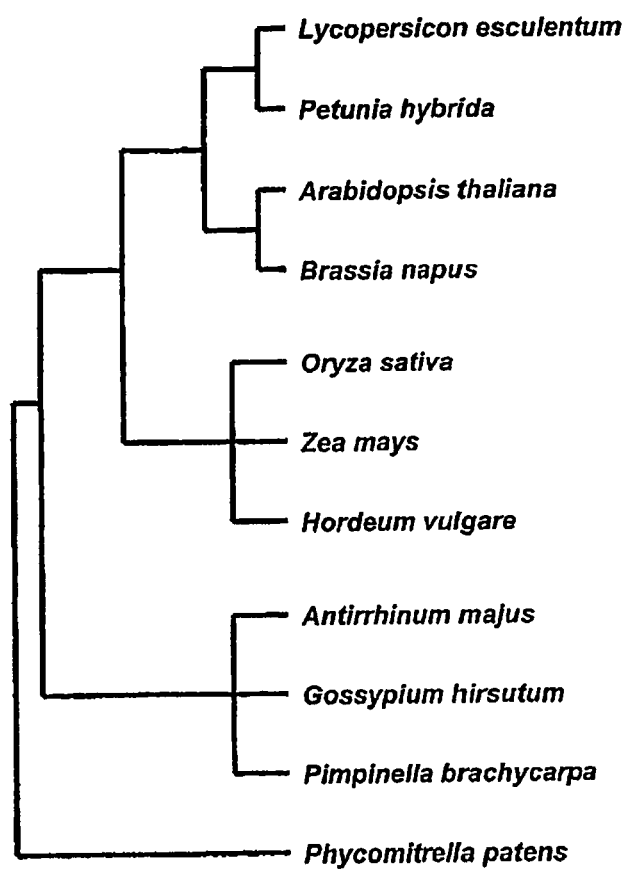
FIG. 8 illustrates a species tree generated from a list of potential BnMYB103-1 orthologues derived from an orthologue search of the NCBI database. Each species is represented by one or more MYB genes (see FIG. 9).
Figure 9:
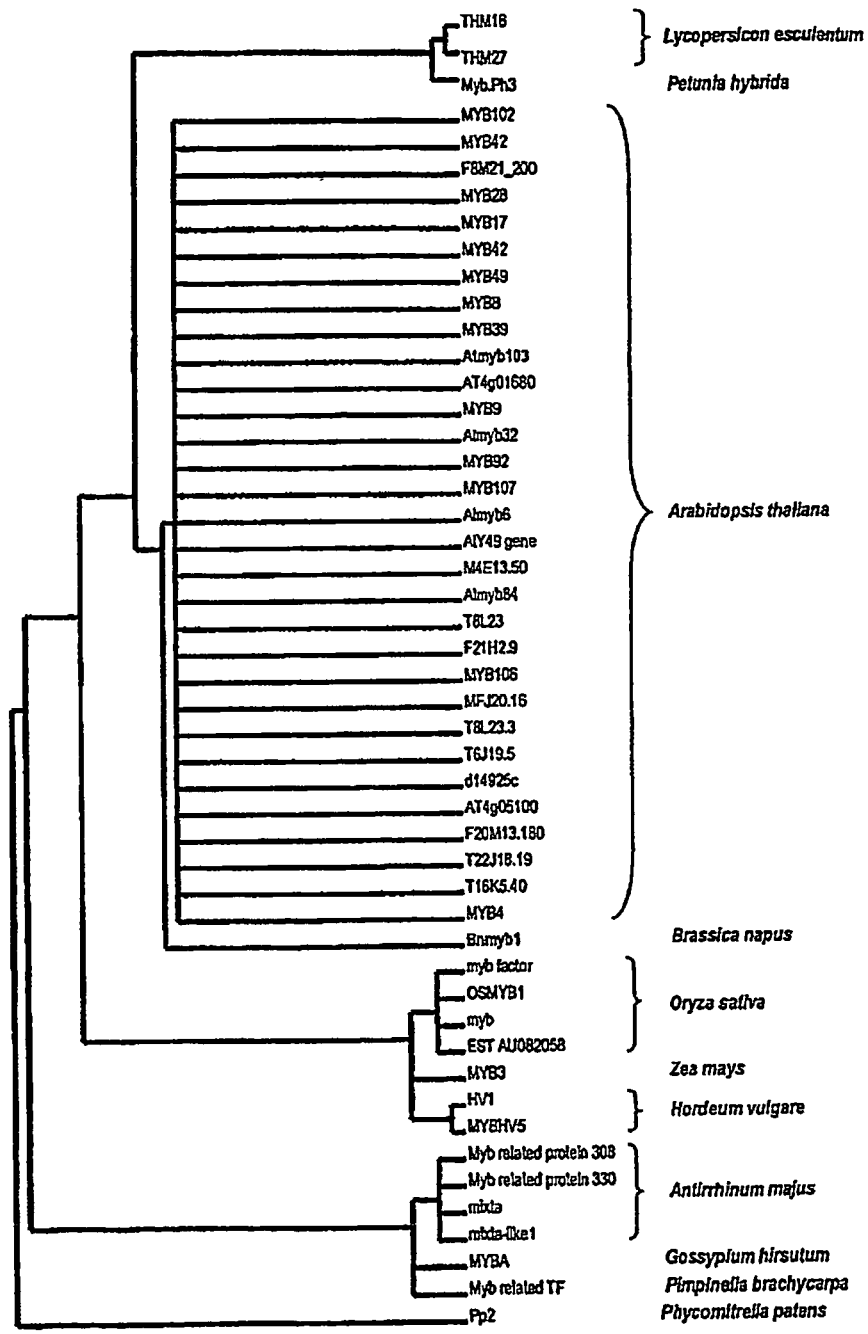
FIG. 9 illustrates a gene tree of plant MYB genes related to BnMYB103-1, (SEQ ID NO. 4) AtMYB103 (SEQ ID NO. 23) and BnMYB103-1 (SEQ ID NO. 4) are shown in bold.

The Advanced BLAST2 and Orthologue Search Service at EMBL was used to find sequences likely to represent orthologues of BnMYB103-1. Using the BnMYB103-1 amino acid sequence as the query sequence the highest score of 1449 $3.6e^{-148}$ was obtained for AtMYB103. The other genes shown in this analysis are all MYB genes or described as MYB-like. Further analysis using this service produced a species tree using the NCBI database and a gene tree based on the neighbour-joining tree computed by CLUSTALW (FIGS. 8 & 9).

The taxonomic tree shows the closest evolutionary relationship between the *B. napes* query sequence and the *A. thaliana* sequences. The sorting of genes according to this taxonomic tree groups BnMYB103-1 with thirty-one *A.*

*thaliana* sequences. Fifteen of these are MYB genes the others are described as MYB-related or transcription factor-like proteins.

Expression Pattern of BnMYB103-1

The expression pattern of a gene may be determined using a variety of methods. Reporter genes such as gusA fused to a specific promoter are useful for determining temporal and spatial expression patterns. More sensitive and specific methods include Northern blotting, RT PCR and in situ hybridisation. These techniques involve detection of mRNA that has been transcribed from the gene of interest. Where the gene under investigation is expressed only in certain tissues and at specific stages of development it is important to have reporter gene information regarding expression of the gene in the whole plant as guide to the selection of material. BnMYB103-1 promoter-gusA studies were followed by a more detailed analysis of BnMYB103-1 expression using Northern blotting and RT PCR.

BnMYB103-1 Promoter-gusA Expression Patterns

A 725 bp region upstream of the BnMYB103-1 start site was cloned into the Sal I/Xba I sites of pBI101.2 immediately upstream of gusA reporter gene. When transformed into *A. thaliana*, the X-Gluc stained inflorescences showed GUS staining only in the anthers of immature flowers. This corresponds to the staining pattern observed using the AtMYB103 promoter-gusA construct (FIG. 22).

Figure 23:
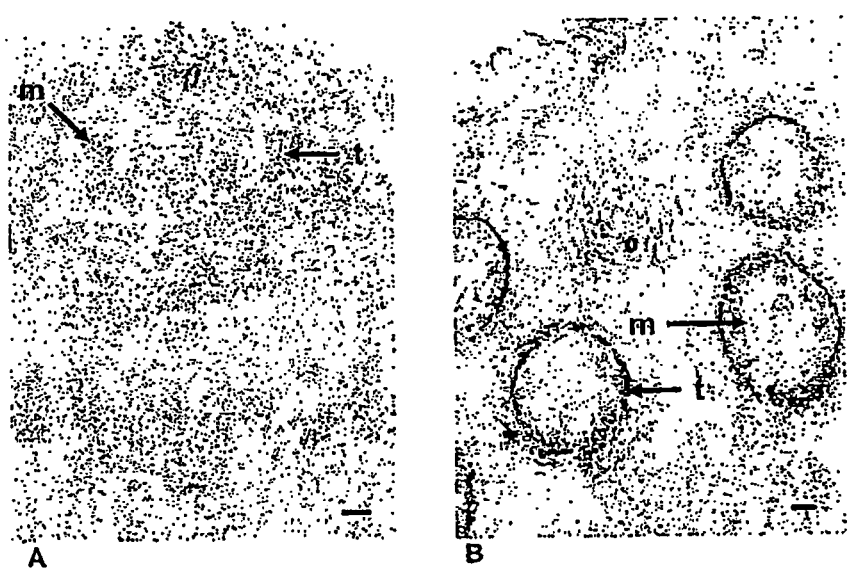
FIG. 23 shows sections of GUS stained anthers from A. thaliana. A shows anthers from a plant carrying an AtMYB103 promoter-gus A construct (Bar =20 μm). B shows anthers from a plant carrying BnMYB103-1 promoter-gus A construct (Bar =30 μm). GUS staining is confined to the tapetum (t) and microspores (m).

Sections through these stained anthers show that GUS expression is found in the tapetum and microspores (FIG. 23)

Northern Blot Analysis of *B. Napus* Tissues

The method used follows the protocol outlined by Ausubel et al. (1994) supra. *Brassica napus* tissues from different stages of development were selected for analysis. These included the roots and shoots from ten day old seedlings, anthers harvested from flower buds 2-6 mm in length, mature dehiscing anthers and flower buds of different sizes. The flower buds were divided into three groups representing different developmental stages, 0.5-2 mm, 2.5-5 mm and 6-8 mm in length. Flower bud length has been correlated with the stages of anther and pollen development (data not shown).

Total RNA was extracted using Trizol reagent (Gibco). The integrity of RNA was assessed via agarose gel electrophoresis. Absorbance readings on a spectrophotometer at 260 and 280 nm were taken to assess the purity of RNA extractions using the $A_{260}$ to $A_{280}$ ratio. The $A_{260}$ reading was also used to calculate the concentration of RNA in each sample. PolyA$^+$ RNA was extracted from total RNA using oligo dT dynabeads (Dynal) according to the manufacturer's instructions. For each sample, 75 μg of total RNA was used in the extraction to obtain approximately 3 μg of PolyA$^+$. RNA.

Figure 24:
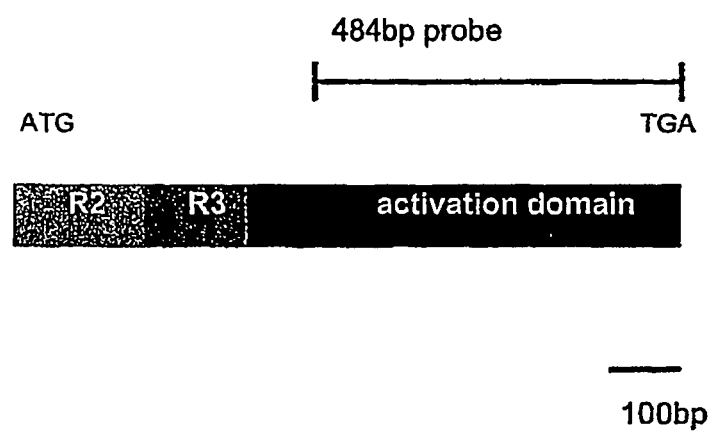
FIG. 24 illustrates the BnMYB103-1 (SEQ ID NO. 4) fragment used to probe B. napus Northern blot.
Figure 25:
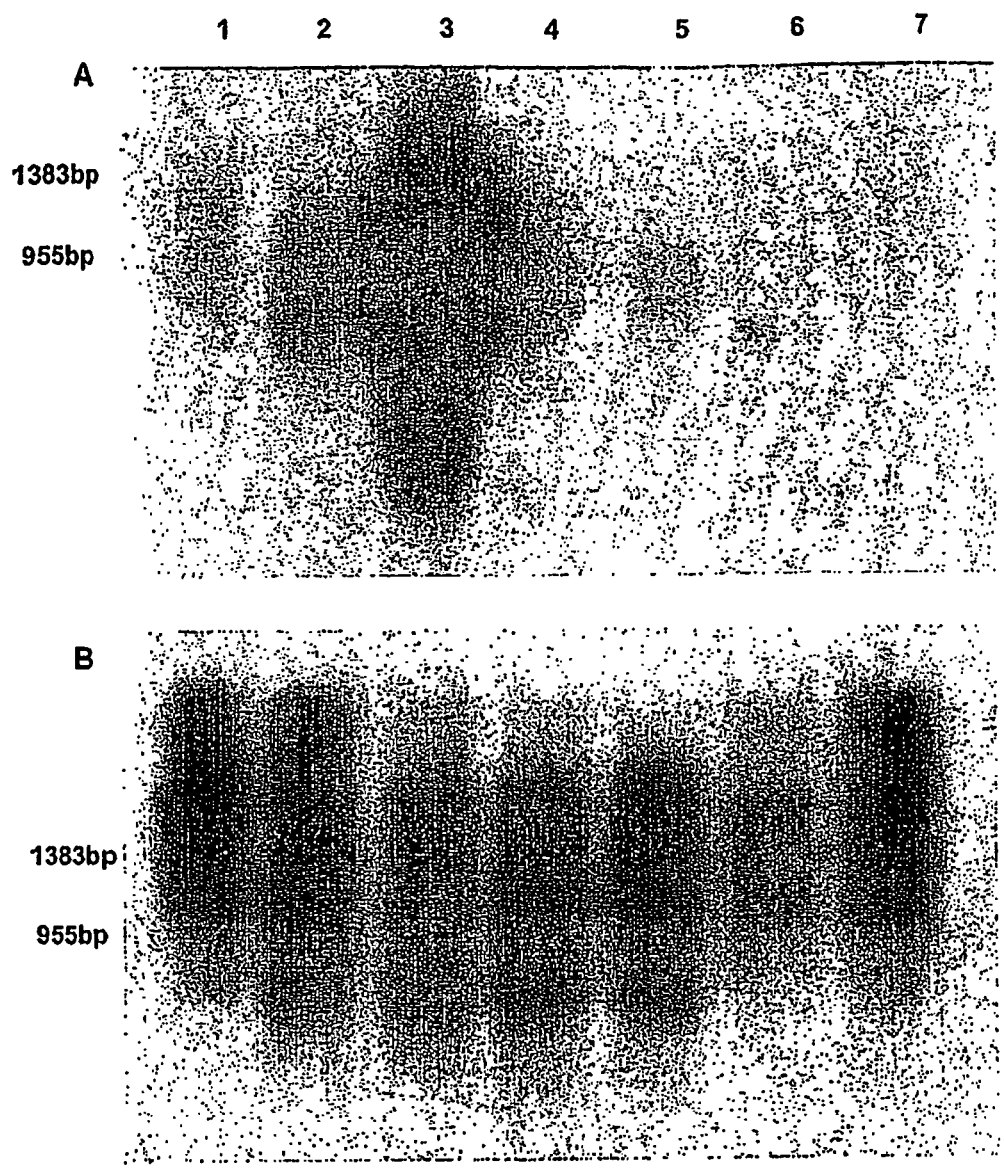
FIG. 25 shows a Northern blot analysis of B. napus tissues. Panel A shows the results of probing with the 484bp BnMYB103-1 gene specific probe. Panel B shows the results of probing with the ubiquitin probe.
Lane 1 dehiscing anthers
Lane 2 anthers from flower buds 2-6 mm
Lane 3 flower buds 0.5-2 mm
Lane 4 flower buds 2.5-5 mm
Lane 5 flower buds 6-8 mm
Lane 6 shoots
Lane 7 roots FIG. 26 RT PCR analysis of B. napus tissues. The top panel shows RT PCR products generated from B. napus tissues using primers specific to BnMYB103-1 (SEQ ID NO. 4), (a product of 979bp is expected). The bottom panel B shows RT PCR generated using primers specific to the β-8 tubulin gene (product of 545bp is expected).
Lane 1 molecular weight markers
Lane 2 dehiscing anthers
Lane 3 anthers from flower buds 2-6 mm
Lane 4 flower buds 0.5-2 mm
Lane 5 flower buds 2.5-5 mm
Lane 6 flower buds 6-8 mm
Lane 7 shoots
Lane 8 roots

A 474 bp BnMYB103-1 gene-specific probe was prepared from the 3' end of the sequence using PCR (96° C. 3 min×1, 96° C. 30 sec, 50° C. 30 sec, 72° C. 30 sec×30, 72° C. 5 min×1) using primers P16 and Z2346F02 (FIG. 24). To check for equal loading of polyA$^+$ RNA the filter was stripped and reprobed with a ubiquitin probe. The ubiquitin probe, a 1.2 kb fragment from the UBQ4 gene [Burke, (1988) Molecular and General Genetics 213: 435-443] was gel purified (Bresaclean kit, Geneworks) and labeled as described above. FIG. 25 shows the results of probing with both the gene-specific and ubiquitin probes. The strongest signal with the gene specific probe is found in flower buds 0.5-2 mm in length. A weaker signal is seen in pre-anthesis anthers. Probing with ubiquitin indicates that the loading of polyA$^+$ RNA for each sample was even.

Reverse Transcriptase Polymerase Chain Reaction for Detection of BnMYB103-1 mRNA RT PCR is another sensitive and specific method for the detection of mRNA. The total RNA samples used to prepare polyA$^+$ RNA for northern blotting were also used for RT PCR. The Onestep RT PCR kit (Gibco) was used to generate cDNA via reverse transcriptase and PCR was performed in the same tube.

Figure 26:
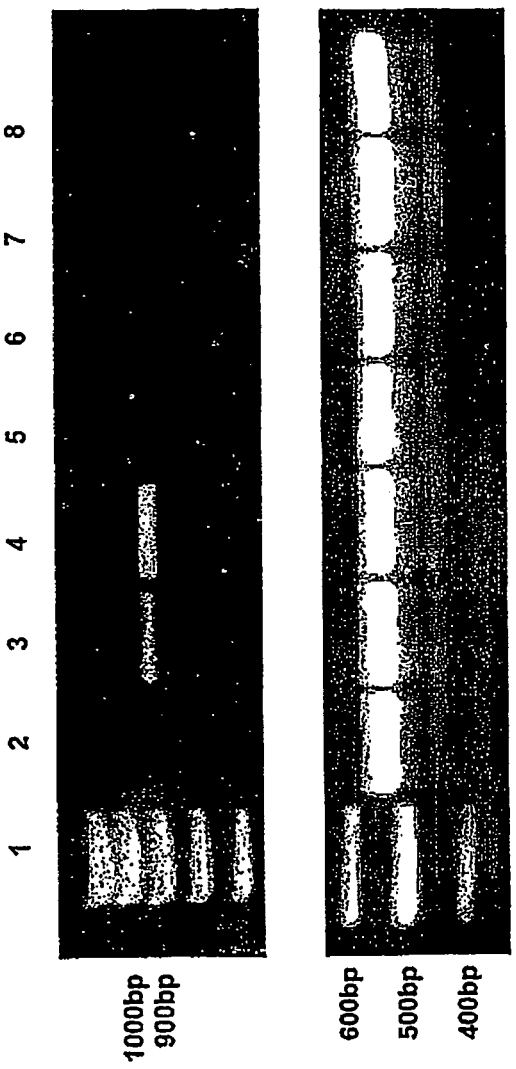
Figure 27:
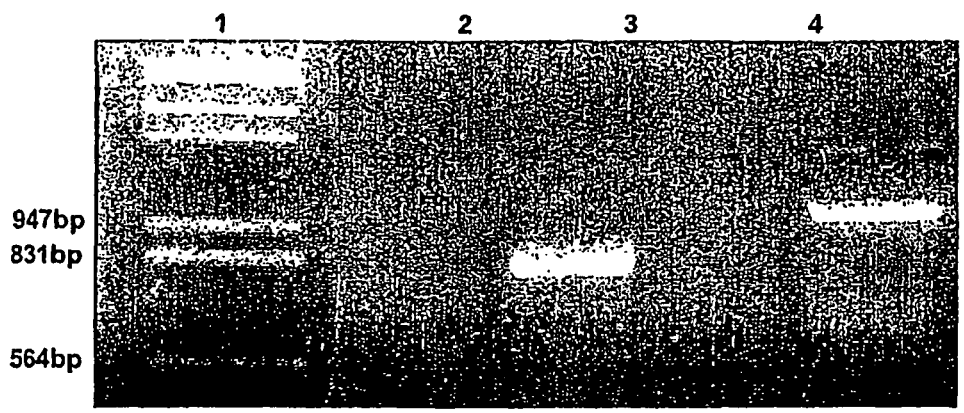
FIG. 27 shows RT PCR analysis of pre and post anthesis anthers for BnMYB103-1 mRNA.
Lane 1 molecular weight markers
Lane 2 post anthesis anthers, primers A5956A10 & A2485F504
Lane 3 pre anthesis anthers, primers A5956A10 & A2485F04
 These primers have amplified a 784bp fragment from B.napus cDNA.
Lane 4 post anthesis anthers, primers A5962H02 & Z1346E10
Lane 5 pre anthesis anthers, primers A5962H02 & Z1346E10
 These primers have amplified a 979bp fragment from B.napus cDNA.

Tubulin primers were initially used to assess whether RT PCR products could be obtained from the RNA samples (50° C. 30 min×1; 94° C. 2 min×1; 94° C. 30 sec, 45° C. 30 sec, 72° C. 60 sec×25; 72° C. 10 min×1). The primers were designed using the published sequence of *A. thaliana* β-8 tubulin [Snustad, 1992 The Plant Cell 4: 549-556]. A product of 545 bp is expected from cDNA using the tubulin primers. A product from contaminating genomic DNA would be 760 bp as the primers span two introns. All of the samples tested with tubulin primers produced a strongly amplified product of the correct size (FIG. 26). Two pairs of BnMYB103-1 specific primers were tested for their ability to produce a RT PCR product using RNA from pre- and post-anthesis anthers. The primer pairs employed were A5956A10 & A2485F04 and A5962H02 & Z1346E10 with fragments of 784 bp and 979 bp expected from cDNA respectively. RNA from pre-anthesis anthers gave a strongly amplified product of ~784 bp with primers A5956A10 & A2485F04 while primers A5962H02 & Z1346E10 generated a product of ~979 bp. No product was seen when RNA from post-anthesis anthers was used as template (FIG. 27).

The remaining RNA samples were then used as templates in RT PCR with primers A5962H02 & Z1346E10. Products corresponding to the size expected for BnMYB103-1 were only obtained from RNA isolated from pre-anthesis anthers and flower buds 0.5-2 mm in length (FIG. 26).

These RT PCR results agree with the Northern blotting data and BnMYB103-1 promoter-gusA experiments. Expression of BnMYB103-1 is restricted to pre-anthesis anthers and is most strongly expressed in flower buds 0.5-2 mm in length. At this stage of development the pollen exists as meiocytes, tetrads and newly released, pre-mitotic microspores and the tapetum shows its highest secretory activity.

b) BnMYB103-2

The second orthologue of AtMYB103 is named BnMYB103-2 and its nucleic acid sequence and putative amino acid sequence are provided in FIG. 2.

Example 3

Orthologues of the MB genes

BLAST searching of the GenBank database has identified putative orthologues of BnMYB32, namely GhMYB9 from cotton (FIG. 5*b*) TMH27 from tomato (FIG. 5*a*) and AtMYB32 from wheat (*Triticum aestivum*) (FIG. 36).

BLAST searching of the GenBank database has identified putative orthologues of BnMYB103-1, namely OsMYB103 from rice (FIG. 6 and FIG. 37). BLAST searching of the wheat Grain gene database (http://wheat.pw.usda.gov) identified a putative orthologue of AtMYB103 from wheat (*Triticum aestivum*) (FIG. 38).

The wheat and rice putative sequences were used to clone the orthologue genes.

The wheat orthologue TaMYB32 was cloned using RT-PCR with nested primers. The deduced amino acid sequence exhibits 63% identity to the AtMYB32 sequence (FIG. 36).

A homologous fragment of AtMYB103 from rice (*Oryza sativa*) anther cDNA was cloned using primers Tr-F1 and Tr-R2 (see FIG. 37). The fragment includes part of the R3 sequence and sequence immediately downstream from R3. The rice orthologue of AtMYB103, termed OsMYB13, exhibits a high level of sequence identity to AtMYB103 at the amino acid level.

FIG. 38 shows an alignment of the deduced amino acid sequences of AtMYB103 and a fragment of its wheat orthologue TaMYB103. Underlined amino acids are identical. The deduced amino acid sequence is about 90% identical to that of AtMYB103 sequence (FIG. 38).

Example 4

Functional Analysis of the MYB genes

Functional Analysis of BnMYB103-1

A number of strategies are available to obtain information about the function of a specific gene. The expression of BnMYB103-1 in immature anthers suggests a role in the development of the male reproductive structures. Homology with genes of known function may also provide some clue to function. BnMYB103-1 is highly homologous to the *A. thaliana* gene AtMYB103. As previously stated, AtMYB103 is expressed in the tapetum and developing microspores of *A. thaliana* at the stage where meiocytes are dividing meiotically to produce microspore tetrads [Li, 1999 supra]. The spatial and temporal expression patterns of AtMYB103 imply a function in the regulation of pollen development. An estimated 20,000 mRNA transcripts are present in the mature pollen of *Tradescantia paludosa* and maize, reflecting the complex nature of pollen development and presumably the requirement for regulatory genes.

Mutants also provide important information about gene function. Transposon mutagenesis can be used to disrupt a specific gene and function implied from any consequent phenotypic changes. Moreover, the gene can then be cloned and function verified using gene rescue. If the gene of interest is responsible for the mutant phenotype, the wild type phenotype will be regained. Mutagenesis has been used to generate a number of *A. thaliana* mutants that are defective in pollen development.

Antisense and sense techniques have been used in plants to disrupt the function of known genes. Many examples exist where a changed phenotype has been produced using this approach. Both techniques appear to silence expression of the endogenous gene being targeted. Post-transcriptional gene silencing (PTGS) has received significant attention in recent years and some of the mechanisms involved are now beginning to be understood.

The TA39 Promoter

Successful targeting of a specific endogenous gene using antisense and sense constructs requires a strong tissue specific promoter. The promoter from a pollen/anther specific gene of tobacco, TA39, was selected for this work. This promoter is expressed in the microspores, connective tissue and most highly in the tapetum during early pollen development [Goldberg, 1993 supra].

A TA39 promoter-gusA fusion (TA39::gusA) transformed into *A. thaliana* or *B. napus* drove strong GUS expression in the young anthers (FIG. 28). This expression pattern closely resembles that obtained with an AtMYB103 promoter fused to gusA [Li, 1999 supra]. AtMYB103 antisense and sense constructs driven by the AtMYB103 promoter had previously failed to produce a changed phenotype when transformed into *A. thaliana*. Hence, the TA39 promoter was selected for use with the BnMYB103-1 antisense and sense constructs.

Antisense and Sense BnMYB103-1 Constructs

Figure 29:
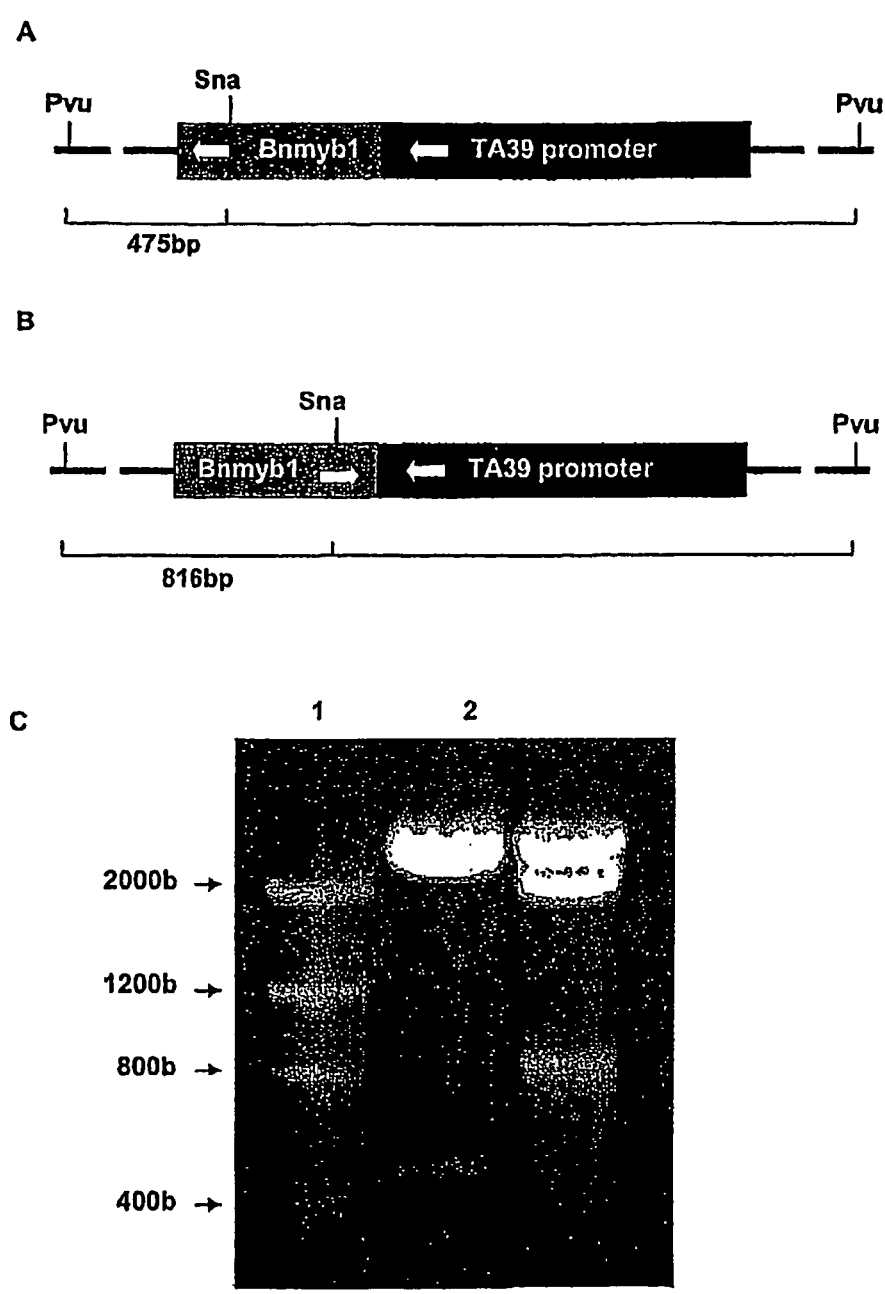
FIG. 29 shows restriction enzyme digest of BnMY103-1 (SEQ ID NO. 4) sense and antisense constructs.

The TA39 promoter was cloned as a 1.8 kb BamHI/SalI fragment from p4AI-LIT into pBluescript. An 800 bp fragment of BnMYB103-1, from the R3 repeat to the stop codon, was cloned as a BamHI fragment in front of the TA39 promoter. Restriction enzyme analysis (PvuII/SnaBI) identified constructs with the BnMYB103-1 fragment in both the sense and antisense orientation (FIG. 29). The 2.6 kb TA39::BnMYB103-1 SacI/SalI fragment from each of these constructs was cloned into the binary vector pBI101.2 for transfer into *A. thaliana* via root transformation (FIG. 30).

Characterisation of *A. Thaliana* Transgenics Transformed with Antisense and Sense BnMYB103-1 Constructs It has been predicted that the expression of antisense constructs to *Brassica* anther-specific mRNAs in *Arabidopsis* may produce informative mutants . . . and even suggest a function for the gene product. Transformation of *A. thaliana* and the generation of transformed plants for analysis can be accomplished in about two months. The same process in *B. napus* takes at least nine months. Taking these time frames into consideration, both *A. thaliana* and *B. napus* were transformed with the same constructs. Considering the high degree of homology between AtMYB103 and BnMYB103-1 it was felt likely that BnMYB103-1 antisense and sense constructs would interfere with the expression of AtMYB103 in *A. thaliana* plants.

Following root transformation and selection for transformed tissue, individual plants were grown for phenotypic analysis. The $T_0$ plants were analysed for presence of the transgene using PCR with primers specific to the antisense or sense construct, respectively (FIG. 31). Plants containing the transgene were then selected for further analysis. Pollen was taken from dehiscing flowers for analysis using the scanning electron microscope (SEM).

Table 1 summarizes the results of this analysis. The percentage of affected pollen ranges from <10% to 100% abnormal pollen. The abnormal pollen phenotype is variable with flattened, small, rounded or misshapen pollen resulting (FIGS. 32a & b). There appears to be no significant difference between the antisense and sense constructs with regard to the percentages of abnormal pollen or the phenotypes observed.

TABLE 1

Scanning electron microscope analysis of transgenic *A. thaliana* lines

| $T_o$ plants PCR positive for Antisense construct | | $T_o$ plants PCR positive for sense construct | |
|---|---|---|---|
| LINE | % ABNORMAL POLLEN | LINE | % ABNORMAL POLLEN |
| AS1 | 90 | S1 | 20 |
| AS2 | 80 | S2 | 20 |
| AS3 | 90 | S3 | 90 |
| AS4 | 90 | S4 | 80 |
| AS5 | 90 | S5 | 10 |
| AS6 | 30 | S6 | 80 |
| AS7 | 90 | S7 | 50 |
| AS8 | 20 | S8 | 50 |
| AS9 | 30 | S9 | 40 |
| AS10 | 100 | S10 | 30 |
| AS11 | 90 | S11 | 90 |
| AS12 | <10 | S12 | 40 |
| AS13 | 10 | S13 | 50 |
| AS14 | 10 | S14 | 10 |
| AS15 | 90 | S15 | 60 |
| AS16 | 90 | S16 | 10 |
| AS17 | 10 | S17 | 50 |
| AS18 | 20 | S18 | 30 |
| AS19 | 100 | S19 | 90 |
| AS20 | 30 | S20 | 100 |
| AS21 | 40 | S21 | 40 |
| AS22 | 80 | S22 | 90 |

TABLE 1-continued

Scanning electron microscope analysis of transgenic *A. thaliana* lines

| T$_o$ plants PCR positive for Antisense construct | | T$_o$ plants PCR positive for sense construct | |
|---|---|---|---|
| LINE | % ABNORMAL POLLEN | LINE | % ABNORMAL POLLEN |
| AS23 | 30 | | |
| AS24 | 90 | | |
| AS25 | 60 | | |
| AS26 | 100 | | |
| AS27 | 50 | | |
| AS28 | 70 | | |
| AS29 | 90 | | |

All lines, no matter how severely the pollen phenotype was affected were able to produce viable seed. T$_1$ plants from selected lines were raised to determine whether the pollen phenotype observed in T$_0$ plants would be carried over into the next generation. Five of the most severely affected plants from each of the construct types were chosen. In each case the abnormal pollen phenotypes were maintained in the T$_1$ generation. PCR analysis of these plants confirmed the presence of the relevant transgene.

Characterisation of *B. Napus* Transgenics Transformed with Antisense and Sense BnMYB103-1 Constructs Transformation of *B. napus* with the antisense and sense constructs was carried out and viability of transgenic pollen ascertained. All of the PCR positive transgenic plants contained viable pollen as determined by iodine staining. Scanning electron microscope analysis of pollen from these plants showed no significant abnormalities (results not shown). All of the transgenic lines produced viable seed.

Crossing of Antisense and Sense Lines

Waterhouse et al. (1998) PNAS 95:13959-13964 showed that transgenic tobacco transformed with both sense and antisense forms of the protease (Pro) gene from potato virus Y displayed greater levels of immunity to the virus than plants transformed with one or other of the constructs.

In an attempt to obtain a male sterile phenotype, antisense and sense lines from *B. napus* or *A. thaliana* and were crossed to obtain transgenic plants of each species carrying both transgenes. Plants shown to be PCR positive for either the sense or antisense transgene were selected for use as both male donors and female recipients. The pre-dehiscent anthers from newly opened flowers were removed and the stigma inspected for the presence of pollen. A dehiscing anther from the male donor was then used to deposit pollen directly onto the stigmatic surface. Treated flowers were tagged with the relevant information and siliques allowed to develop. Seed from these siliques was germinated on selective media, GM kanamycin (50 µg/ml) for *A. thaliana*, GM hygromycin (100 µg/ml) for *B. napus*. Seedlings able to grow on these media were transferred to soil and grown to maturity. The presence of both transgenes was confirmed with PCR using primers specific to each construct. Lines raised from each of these crosses were analysed for abnormal pollen phenotypes using the SEM.

All of the *A. thaliana* lines showed abnormal pollen similar to that observed in the antisense or sense parents. All of the plants produced viable seed, indicating that complete male sterility had not been achieved. The *B. napus* lines showed a range of phenotypes with up to 90% abnormal pollen, a feature not observed in either of the antisense or sense parents. Some of the plants generated from these crosses were PCR positive for only one of the transgenes, indicating a degree of self-fertalisation. As these plants represent a T$_1$ population and may be homozygous for the transgene it was of interest to analyse their pollen. Some of these T$_1$ plants did show abnormal pollen phenotypes similar to those seen in *A. thaliana*. SEM analysis of these transgenic plants showed that the plants were able to produce viable seed.

Pollen Phenotypes

Wild type *A. thaliana* and *B. napus* pollen both appear very similar, apart from an obvious size difference. An *A. thaliana* WT pollen grain is approximately 30×15 µm and a *B. napus* pollen grain approximately 40×20 µm. Both are tricolpate with germinal apertures that run the length of the grain and are positioned equidistantly. The exine has a characteristic network of ridges that form a regular pattern. Using the SEM a range of abnormal pollen phenotypes was observed in *A. thaliana* transformed with the sense, antisense or both constructs. Similar phenotypes are observed in T$_1$ sense and antisense *B. napus* plants or when both constructs are present. The abnormalities can be divided into a number of categories: 1. Pollen exhibiting normal exine patterning but displaying abnormalities in shape, size and germinal aperture positioning; 2. Aborted pollen that appears small and deflated but with normal exine patterning; 3. Abnormally shaped grains that appear partially or fully deflated with normal exine patterning but coated in parts as if the contents have "oozed" out. In some cases, pollen displaying this phenotype occurred in large clumps, apparently held together by the secreted contents; and 4. Pollen that is small and rounded.

In many cases the abnormal pollen from BnMYB103-1 sense and antisense transgenic *A. thaliana* and *B. napus* plants are larger than wild type. Abnormally large pollen from *A. thaliana* showed an average increase of 15% in length and 30% in diameter. The largest increases observed were 26% in length and 46% in diameter. In *B. napus* the average increases were 5% in length and 13% in diameter. The largest increases observed were 10% in length and 30% in diameter.

Transmission electron microscope analysis of abnormal pollen Abnormal pollen grains from a number of *A. thaliana* lines transgenic for either the sense or antisense BnMYB103-1 transgene were selected for analysis using the transmission electron microscope (TEM). Thin sections through these pollen grains were compared with sections of wild type pollen at the same developmental stage. The exine, intine, middle layer, tapetum and microspores of pollen from the transgenics all appear normal. No obvious differences can be detected in these sections.

Example 5

Production of Male Sterile Plants

From Example 4 it is shown, that at least in *B. napus*, blocking expression of BnMYB103 alone does not produce 100% sterile plants. The inventors propose that at least two and preferably three genes need to be blocked in *B. napus* to produce 100% male sterile plants.

In an attempt to provide 100% male sterile plants in *B. napus* the following construct containing a glucocorticoid (dexamethasone)-mediated transcriptional induction system was made. The strong TA39 promoter was incorporated in the system to ensure an adequate level of GVG is produced in developing anthers. Once activated by dexamethasone (DEX) GVG can induce the transcription from the chimeric promoter. A GUS reporter gene was placed under the control of the chimeric promoter to examine the effectiveness of the system.

Exact details of the construct are as follows, with reference to FIGS. 33 *a* & *b* and FIG. 34:

The BamHI-digested BnMYB103-1 fragment was blunt-ended and inserted into the EcoRV site of the plasmid containing BnMYB103-2 sequence. The BamHI AtMYB32 fragment was then ligated to the BamHI site of the resultant plasmid pBnMYB103-12 creating pMYB103-32 (all sequences in the same orientation) and pMYB103-23 (At-MYB32 in opposite orientation). The Xho1-Xba1 fragments from the two plasmids were cloned into the Xho1-Xba1 sites of pLITMUS28 (New England Biolab) producing pLTMYB103-32 and pLTMYB103-23, respectively. The MYB fragments were then released from pLTMYB103-32 and pLTMYB103-23 using Spe1 restriction enzyme and inserted into the Spe1 site of pTADEX1 generating pTADEX31 and pTADEX32, pTADEX71 and pTADEX72, respectively. Plasmid pTADEX1 was constructed by replacing the Sbf1-Pme1 CaMV35S fragment in pTA7002 (Nam-Hai Chua, Rockefeller University USA) with a Pst1-EcoRV TA39 promoter fragment. The numbers marking the ends of the MYB fragments indicate the number of base pairs downstream from the translational start site (ATG). AtMYB32 sequence includes a translational start site at position 1 and a stop codon at position 822. Boxes represent promoters.

GVG encodes a chimeric transcription factor which binds to and activates the 6UAS promoter in the presence of dexamethazone. HPT gene encodes hygromycine phosphotransferase used for the selection of transgenic plants.

The system was introduced into *Arabidopsis* plants and the GUS expression of four lines was examined. The GUS activity was detected only in the anthers sprayed with DEX (FIG. 35B). Two allelic sequences of BnMYB103, BnMYB103-1 and BnMYB103-2 and one copy of AtMYB32 sequence were linked together in a sense or antisense orientation. These fragments containing multiple MYB sequences were placed under the control of the chimeric promoter. The constructs were transformed into *Arabidopsis* plants and PCR analysis was used to ascertain the presence of the transgenes in the plants.

The seed setting of 25 transgenic lines was examined in repsonse to the DEX spray and eight of these lines exhibited abnormality in seed setting. The majority of the siliques (50-95%) in these lines failed to elongate (aborted (FIG. 35H) and the elongated siliques contained fewer seeds than the untreated siliques. These transgenic lines produced abnormal pollen in response to DEX induction (FIG. 35F). Most of these abnormal pollen are devoid of contents as demonstrated by Alexander staining and the presence of aggregates inside the pollen sacs (FIG. 35D). However, the gynoecia of the male sterile flowers remained fertile as cross-pollination with untreated pollen restored the seed setting.

Example 6

A Repressor/Restorer Male Sterility System

Transcription repressors use various repressive motifs to block the transcription of their target genes. One of the plant repressive motifs consists of about twelve amino acids (LDLDLELRLGFA (SEQ ID NO: 27), or LDLNLELRISPP (SEQ ID NO 28)). The two peptide sequences exhibit nine identical or homologous residues. The repressive motif (LDLDLELRLGFA) (SEQ ID NO: 27) from Arabidopsis was fused to four different transcription factors with resultant loss-of-function phenotypes demonstrating that the motif converts transcription factors into strong dominant repressors. Inspection of AtMYB7 (Li, S.F., Parish, R.W. (1995) Plant J. 8, 963) and AtMYB32 C-terminal sequences identified the repressive sequence (LDLNLELRISPP) (SEQ ID NO: 28).

Figure 44:
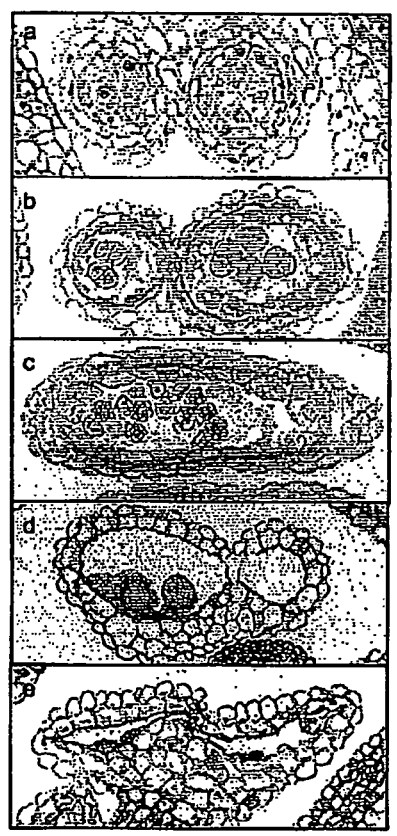

The strategy is to convert AtMYB103 into a strong repressor using the motif of twelve amino acids to obtain male sterility. The heterozygous male sterile inbred A containing the chimeric AtMYB103 repressor (AtMYB103Rep) is crossed with inbred B containing a "restorer" to produce male fertile F1 hybrid seeds (FIG. 44). The "restorer" will be AtMYB103 gene under the control of the strong anther-specific At39 promoter or multiple copy of the AtMYB103 promoter or their equivalents. Higher levels of the AtMYB103 protein (activator) in the hybrid plants will alleviate the repression by AtMYB103Rep protein leading to viable pollen production and seed setting.

The system produces 50% male fertile inbred A seedlings. A selectable marker linked to the repressor will provide a selection to cull the male fertile inbred A seedlings before crossing with inbred B. Alternatively, a simple chemical which can overcome the repression by the AtMYB103Rep may be used to induce seed setting of the male sterile plants to obtain the homozygous inbred A seed. The homozygous and male sterile inbred A plants will then be crossed with inbred B plants to obtain F1 hybrid seed.

The repressor/restorer reversible male sterility system is being successfully tested in *Arabidopsis* and is suitable for hybrid seed production in any crop plants including canola and wheat.

A sequence coding for the repressor motif of twelve amino acids, LDLDLELRLGFA, was fused in frame to the 3' end of the AtMYB103 coding sequence producing a chimeric fusion peptide. The chimeric gene was placed under the control of the AtMYB103 promoter (FIG. 39). The repressor construct was transformed into *Arabidopsis* plants and more than 50% of the sixty transformants exhibited male sterility. A restorer (activator) containing the AtMYB103 gene under the control of the At39 promoter was constructed (FIG. 39). Eight *Arabidopsis* lines transgenic for the restorer were obtained and exhibited normal male fertility. Pollen from these restorer plants was used to pollinate some male sterile plants containing the repressor construct and the F1 hybrid seeds were collected for further analysis.

Example 7

Further Studies on the Repressor/Restorer Male Sterility System

In this experiment, an AtMYB103 insertion mutant is described, which exhibits complete male sterility with early tapetum degeneration and collapsed pollen. Loss-of-function mutant plants were also obtained using an AtMYB103/EAR chimeric repressor. The plants are male sterile and the effects on tapetum and pollen development are similar to those observed in the insertion mutant. A restorer containing the AtMYB103 gene driven by a strong anther specific promoter was able to restore male fertility when introduced into the male sterile plants. The chimeric repressor and the restorer constitute a reversible male sterility system which can be adapted for hybrid seed production. This is the first reversible male sterility system targeting a transcription factor essential to pollen development.

Experimental Procedures

Plant Materials and Growth

*Arabidopsis thaliana* accession Columbia (Col-0) was used for all gene transfer experiments and wild-type controls. Plants were grown on soil under constant illumination or on germination media (GM) containing the appropriate selective antibiotic. The atmyb103 T-DNA insertion mutant line (line 320C12) was obtained from GABI-Kat (Max Planck Institute for Plant Breeding Research, Germany; http://www.gabi-kat.de). Seed was sown on GM containing 11.25 μg ml$^{-1}$ Sulfadiazine to select for plants containing the T-DNA insert. Surviving plants were screened by PCR using the primers 103-52For and pAC161Rev (Table 2) to confirm the T-DNA insertion in AtMYB103 gene. The primers 103-52For and 103+1474Rev which flank the T-DNA insert, were used in PCR reactions to determine the genotype of selection positive plants.

Plasmid Construction

The full-length AtMYB103 cDNA was amplified from Arabidopsis wild-type cDNA using the primers 103-3For and 103+1476Rev. The fragment was cloned into the pDrive vector (Qiagen) and sequenced. The fragment was excised from pDrive and inserted into the Sma1 and Sac1 restrictions sites of the pBIAt39 vector. pBIAt39 contains a 1300 bp At39 promoter cloned into the HindIII and BamH1 sites of the pBI101.2 vector (Clontech). The resultant plasmid pP39/103 encodes an AtMYB103 protein fussed with the first 8 amino acids of At39. To construct plasmids pP103/103EAR and pP39/103EAR, a P103/103EAR fragment was amplified from Arabidopsis (Col) genomic DNA using PCR with primers EAR103F and EAR103R. The EAR103R contains a sequence coding for the EAR motif fused in frame with the AtMYB103 sequence. The PCR fragment was cloned into plasmid pDrive and sequenced. The P39/103EAR fragment was amplified from the plasmid pP39/103 using PCR with primers At39-1260 and EAR103R. The PCR fragment was then cloned into the pDrive and sequenced. The SalI-HindIII fragments of P103/103EAR and P39/103EAR were then ligated to SalI-HindIII sites of plasmid pCAMBIA1380 (CAMBIA, http://www.cambia.org), respectively.

Plant Transformations

Constructs were transformed into Agrobacterium tumefaciens strain GV3101. Arabidopsis thaliana (accession Col-0) was transformed by vacuum infiltration following the method described by Bechtold et al (1993) C.R. Acad. Sci. Paris, Life Sciences, 316, 1194-1199. T$_0$ seed was sown on GM containing 50 μg ml$^{-1}$ kanamycin sulphate (pP39/103) or 15 μg ml$^{-1}$ and hygromycin (pP103EAR, pP39/EAR) grown under constant light at 22° C. Surviving transformants were verified by PCR amplification of the transgenes from genomic DNA using construct-specific primers.

RT-PCR Analysis

Total RNA used in the RT-PCR experiments was isolated from young florets of soil-grown plants using Trizol Reagent (Invitrogen Inc., FIGS. 1 and 8) or RNeasy plant kit (Qiagen, FIG. 6). First strand cDNA synthesis was carried out according to the manufacturer instructions (Invitrogen: Superscript™ III reverse transcriptase and reagents). The conditions for PCR amplification of cDNA were as follows: first cycle, 94° C. for 3 min; second cycle, 94° C. for 30 sec, 55° C. for 30 sec and 72° C. for 50 sec; third cycle, 72° C. for 10 min. For the PCR reactions in FIGS. 6a and b, the annealing reaction was set at 48° C. for 30 sec. Gene-specific primers were used for the amplifications of β-tubulin (TUB1, TUB2), AtMYB103 (103-137For and 103+1004Rev for FIG. 1, 103-52For and 103+1004Rev for FIG. 8, 103F5 and 103UTR for FIG. 6), P39/103 (At39+4For, 103-1004Rev), P103/103EAR (103F5, EAR-RT). PCR products were visualized by running on a 1.2% agarose gel stained with ethidium bromide and captured digitally using a UV video capture system. For non-reverse transcribed controls, the Superscript enzyme was omitted from first strand cDNA synthesis.

Floral Sectioning

Whole florets at varying stages of development were fixed in 6% glutaraldehyde and 4% paraformaldehyde in 50 mM sodium phosphate buffer for 2 h at 4° C. following 2-15 min of vacuum infiltration. Fixed tissue was dehydrated using the following ethanol series: 30, 60, 70, 90 and 100% followed by infiltration in LR white/ethanol. Florets were embedded overnight at 65° C. and sectioned using a Reichert ultramicrotome. Sections (2.0 μm) were stained with 0.25% safranin. Anther stages were classified according to Sanders et al. (1999) supra.

Microscopy

The morphology of pollen grains from mature, soil-grown plants was examined using a JOEL JSM 6340F field emission scanning electron microscope (Tokyo, Japan). Mature pollen grains were examined at ambient temperature. Images were digitally captured at a working distance of 28 mm at 2.0 kV. Analysis of anther sections using transmission electron microscopy was carried out as described previously (Higginson et al., 2003 supra). Digital images were processed using ADOBE Photoshop version 5.5 and Microsoft Power Point and Office 2000.

Results

Male sterility of an AtMYB103 Insertion Mutant

Figure 41:
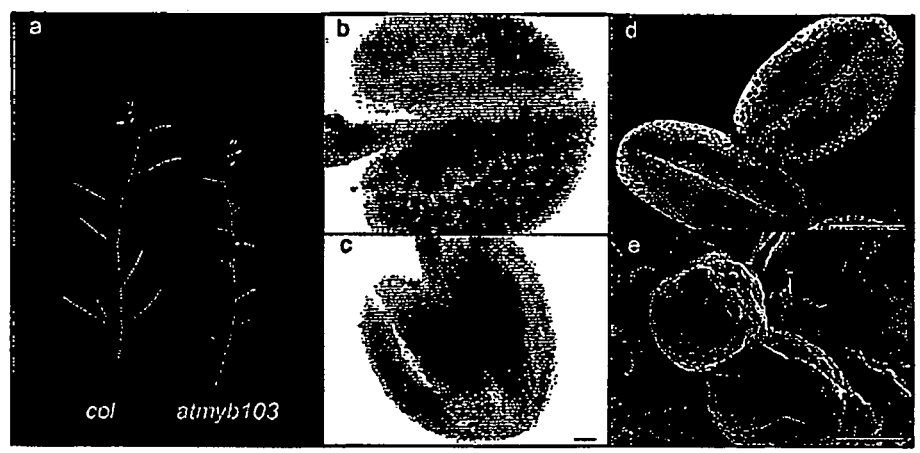

An AtMYB103 insertion mutant line was obtained from the Max Planck Institute for Plant Breeding Research, Germany. The T-DNA insertion was identified in the 3' coding region of AtMYB103 gene approximately 54 bp upstream of the translational stop codon. The insertion creates a truncated protein with an 18 amino acid deletion from its C-terminal (FIGS. 40A and B) and with the addition of an extra 36 amino acids encoded by the T-DNA sequence (FIG. 40B). Sulfadiazine resistant plants were obtained with a 3:1 segregation ratio and homozygous plants identified using PCR analysis. The AtMYB103 mutant was found to be recessive. The insertion drastically reduced the level of truncated AtMYB103 transcript in the mutant, as shown by the lower level of RT-PCR product from the mutant flowers (FIG. 40C). The homozygous plants displayed complete male sterility and produced collapsed pollen grains with little cytoplasmic content (FIGS. 41b and c). These pollen grains formed aggregates and could not be released from the anther locules. A few remaining pollen grains possessed abnormal pollen walls (FIGS. 41d and e). The siliques failed to elongate (FIG. 41a). The seed setting and silique elongation were restored using donor pollen from wild-type plants indicating that the gynoecium remained fertile in the insertion mutant. The male fertility of the insertion mutant was restored by a complementing construct containing the AtMYB103 gene (data not shown). The male sterile plants produced longer inflorescences, more flowers and exhibited an extended flowering time.

The development of tapetum and pollen in the wild-type and mutant plants was examined in anther sections (FIG. 42). Florets from the wild-type and mutants plants were fixed, embedded, sectioned and analysed. The tapetum and pollen in the mutant appeared normal and indistinguishable from wild-type anthers up to stage 5 (FIGS. 42a and b). In wild-type anthers at stage 6, pollen mother cells entered meiosis and tapetal cells became vacuolated (FIG. 42c; Sanders et al., 1999 supra). The mutant tapetum at stage 6 appeared slightly more vacuolated (FIG. 42d) and this abnormality became more severe at stage 7 (FIGS. 42e and f), when pollen mother cell meiosis had been completed and tetrads formed. In the wild-type anthers, the callose wall surrounding the tetrads dissolved at stage 8 releasing microspores (FIG. 42g) and tapetum degeneration initiated at stage 10 (Senders et al., 1999 supra). However, some tetrads in the mutant failed to separate (FIG. 42h) even though the callose surrounding the tetrads appeared to have been lost. The mutant tapetum exhibited an advanced stage of degeneration at stage 9 (FIGS. 42i and j). At stage 12, most microspores in the mutant anther locules were collapsed and a few microspores containing cytoplasm were trapped among the debris (FIG. 42k, l and m).

The ultrastructure of the tapetum was further examined using transmission electron microscopy. The mutant tapetum was more vacuolated than wild-type tapetum and pollen mother cells appeared normal at stage 6 (FIG. 42n and o). The tapetum vacuolation became more pronounced at tetrad stage and tapetum degeneration clearly visible at about stage 9 (FIGS. 42p and q). By this stage, cellular debris was observed in the anther locules and no exine was deposited on the pollen wall (FIG. 42q). These results indicate that disruption of the AtMYB103 gene leads to earlier tapetum degeneration and completely disrupts pollen development. The phenotype effects resemble those obtained using antisense technology (Higginson et al., 2003 supra) but are more severe.

Male Sterility Induced by a Chimeric AtMYB103 Repressor

In order to regulate male sterility by interfering with AtMYB103 function, the possibility of creating a dominant AtMYB103 repressor was explored. The twelve amino acid EAR sequence has been shown to act as a dominant repression motif when fused with other transcription factors (Hiratsu et al., 2003 supra). A short nucleotide sequence coding for the EAR sequence was fused in frame to the 3' end of the AtMYB103 open reading frame, generating an AtMYB103EAR fusion. The last amino acid (valine) in the AtMYB103 peptide was replaced by a glycine at the fusion joint (FIG. 43A). The fusion construct was placed under the control of either the AtMYB103 promoter (pP103/103EAR) or a strong anther specific promoter At39 (At5g59845) (pP39/103EAR) (FIG. 43A), respectively. The At39 promoter is strongly expressed in developing Arabidopsis anthers with highest expression in the tapetum (unpublished results).

Arabidopsis plant lines transgenic for the constructs (about 60 lines per construct) were examined for pollen formation and seed setting. Approximately sixty percent of the pP103/103EAR lines exhibited complete male sterility and silique abortion (FIG. 43B, a and b), but only five percent of the pP39/103EAR lines did so. The At39 promoter was much less efficient in inducing male sterility than the AtMYB103 promoter, presumably because it is activated slightly later in anther development than the latter promoter. The male sterility phenotype was stable through two to three generations in nine lines tested and segregated with the transgene. The pollen grains from the male sterile lines exhibited a range of morphologies, from partially to completely collapsed. The great majority of pollen grains in some of the male sterile lines were completely collapsed and devoid of cellular contents (FIG. 43B, c and d).

Flower buds from the pP103/103EAR plants were sectioned and the anther sections (FIG. 44) were compared with wild-type (FIG. 42a, e, i and k). In the early stages of anther development, both the tapetum and microspore mother cells appeared normal (FIG. 44a). The mutant tapetum at stage 7 (tetrad stage) became more vacuolated and appeared to initiate its degeneration (FIG. 44b) much earlier than the wild-type tapetum. The sporocytes had undergone callose deposition and completed meiosis to form tetrads. At stage 9, the callose surrounding the tetrads appeared to dissolve but some of the microspores were attached to each other (FIG. 44c) indicating that some callose remained. Most of microspores eventually degenerated and their remnants formed aggregates adhered to anther locule walls (FIGS. 44d and e). A few microspores contained some cytoplasmic contents and were trapped among the remnants. Hence, addition of the EAR sequence to the AtMYB103 protein results in anther and pollen phenotype similar to that obtained with the insertion mutant.

The transcript levels of the P103/103EAR transgene and the endogenous AtMYB103 gene were determined in the developing flowers of five male sterile lines using RT-PCR analysis (FIG. 45). The RT-PCR product levels of the endogenous AtMYB103 transcript in the transgenic lines are similar to those found in wild-type plants (FIG. 45a, lanes 1-10). The transgene RT-PCR product levels are also similar between lines (FIG. 45b, lanes 1-10) but are somewhat higher than the levels of AtMYB103 product (FIGS. 45a and b). The β-tubulin product levels were included to indicate similar amounts of total RNA in the RT-PCR reactions (FIG. 45c, lanes 1-10). Hence, addition of the EAR motif was highly effective in converting the MYB transcription factor to a dominant repressor. Furthermore, the weak MYB promoter drove sufficient levels of expression to repress the activity of endogenous AtMYB103.

The repressor/restorer system for hybrid seed production
The possibility of utilizing the P103/103EAR transgene in a repressor/restorer male sterility system was then determined. A repressor/restorer system requires a male sterility-inducing repressor incorporated into female lines (pollen recipients) and a restorer in male lines (pollen donors) (FIG. 46). In this case, the restorer would consist of the AtMYB103 gene under the control of a strong anther specific promoter such as the At39 promoter (pP39/103). We postulated that in the F1 plants derived from the cross, the high levels of the AtMYB103 protein would prevent the AtMYB103EAR fusion protein from repressing pollen production and male fertility be restored.

Several Arabidopsis lines transgenic for the restorer (P39/103) were obtained and all exhibited normal growth and seed setting. Analysis of the anthers and pollen grains revealed no abnormality (data not shown). The transcript levels of the transgene and endogenous AtMYB103 gene were examined in the developing florets of four lines using RT-PCR analysis. The RT-PCR product levels of the transgene P39/103 were much higher than those of the endogenous AtMYB103 gene in all four lines (FIG. 47c, d and a, b). The β-tubulin product levels of the four RNA samples were similar (FIGS. 47g and h, lanes 1, 2, 3, 4). The primers for the restorer RT-PCR were also used to amplify any genomic restorer DNA present in the RNA samples and lower levels of the genomic products were detected (FIG. 47e and f).

Pollen grains from four pP39/103 lines were used to fertilize seven male sterile pP103/103EAR lines, including the four lines shown in FIG. 45. The F1 plants were isolated in double selection media for both the repressor and restorer constructs. The F1 plants from thirteen crosses were examined for silique elongation. The silique elongation was completely restored in one F1 line. Normal elongation of about seventy percent of siliques was observed in two F1 lines and about thirty percent in one line. The phenotype of silique elongation in F1 plants segregated with the restorer construct. The variability in restoration of male fertility probably relates to the stages of anther development when the At39 promoter is active (see Discussion).

Discussion

AtMYB103 Controls Tapetum and Microspore Development.

As previously reported (Higginson et al., 2003 supra), down-regulation of AtMYB103 expression in flowers led to earlier tapetum degeneration and the formation of distorted pollen with reduced or no cytoplasmic content. However, these plants were able to set seed so viable pollen was produced for self-fertilisation to occur. In this experiment, a complete loss-of-function phenotype for AtMYB103 was obtained with both an AtMYB103 insertion mutant and mutant plants transgenic for an AtMYB103/EAR chimeric repressor. The mutant plants generated using the two different approaches exhibited complete male sterility and similar developmental abnormalities of tapetum and pollen. The tapetum became highly vacuolated and degenerated prematurely. Microspores in many tetrads failed to separate at later stages and exine was not deposited in the pollen wall.

Almost all microspores collapsed and degenerated. These results indicate that premature tapetum degeneration reduces the enzymes responsible for callose degradation and prevents exine formation by limiting either the production or deposition of exine components. The absence of exine and the limited availability of other essential molecules for pollen development lead to pollen degeneration. The results indicate the AtMYB103 gene is required for the maintenance of the tapetum during early microspore development, prior to the initiation of tapetum degeneration at stage 10. The AtMYB103 protein is most probably a transcription activator (see below) and may activate specific pathway(s) holding the tapetum degeneration process in check during the early stages of pollen development. Disruption of the pathway(s) allows programmed cell death to proceed.

AtMYB103 transcript was detected in trichomes using in situ hybridization and down-regulation of AtMYB103 expression resulted in overbranched trichomes containing more nuclear DNA in *Arabidopsis* (Landsberg erecta) (Higginson et al., 2003 supra). However, no visible change of trichome morphology was detected in the insertion mutant (Columbia). This variation may be related to the differences between the two *Arabidopsis* ecotypes.

It was proposed that the AtMYB103 gene might control similar processes in trichomes and tapetal cells, such as endoreduplication (DNA replication without cell division) in trichomes and polyploidization (cell divisions without cytokinesis) in tapetal cells (Higginson et al., 2003 supra). Hence the anther transcript levels of some of the genes required for cell cycle regulation were compared in anthers of wild-type plants and the insertion mutant. These genes code for a cyclin (CYCD3), cyclin-dependent kinases (CDKA, CDKB1 and CDKB2), CDK inhibitors (KRP1 and KRP2) and histone H4. RNA samples were extracted from the wild-type and mutant anthers of stages 5 to 9, respectively, before the initiation of microspore mitosis at stage 11 and RT-PCR analysis carried out with gene specific primers. The RT-PCR product levels of these genes in the mutant anthers were similar to those in the wild-type anthers (data not shown) indicating that the expression of these genes is not directly controlled by the AtMYB103 gene. While comparative microarray analysis using the wild-type and atmyb103 mutant anthers may identify large numbers of genes which are down-regulated, as is the case in the rice udt1 mutant, most of these genes are not the direct targets of the transcription factor and their down-regulation a consequence of the premature disappearance of tapetal tissue. An inducible complementary system would be more appropriate for the identification of target genes.

Mutations in several genes coding for transcription factors have been found to cause premature tapetum degeneration and pollen abortion. These genes include the rice UNDEVELOPED TAPETUM 1 (UDT1) coding for a basic helix-loop-helix protein, *Arabidopsis* MALE STERILITY 1 (MS1) coding for a PHD-finger transcription factor and ABORTED MICROSPORES (AMS) encoding for a basic helix-loop-helix protein. The UDT1 protein shares 32% identity with the AMS protein. Silencing of the petunia TAPETUM DEVELOPMENT ZINC FINGER PROTEIN 1 (TAZ1) gene also leads to early degeneration of tapetum and pollen abortion. The tapetum in a atmyb33 and atmyb65 double mutant undergoes hypertrophy at the pollen mother cell stage resulting in partial male sterility. However, the fertility was restored under higher light intensity or at a lower growth temperature indicating that the two genes are not essential for tapetum development.

The Chimeric Repressor

Several chimeric repressors driven by the CaMV35S promoter have been successfully used to induce loss-of-function phenotypes. This experiment represents the first example of a chimeric repressor under the control of its native promoter that induces a loss-of-function phenotype. The P103/103EAR transgene was highly efficient in inducing male sterility, indicating that the levels of chimeric repressor transcript required for effective repression are relatively low and comparable to levels of the endogenous AtMYB103 transcript (FIG. 45). As the AtMYB103 promoter is active only in early tapetum development, it may well be used to express other chimeric repressors to obtain male sterility.

The AtMYB103 protein was converted into a dominant negative repressor, implying it normally functions as a transcription activator or it interacts with an activator. Transcription activation domains are classified into three groups, namely acidic, proline-rich and glutamine-rich. Inspection of the sequence outside of the MYB domain identified an acidic sequence of twenty-six amino acids at the C-terminus (256-282aa) with ten negatively charged and four positively charged amino acids. This putative activating domain may be repressed by the EAR motif in the chimeric repressor. However, it is unclear how the EAR motif exerts its repression effect. The repression efficiency of the EAR motif was recently further demonstrated. Four genes coding for *Arabidopsis* transcription factors, namely APETALA3, AGAMOUS, LEAFY and AtMYB26, were fused with the EAR sequence and each driven by the CaMV35S promoter. Transgenic plants expressing the chimeric repressor exhibited a phenotype similar to the loss-of-function phenotype of the corresponding gene.

The Restorer and Reversible Male Sterility Systems

To construct a reversible male sterility system using the pP103/103EAR chimeric repressor, an effective restorer is required to restore male fertility to the F1 plants. The AtMYB103 gene under the control of a suitable anther specific promoter can act as a restorer. A proof of concept for the system was obtained using the strong anther specific promoter At39 to drive expression of the AtMYB103 gene. The pP39/103 construct was able to restore male fertility in some lines. Multiple copies of the AtMYB103 gene driven by its own promoter (AtMYB103 genomic clone) may prove to be a more effective restorer. Alternatively, a modified and stronger AtMYB103 promoter may also be used for expression. We have identified a short sequence immediately upstream from the TATA box of the AtMYB103 gene that is essential for tapetum expression and multiple copies may provide a means of increasing expression. Similarly in the barnase/barstar system driven by a tapetum-specific promoter TA29, identification of efficient restorer (barstar) lines in *Brassica juncea* (Indian oilseed mustard) proved to be difficult. Only one in 54 cross-combinations between male sterile and restorer lines adequately restored F1 male fertility. The inability to identify more cross-combinations restoring male fertility was attributed to insufficient levels of barstar protein (inhibitor to barnase) at the appropriate developmental stages. An efficient restorer was obtained by incorporating into a transforming construct two barstar transcription units driven by the TA29 and A9 promoters, respectively.

The work in this experiment provides the first example of a transcription factor targeted to achieve reversible male sterility. The system can be adapted to crop plants for hybrid seed production. AtMYB103 homologs occur in crop plants such as canola, rice and wheat. These homologs are also expressed in anthers (our unpublished results).

Transgenic male sterility has been generated using a number of transgenes. The male sterility induced by the transgenes has provided valuable information regarding anther and pollen development. However, their potential commercial application for hybrid seed production is limited by the lack of efficient and economical methods to maintain (multiply) the male sterile lines and/or the lack of suitable restorers. The barnase/barstar system has been used successfully for the commercial production of hybrids. The system contains an efficient restorer but suffers from an inability to obtain plants homozygous for the sterility-inducing transgenes as the hemizygous plants are male sterile. A male sterile line is maintained by crossing with an isogenic wild-type line. Consequently, half of the progeny are male fertile. One strategy for removing the male fertile progeny has been to link a herbicide-resistant gene to the transgene and spray the progeny plants with the herbicide in a hybrid seed production field. Extra care is required to eliminate all fertile plants to ensure the purity of the hybrid seed. The elimination of fertile progeny requires twice as much female parent seed, which could limit the applicability of the system in crops with a low multiplication factor (low number of seeds per plant) such as wheat. Furthermore, the spraying results in uneven distribution of female plants and reduces hybrid seed yield in some crops such as corn.

An inducible component (activator) can be incorporated into the AtMYB103 system to produce homozygous female lines. The activator is identical to the restorer except that it contains a ligand-binding domain of the ecdysone receptor (EcR) fused in frame with AtMYB103 (103EcR) (FIG. 49A). The ecdysone receptor is advantageous over other receptors as it is the target of several commercially available insecticides (ecdysone agonists). These non-steroidal ecdysone agonists have been used in many field applications. The 103EcR may be linked to the chimeric repressor 103EAR. The 103EcR chimeric protein remains inactive in the absence of ecdysone agonist but is activated to restore male fertility following agonist spraying. Hence, a male sterile and homozygous female line can be generated and maintained with agonist spraying (FIG. 49A). In a hybrid seed production field, all female plants are male sterile and no spraying is required. Hence the reversible male sterility overcomes the disadvantages associated with the herbicide strategy. Furthermore, it requires agonist spraying over a smaller acreage only for the multiplication of female lines. We have successfully tested a similar inducible component in the insertion mutant.

The chimeric repressor can also be modified to generate an inducible male sterility system which does not require a repressor (FIG. 49B). The ligand-binding domain of the ecdysone receptor is fused with the chimeric repressor and introduced into a female line. Upon spraying with an ecdysone agonist, the chimeric repressor is activated to induce male sterility. The homozygous female line is male fertile and becomes male sterile when sprayed with an ecdysone agonist in a hybrid seed production field (FIG. 49B).

TABLE 2

Primer sequences

| Name | Gene | Position* | Nucleotidesequence |
|---|---|---|---|
| EAR-RT | EAR | | AGTTCAAGGTCCAAATCTAAA |
| EAR103R | 103 | +1471 | ATGGAAGCTTACGCAAATCCTAGCCTGAGTTCAAGGTC |
| | EAR | | CAAATCTAAACCCATATGATTGATGAGATCATCAG |
| EAR103F | 103 | -1105 | AAGGTCTAGAGGCAAGGAGCTTCTATGGCCAA |
| 103UTR | 103 | +1506 | GAAAAAGGAAAAAACTTAGAACCA |
| 103F5 | 103 | +326 | TATCATTGTCAAGTTTCACTCTGTT |
| 103-137For | 103 | -137 | TCTTTGGGTGGGGCAATCTTTGAT |
| 103-52For | 103 | -52 | AAGAGTAATCAAATCGATCAAGAGA |
| 103-3 | 103 | -3 | 5'AGCCCCGGGCAAATGGGTCGGATTCCATGTTGT3' |
| 103 + 1004Rev | 103 | +1004 | GAGCAAGTGAAGCATCTCGTCCTTG |
| 103 + 1474Rev | 103 | +1474 | CGACAGCTGTCAAACCATATGATTGATGAGATC |
| 103 + 1476Rev | 103 | +1476 | 5'GCTGAGCTCAATCAAACCATATGATTGATGAG3' |
| At39 + 4For | 39 | +4 | TATTTCCCGGCTGTAAAAGTTCTTCTTATTA |
| At39-1260 | 39 | -1264 | AAGGTCTAGAGTTCCCATGCCTTTAGATTCGGA |
| pAC161Rev | TDNA | LB | GGGCTACACTGAATTGGTAGCTC |
| TUB1 | Tubulin | +309 | GGACACTACACTGAAGGTGCTGAG |
| TUB2 | Tubulin | +1065 | GGCTCTGTATTGCTGTGATCCACG |

*The first nucleotides of the coding sequences are designated +1.

The invention claimed is:

1. A nucleic acid construct comprising a nucleic acid molecule encoding AtMYB103 having SEQ ID NO: 22 or a nucleic acid molecule encoding an orthologue or homologue of AtMYB103 having at least 75% amino acid sequence identity with SEQ ID NO: 22 or a nucleic acid molecule encoding an orthologue or homologue of AtMYB103 comprising a fragment of at least 150 amino acid residues having at least 85% sequence identity to SEQ ID NO: 22; and a heterologous repressor motif.

2. The construct of claim 1, wherein the orthologue or homologue of AtMYB103 comprises an amino acid sequence having SEQ ID NO:3, SEQ ID NO: 5, or [SEQ ID NO: 11, ]SEQ ID NO: 18[ or SEQ ID NO: 20].

3. The construct of claim 1, wherein the repressor motif comprises the EAR repressor motif encoding the amino acid sequence LXLXLX (SEQ ID NO:29) where L is the amino acid Leucine and X represents any amino acid.

4. The construct of claim 3, wherein the repressor motif encodes LDLNLELRISPP (SEQ ID NO: 30) or LDLDLEL-RLGFA (SEQ ID NO: 27).

5. A plant cell comprising the construct of claim 1.

6. The construct of claim 1 further comprising a strong anther specific promoter or an MYB103 promoter.

7. The construct of claim 6, wherein the strong anther specific promoter is Ta39.

8. A transgenic plant generated from the plant cell of claim 5 or seed, tissues, roots, shoots, tubers or propagating material thereof or progeny thereof, comprising the construct.

9. The plant of claim 8, wherein the plant is a legume, crop, cereal, native grass, fruiting plant or flowering plant.

10. The plant of claim 8, wherein the plant is a Brassicaceae, Solanaceae species, potato, cole vegetable, cabbage, kale, collard, turnip, rutabaga, kohlrabi, Brussels sprout, cauliflower, mustard, oilseed, crucifer, broccoli, canola, tomato, grain legume, wheat, barley, maize, tobacco or rice.

11. The construct of claim 1 further comprising an ecdysone ligand binding domain (EcR).

* * * * *

UNITED STATES PATENT AND TRADEMARK OFFICE
CERTIFICATE OF CORRECTION

PATENT NO. : 8,624,086 B2  
APPLICATION NO. : 13/430579  
DATED : January 7, 2014  
INVENTOR(S) : Roger Parish et al.

Page 1 of 1

It is certified that error appears in the above-identified patent and that said Letters Patent is hereby corrected as shown below:

On the Title Page, Item (73) should read

(73) Assignees: La Trobe University, Bundoora, Victoria (AU)  
Grains Research and Development Corporation, Barton, Australian Capital Territory (AU)  
Agriculture Victoria Services Pty. Ltd., Attwood, Victoria (AU)

Signed and Sealed this
Fourteenth Day of October, 2014

Michelle K. Lee
*Deputy Director of the United States Patent and Trademark Office*